(12) United States Patent
Lee

(10) Patent No.: US 10,517,322 B1
(45) Date of Patent: Dec. 31, 2019

(54) DIETARY SUPPLEMENT FORMULATIONS FOR PROMOTING SLEEP

(71) Applicant: Life Kitchen, LLC, San Diego, CA (US)

(72) Inventor: James Wukjae Lee, San Diego, CA (US)

(73) Assignee: Life Kitchen, LLC, San Diego, CA (US)

( * ) Notice: Subject to any disclaimer, the term of this patent is extended or adjusted under 35 U.S.C. 154(b) by 0 days.

(21) Appl. No.: 16/356,621

(22) Filed: Mar. 18, 2019

Related U.S. Application Data

(60) Provisional application No. 62/645,005, filed on Mar. 19, 2018.

(51) Int. Cl.
| | |
|---|---|
| *A61K 31/4045* | (2006.01) |
| *A61K 31/197* | (2006.01) |
| *A23L 29/00* | (2016.01) |
| *A61P 25/24* | (2006.01) |
| *A61P 25/22* | (2006.01) |
| *A61K 36/84* | (2006.01) |
| *A61K 9/28* | (2006.01) |
| *A61K 36/28* | (2006.01) |
| *A61K 31/685* | (2006.01) |

(52) U.S. Cl.
CPC ............... *A23L 29/03* (2016.08); *A61K 9/28* (2013.01); *A61K 31/197* (2013.01); *A61K 31/4045* (2013.01); *A61K 36/28* (2013.01); *A61K 36/84* (2013.01); *A61P 25/22* (2018.01); *A61P 25/24* (2018.01); *A23V 2200/322* (2013.01); *A23V 2250/06* (2013.01)

(58) Field of Classification Search
None
See application file for complete search history.

(56) References Cited

U.S. PATENT DOCUMENTS

| | | | |
|---|---|---|---|
| 10,143,223 B1 | 12/2018 | Kharait et al. | |
| 10,179,144 B2 | 1/2019 | Duronio et al. | |
| 10,369,182 B2 * | 8/2019 | Cohen | A61K 36/53 |
| 2014/0017337 A1 * | 1/2014 | Amoruso | A61K 45/06 424/643 |
| 2014/0107080 A1 * | 4/2014 | Koga | A23L 2/52 514/121 |

OTHER PUBLICATIONS

Watson et al.: Neuropharmacology of Sleep and Wakefulness; Sleep Med Clin.; 5(4); 513-528 (2010).

* cited by examiner

*Primary Examiner* — Bong-Sook Baek
(74) *Attorney, Agent, or Firm* — Wilson Sonsini Goodrich & Rosati

(57) ABSTRACT

Provided herein are formulations and methods helping individuals enhance cognitive function, facilitate memory processing, induce and maintain sleep, stabilize mood, reduce symptoms of stress and anxiety, facilitate energy production, improve mental and emotional health, or support long-term brain health.

17 Claims, 2 Drawing Sheets

DIETARY SUPPLEMENT FORMULATIONS FOR PROMOTING SLEEP

CROSS REFERENCE

This application claims the benefit of and right of priority to U.S. Provisional Application No. 62/645,005 filed Mar. 19, 2018, which is incorporated herein by reference in its entirety.

BACKGROUND

Dietary supplements are products intended to supplement the diet. Dietary supplements can contain one or more dietary ingredients, including vitamins, minerals, herbs, amino acids, and other substances. Dietary supplements can be taken by mouth as a pill, capsule, tablet, or liquid, and can usually be labeled on the front panel as being a dietary supplement.

Dietary supplements can carry a plurality of specific health benefits. These health benefits can include helping maintain proper metabolism, promoting tissue maintenance and repair, and preventing diseases. For maintaining proper metabolism, dietary supplements can help individuals break down the carbohydrates, proteins and fats from each meal, and absorb the other nutrients in the meal. For promoting tissue maintenance and repair, dietary supplements can help individuals' bodies produce proteins that make up healthy new tissue to replace old or damaged tissue. For preventing diseases, dietary supplements can help individuals' bodies neutralize harmful chemicals that cause certain diseases.

SUMMARY

The subject matter disclosed herein was created at the intersection of biochemistry (the study of the molecules that make up life), molecular biophysics (the laws that define the interactions of those molecules), dietary nutrition (including an assessment of amino acid intake), medicine (the study of human disease and treatment), and the intense passion of the inventor who's life depended on the success of these inventions.

The inventive formulations and methods of the subject matter disclosed herein have been specifically engineered to support various metabolic processes that are necessary for life. Some of the metabolic processes supported by the subject matter disclosed herein include, but are not limited to, the Kreb's cycle (e.g., to increase energy production), DNA/RNA/Protein synthesis (e.g., to increase neurogenesis and support brain function), neurotransmitter synthesis (e.g., to support brain function), cell wall synthesis (e.g., to support brain structure and function), adenosine optimization (e.g., to increase cognitive stamina), inflammatory mechanisms (to enhance long-term stability of organs), oxidative mechanisms (e.g., to reduce oxidative stress within biochemistry of the human body), and vasodilation (e.g., to increase nutrient supply and transport).

In some aspects, the subject matter described herein comprises a system that provides essential amino acids to be supplied and consumed by a person (e.g., in one, two, three, or more dosage forms). In additional aspects, the subject matter described herein comprises a system that provides for essential minerals that are not prevalent in the human diet (e.g., in one, two, three, or more dosage forms). In another aspect, the subject matter disclosed herein comprises a system that provides essential omega-3 acids that are not prevalent in the human diet (e.g., in one, two, three, or more dosage forms). In another aspect, the subject matter described herein comprises a system that provides essential amino acids that are necessary for neurological function. Without one or more essential biomolecules, life sustaining biochemical processes in a biological organism would cease to function. More generally, the subject matter described herein comprises electrolytes and nutritional herbs to enhance the processes disclosed herein.

In addition to essential biomolecules, the subject matter described herein includes non-essential biomolecules. The non-essential biomolecules, in some embodiments, are vital to the enzymatic chemical reactions that are responsible for cellular energy production. Thus, in some embodiments, the subject matter disclosed herein aims to enhance the availability of these biomolecules to support the metabolic processes disclosed herein.

In some embodiments, the formulations described herein can be reduced to three distinct categories of formulations. The ingredients in the respective categories have been specifically designed, chosen, and/or included, with biomedical principles in mind, to create synergistic mechanisms to achieve their respective, desired effects described herein. An example of a synergistic combination to achieve the desired effect of the subject matter disclosed herein includes, but is not limited to, category 1 formulations—intended to enhance cognitive function throughout the subject's daily activities—contain ingredients that support both dopamine function (the neurotransmitter for activity), and adenosine sequestration (enhance cognitive stamina) to synergistically enhance the subject's cognitive function throughout the subject's daily activities. Another example of a synergistic effect created by the subject matter disclosed herein includes, but is not limited to, category 2 formulations—intended to enhance sleep quality—contain ingredients that help set the sleep wake cycle, support delta wave production during sleep (most important stage of sleep for ridding Beta amyloid plaque associates with dementia), and relax muscle to synergistically enhance the subject's sleep quality. Yet another example of a synergistic effect created by the subject matter disclosed herein includes, but is not limited to, category 3 formulations—intended to enhance energy production/restoration—contain ingredients that support cell wall synthesis, enhance vasodilation, and supplement the Kreb's Cycle to synergistically enhance the subject's energy production/restoration.

Disclosed herein are dietary supplement formulations and methods. These formulations and methods can be useful for helping individuals, among other things, enhance or support cognitive function and boost or increase alertness, facilitate memory processing, support central nervous system performance and regulation, increase motivation and drive, improve focus, improve or refine clarity and concentration, increase speed of cognition and information processing, improve wakefulness and alertness, reduce anxiety and stress, increase energy levels, increase stamina or endurance, improve reaction times, enhance creativity, balance mood, enhance clarity, increase or strengthen mental stamina, eliminate mental gridlock, boost speed of thought, regulate the synthesis of a number of neurotransmitters, improve brain cell function and production, increase antioxidant activity and brain blood flow, modulate pain receptors, or enhance neural growth and neuroplasticity.

The formulations and methods of dietary supplements disclosed herein can also be useful for helping individuals, among other things, induce and maintain sleep, encourage natural sleep, calm down, stabilize their mood, regulate their clock and sleep-wake cycle, facilitate memory processing, support nervous system health, promote relaxation, reduce symptoms of stress and anxiety, improve or support cognition and memory, improve quality of sleep, reduce time required to fall asleep, achieve deep and restful sleep, uplift mood, offset caffeine in other dietary supplements, reduce brain cell activity, result in a relaxed state, wake up feeling refreshed and enable rejuvenated mornings, optimize memory consolidation, recovery, and neuroprotective processes, enhance cognition generally and the day after quality night of sleep, or invites or causes a human to feel more relaxed and balanced.

The formulations of dietary supplements disclosed herein can also be useful for helping individuals, among other things, promote or support learning and memory, support a better mood, support cognitive function, restore and stabilize cells, facilitate energy production, lift vitality, improve mental and emotional health, stabilize metabolism rate and mood, facilitate chemical reactions critical to health, limit stress and anxiety, improve attention and focus, improve mental performance and ability to concentrate, improve or empower overall well-being and better energy, promote cognitive health, or support long-term brain health.

In an aspect, an orally administered supplement formulation in unit dose form can comprise one or more adaptogens, one or more antioxidants, an agent to maintain healthy absorption of nutrients, and an agent to maintain healthy cognitive function, wherein the agent to maintain healthy cognitive function can be present in the formulation, individually, in each case, in an amount of from about 0.5 mg to about 4 mg. The one or more adaptogens can comprise *ginseng* root. The *ginseng* root can be Korean *ginseng* root. In some embodiments, the *ginseng* root can be present in the formulation, individually, in each case, in an amount of from about 0.1 mg to about 6 mg. In some embodiments, the *ginseng* root can be present in the formulation, individually, in each case, in an amount of from about 0.5 mg to about 4 mg. The one or more adaptogens can comprise ginkgo leaf extract. The ginkgo leaf extract can be present in the formulation, individually, in each case, in an amount of from about 10 mg to about 80 mg. The agent to maintain healthy cognitive function can comprise *rhodiola* root extract. The one or more antioxidants can comprise green tea leaf extract. The green tea leaf extract can be present in the formulation, individually, in each case, in an amount of from about 50 mg to about 600 mg. The green tea leaf extract can be present in the formulation, individually, in each case, in an amount of about 300 mg. The one or more antioxidants can comprise ginger root extract. The ginger root extract can be present in the formulation, individually, in each case, in an amount of from about 10 mg to about 80 mg. The agent to maintain healthy absorption of nutrients can comprise cayenne pepper. The cayenne pepper can be present in the formulation, individually, in each case, in an amount of from about 8 mg to about 30 mg. The formulation can comprise *ginseng* root, ginkgo leaf extract, ginger root extract, cayenne pepper, *rhodiola* root extract, and green tea leaf extract.

In another aspect, an orally administered supplement formulation in unit dose form can comprise an antioxidant, one or more compounds to maintain healthy cognitive performance, and an amino acid or a salt thereof, wherein the amino acid or a salt thereof can be present in the formulation, individually, in each case, in an amount of from about 10 mg to about 400 mg. The orally administered supplement can comprise the amino acid that can be L-theanine. The L-theanine can be present in the formulation in an amount of about 180 mg. The antioxidant can comprise resveratrol or a salt thereof. The resveratrol or a salt thereof can be present in the formulation, individually, in each case, in an amount of from about 8 mg to about 30 mg. The one or more compounds to maintain healthy cognitive performance can comprise bacopa leaf extract. The bacopa leaf extract can be present in the formulation, individually, in each case, in an amount of from about 10 mg to about 600 mg. The one or more compounds to maintain healthy cognitive performance can comprise dimethylaminoethanol or a salt thereof. The dimethylaminoethanol or a salt thereof can be present in the formulation, individually, in each case, in an amount of from about 8 mg to about 30 mg. The one or more compounds to maintain cognitive performance can comprise pyrroloquinoline quinone or a salt thereof. The pyrroloquinoline quinone or a salt thereof can be present in the formulation, individually, in each case, in an amount of from about 0.1 mg to about 4 mg. The one or more compounds to maintain healthy cognitive performance can optionally comprise huperzine A or a salt thereof. The huperzine A or a salt thereof can optionally be present in the formulation, individually, in each case, in an amount of from about 0.05 mg to about 4 mg. The formulation can comprise bacopa leaf extract, L-theanine or a salt thereof, resveratrol or a salt thereof, dimethylaminoethanol or a salt thereof, pyrroloquinoline quinone or a salt thereof, and optionally huperzine A or a salt thereof.

In another aspect, an orally administered supplement formulation in unit dose form can comprise an energy recycler, a first amino acid or a salt thereof, a second amino acid or a salt thereof, a third amino acid or a salt thereof, a fourth amino acid or a salt thereof, and an antioxidant, wherein the antioxidant can be present in the formulation, individually, in each case, in an amount of from about 10 mg to about 150 mg. The antioxidant can comprise taurine or a salt thereof. The taurine or a salt thereof can be present in the formulation, individually, in each case, in an amount of about 60 mg. The orally administered supplement can comprise the first amino acid that can be DL-phenylalanine. The DL-phenylalanine can be present in the formulation in an amount of from about 10 mg to about 150 mg. The second amino acid or a salt thereof can comprise L-tyrosine or a salt thereof. The L-tyrosine can be present as a hydrochloric acid salt in the formulation in an amount of from about 10 mg to about 150 mg. The third amino acid or a salt thereof can comprise L-arginine or a salt thereof. The L-arginine can be present as a hydrochloric acid salt in the formulation in an amount of from about 10 mg to about 150 mg. The fourth amino acid can be 5-hydroxytryptophan. The 5-hydroxytryptophan can be present in the formulation, individually, in each case, in an amount of from about 10 mg to about 50 mg. The energy recycler can comprise creatine or a salt thereof. The creatine can be creatine monohydrate, wherein the creatine monohydrate can be present in the formulation in an amount of from about 10 mg to about 50 mg. The formulation can comprise DL-phenylalanine or a salt thereof, L-tyrosine or a salt thereof, L-arginine or a salt thereof, taurine or a salt thereof, 5-hydroxytryptophan or a salt thereof, and creatine or a salt thereof.

In another aspect, the formulation can comprise *ginseng* root, ginkgo leaf extract, ginger root extract, cayenne pepper, *rhodiola* root extract, green tea leaf extract, bacopa leaf extract, L-theanine or a salt thereof, resveratrol or a salt thereof, dimethylaminoethanol or a salt thereof, pyrroloquinoline quinone or a salt thereof, DL-phenylalanine or a salt thereof, L-tyrosine or a salt thereof, L-arginine or a salt thereof, taurine or a salt thereof, 5-hydroxytryptophan or a salt thereof, creatine or a salt thereof, and optionally huperzine A or a salt thereof. The formulation can be formulated as a capsule. The formulation can be formulated as a tablet. The formulation can be a heterogeneous mixture. The formulation can be a homogenous mixture. The formulation further can comprise an excipient, wherein the excipient can be selected from the group consisting of cellulose (cellulose gum), stearic acid, silicon dioxide (optionally as bamboo extract), magnesium stearate, titanium dioxide, natural vanillin, polyethylene glycol, riboflavin, carnauba wax, and any combination thereof. The formulation can be contained in a container. The formulation can retain at least about 80% of supplement activity for at least a year when stored in a sealed container, wherein the sealed container can be placed in an environment having a temperature of about 25° C. and about 50% relative humility.

In another aspect, a method can comprise orally administering the supplement formulation in unit dose form to a human. The method can be a method of supporting cognitive health of the human. The method can be a method of supporting clarity, supporting concentration, or supporting clarity and concentration of the human. The method can be a method of boosting alertness, boosting wakefulness, or boosting alertness and wakefulness of the human.

In another aspect, a method of making a supplement formulation in unit dose form can comprise combining one or more adaptogens, one or more antioxidants, an agent to maintain healthy absorption of nutrients, and an agent to maintain healthy cognitive function, wherein the agent to maintain healthy cognitive function can be present in the formulation, individually, in each case, in an amount of from about 0.5 mg to about 4 mg. In some embodiments, a method of making a supplement formulation in unit dose form can comprise combining an antioxidant, one or more compounds to maintain healthy cognitive performance, and an amino acid or a salt thereof, wherein the amino acid or a salt thereof can be present in the formulation, individually, in each case, in an amount of from about 10 mg to about 400 mg. In some embodiments, a method of making a supplement formulation in unit dose form can comprise combining an energy recycler, a first amino acid or a salt thereof, a second amino acid or a salt thereof, a third amino acid or a salt thereof, a fourth amino acid or a salt thereof, and an antioxidant, wherein the antioxidant can be present in the formulation, individually, in each case, in an amount of from about 10 mg to about 150 mg.

In an aspect, an orally administered supplement formulation in unit dose form can comprise a first amino acid or a salt thereof, a second amino acid or a salt thereof, an antioxidant, a precursor for a neurotransmitter, an agent to promote or encourage healthy sleep, an agent to maintain healthy cognitive function, and a compound to help maintain healthy brain function, wherein the compound to help maintain healthy brain function can be present in the formulation, individually, in each case, in an amount of from about 8 mg to about 40 mg. The compound to help maintain healthy brain function can comprise myo-inositol. The myo-inositol can be present in the formulation in an amount of about 16 mg. The first amino acid can be gamma-aminobutyric acid (GABA) or L-glutamine. The GABA or L-glutamine can be present in the formulation, individually, in each case, in an amount of from about 10 mg to about 600 mg. The first amino acid can be L-glutamine. In some embodiments, the L-glutamine is present in the formulation at about 20 mg. The second amino acid can be L-theanine. The L-theanine can be present in the formulation, individually, in each case, in an amount of from about 10 mg to about 300 mg. The antioxidant can comprise taurine or a salt thereof. The taurine or a salt thereof can be present in the formulation, individually, in each case, in an amount of from about 10 mg to about 120 mg. The precursor for a neurotransmitter can comprise GABA or L-glutamine or a salt thereof. In some embodiments, GABA or L-glutamine or a salt thereof can be present in the formulation, individually, in each case, in an amount of from about 1 mg to about 50 mg. In some embodiments, the precursor for a neurotransmitter is GABA. In some embodiments, the GABA is present in the formulation at about 300 mg. In some embodiments, L-glutamine or a salt thereof can be present in the formulation, individually, in each case, in an amount of from about 8 mg to about 50 mg. The agent to promote or encourage healthy sleep can comprise melatonin or a salt thereof. The melatonin or a salt thereof can be present in the formulation, individually, in each case, in an amount of from about 1 mg to about 20 mg. In some embodiments, the melatonin or a salt thereof can be present in the formulation, individually, in each case, in an amount of from about 1 mg to about 20 mg. In some embodiments, the melatonin or a salt thereof can be present in the formulation, individually, in each case, in an amount of from about 7 mg to about 20 mg. The agent to maintain healthy cognitive function can comprise phosphatidylserine or a salt thereof. The phosphatidylserine or a salt thereof can be present in the formulation, individually, in each case, in an amount of from about 0.1 mg to about 4 mg. In some embodiments, the phosphatidylserine or a salt thereof can be present in the formulation, individually, in each case, in an amount of from about 0.5 mg to about 4 mg. The formulation can comprise GABA or a salt thereof, L-theanine or a salt thereof, taurine or a salt thereof, L-glutamine or a salt thereof, myo-inositol, melatonin or a salt thereof, and phosphatidylserine or a salt thereof.

In another aspect, an orally administered supplement formulation in unit dose form can comprise one or more compounds to promote or encourage healthy sleep, a precursor for a neurotransmitter, and an antioxidant, wherein the antioxidant can be present in the formulation, individually, in each case, in an amount of from about 8 mg to about 60 mg. The antioxidant can comprise ashwagandha root extract. The ashwagandha root extract can be present in the formulation, individually, in each case, in an amount of about 28 mg. The one or more compounds to promote or encourage healthy sleep can comprise valerian root extract. The valerian root extract can be present in the formulation, individually, in each case, in an amount of from about 50 mg to about 300 mg. The one or more compounds to promote or encourage healthy sleep can comprise chamomile flower extract. The chamomile flower extract can be present in the formulation, individually, in each case, in an amount of from about 10 mg to about 50 mg. The one or more compounds to promote or encourage healthy sleep can comprise hops flower extract. The hops flower extract can be present in the formulation, individually, in each case, in an amount of from about 10 mg to about 50 mg. The precursor for a neurotransmitter can comprise 5-hydroxytryptophan or a salt thereof. The 5-hydroxytryptophan or a salt thereof can be present in the formulation, individually, in each case, in an amount of from about 8 mg to about 60 mg. The one or more compounds to promote or encourage healthy sleep can comprise passion flower extract. The passion flower extract can be present in the formulation, individually, in each case, in an amount of from about 8 mg to about 60 mg. The one or more compounds to promote or encourage healthy sleep can comprise lemon balm leaf extract. The lemon balm leaf extract can be present in the formulation, individually, in each case, in an amount of from about 1 mg to about 60 mg. In some embodiments, the lemon balm leaf extract can be present in the formulation, individually, in each case, in an amount of from about 8 mg to about 60 mg. The formulation can comprise valerian root extract, 5-hydroxytryptophan or a salt thereof, ashwagandha root extract, chamomile flower extract, hops flower extract, passion flower extract, and lemon balm leaf extract.

In another aspect, the formulation can comprise GABA or a salt thereof, L-theanine or a salt thereof, taurine or a salt thereof, L-glutamine or a salt thereof, myo-inositol, melatonin or a salt thereof, phosphatidylserine or a salt thereof, valerian root extract, 5-hydroxytryptophan or a salt thereof, ashwagandha root extract, chamomile flower extract, hops flower extract, passion flower extract, and lemon balm leaf extract. The formulation can be formulated as a capsule. The formulation can be formulated as a tablet. The formulation can be a heterogeneous mixture. The formulation can be a homogenous mixture. The formulation further can comprise an excipient, wherein the excipient can be selected from the group consisting of cellulose (cellulose gum), silicon dioxide (bamboo extract), stearic acid, magnesium stearate, titanium dioxide, vanilla, polyethylene glycol, chlorophyll, carnauba wax, peppermint, caramel, and any combination thereof. The formulation can be contained in a container. The formulation can retain at least about 80% of supplement activity for at least a year when stored in a sealed container, wherein the sealed container can be placed in an environment having a temperature of about 25° C. and about 50% relative humility.

In another aspect, a method can comprise orally administering the formulation in unit dose form to a human. The method can be a method of promoting or encouraging sleep. The method can be a method of supporting health, supporting well-being, or supporting health and well-being of the human. The method can be a method of helping the human wake up feeling refreshed. The method can be a method of supporting cognitive health. The method can be a method of enabling rejuvenated mornings for a human. The method can be a method of conferring a state of relaxation and balance on an individual. In some embodiments, a method of making a supplement formulation in unit dose form can comprise combining a first amino acid or a salt thereof, a second amino acid or a salt thereof, an antioxidant, a precursor for a neurotransmitter, an agent to promote or encourage healthy sleep, an agent to maintain healthy cognitive function, and a compound to help maintain healthy brain function, wherein the compound to help maintain healthy brain function can be present in the formulation, individually, in each case, in an amount of from about 8 mg to about 40 mg. A method of making a supplement formulation in unit dose form can comprise combining one or more compounds to promote or encourage healthy sleep, a precursor for a neurotransmitter, and an antioxidant, wherein the antioxidant can be present in the formulation, individually, in each case, in an amount of from about 8 mg to about 60 mg.

In an aspect, an orally administered supplement formulation in unit dose form can comprise one or more agents to maintain healthy cognitive function, one or more ingredients to help maintain healthy memory performance, and a compound to help maintain healthy brain function, wherein the compound to help maintain healthy brain function can be present in the formulation, individually, in each case, in an amount of from about 10 mg to about 160 mg. The compound to help maintain healthy brain function can comprise myo-inositol. The myo-inositol can be present in the formulation, individually, in each case, in an amount from about 40 mg to about 120 mg. In some embodiments, the myo-inositol can be present in the formulation, individually, in each case, in an amount of about 80 mg. The one or more agents to maintain healthy cognitive function can comprise phosphatidylcholine or a salt thereof. The phosphatidylcholine or a salt thereof can be present in the formulation, individually, in each case, in an amount of from about 10 mg to about 300 mg or about 1 mg to about 300 mg. The one or more agents to maintain healthy cognitive function can comprise phosphatidylserine or a salt thereof. The phosphatidylserine or a salt thereof can be present in the formulation, individually, in each case, in an amount of from about 1 mg to about 20 mg. In some embodiments, the phosphatidylserine or a salt thereof can be present in the formulation, individually, in each case, in an amount of from about 6 mg to about 20 mg. The one or more ingredients to help maintain healthy memory performance can comprise alpha-glycerophosphocholine or a salt thereof. The alpha-glycerophosphocholine or a salt thereof can be present in the formulation, individually, in each case, in an amount of from about 1 mg to about 20 mg. In some embodiments, the alpha-glycerophosphocholine or a salt thereof can be present in the formulation, individually, in each case, in an amount of from about 6 mg to about 20 mg. The one or more ingredients to help maintain healthy memory performance can optionally comprise citicoline or a salt thereof. The citicoline or a salt thereof can optionally be present in the formulation, individually, in each case, in an amount of from about 1 mg to about 30 mg. In some embodiments, the citicoline or a salt thereof can optionally be present in the formulation, individually, in each case, in an amount of from about 5 mg to about 30 mg. The one or more ingredients to help maintain healthy memory performance can comprise choline (optionally as choline bitartrate or citicoline). The choline can be present in the formulation, individually, in each case, in an amount of from about 10 mg to about 100 mg or from about 10 mg to about 200 mg. The one or more agents to maintain healthy cognitive function can optionally comprise soy lecithin or a salt thereof. The soy lecithin or a salt thereof can optionally be present in the formulation, individually, in each case, in an amount of from about 1 mg to about 100 mg. In some embodiments, the soy lecithin or a salt thereof can optionally be present in the formulation, individually, in each case, in an amount of from about 10 mg to about 100 mg. The formulation can comprise phosphatidylcholine or a salt thereof, myo-inositol, choline, optionally soy lecithin or a salt thereof, alpha-glycerophosphocholine or a salt thereof, phosphatidylserine or a salt thereof, and optionally citicoline or a salt thereof.

In another aspect, an orally administered supplement formulation in unit dose form can comprise one or more antioxidants, an amino acid or a salt thereof, one or more agents to help maintain healthy blood circulation, and a compound to help maintain healthy brain function, wherein the compound to help maintain healthy brain function can be present in the formulation, individually, in each case, in an amount of from about 10 mg to about 50 mg. In some embodiments, the supplement formulation can further comprise chlorophyll and menaquinone MK7 (K2). The compound to help maintain healthy brain function can comprise acetyl-L-carnitine or a salt thereof. The acetyl-L-carnitine or a salt thereof can be present in the formulation, individually, in each case, in an amount of about 25 mg. The one or more antioxidants can comprise taurine or a salt thereof. The taurine or a salt thereof can be present in the formulation, individually, in each case, in an amount of from about 10 mg to about 80 mg. The one or more antioxidants can comprise alpha lipoic acid or a salt thereof. The alpha lipoic acid or a salt thereof can be present in the formulation, individually, in each case, in an amount of from about 10 mg to about 50 mg. The one or more antioxidants can comprise resveratrol or a salt thereof. The resveratrol or a salt thereof can be present in the formulation, individually, in each case, in an amount of from about 10 mg to about 50 mg. The one or more antioxidants can comprise quercetin or a salt thereof. The quercetin or a salt thereof can be present in the formulation, individually, in each case, in an amount of from about 0.5 mg to about 10 mg. In some embodiments, the quercetin or a salt thereof can be present in the formulation, individually, in each case, in an amount of from about 0.5 mg to about 5 mg. The one or more antioxidants can comprise astaxanthin or a salt thereof. The astaxanthin or a salt thereof can be present in the formulation, individually, in each case, in an amount of from about 0.1 mg to about 4 mg. In some embodiments, the astaxanthin or a salt thereof can be present in the formulation, individually, in each case, in an amount of from about 0.5 mg to about 4 mg. The one or more antioxidants can comprise CoQ10. The CoQ10 can be present in the formulation, individually, in each case, in an amount of from about 0.01 mg to about 4 mg. The amino acid can be L-arginine. The L-arginine can be present as a hydrochloric acid salt in the formulation, individually, in each case, in an amount of from about 10 mg to about 100 mg. The one or more agents to help maintain healthy blood circulation can comprise L-citrulline or a salt thereof. The L-citrulline or a salt thereof can be present in the formulation, individually, in each case, in an amount of from about 8 mg to about 80 mg. The one or more agents to help maintain healthy blood circulation can comprise beet root extract. The beet root extract can be present in the formulation, individually, in each case, in an amount of from about 8 mg to about 80 mg. The formulation can comprise L-arginine or a salt thereof, L-citrulline or a salt thereof, taurine or a salt thereof, beet root extract, acetyl-L-carnitine or a salt thereof, alpha lipoic acid or a salt thereof, resveratrol or a salt thereof, quercetin or a salt thereof, astaxanthin or a salt thereof, chlorophyll or a salt thereof, menaquinone MK7 (K2) or a salt thereof, and CoQ10.

In another aspect, an orally administered supplement formulation in unit dose form can comprise one or more antioxidants, one or more adaptogens, an agent to help maintain healthy blood circulation, an agent to maintain healthy absorption of nutrients, and an agent to maintain healthy heart function, wherein the agent to maintain healthy heart function can be present in the formulation, individually, in each case, in an amount of from about 10 mg to about 150 mg. The agent to maintain healthy heart function can optionally comprise flax seed oil. The flax seed oil can optionally be present in the formulation, individually, in each case, in an amount of about 100 mg. The one or more antioxidants can comprise grape seed extract. The grape seed extract can be present in the formulation, individually, in each case, in an amount of from about 10 mg to about 50 mg. The one or more antioxidants can comprise garlic bulb. The garlic bulb can be present in the formulation, individually, in each case, in an amount of from about 5 mg to about 50 mg. The one or more adaptogens can comprise ginkgo leaf extract. The ginkgo leaf extract can be present in the formulation, individually, in each case, in an amount of from about 5 mg to about 50 mg or from about 5 mg to about 100 mg. The one or more adaptogens can comprise *ginseng* root extract. The *ginseng* root extract can be Korean *ginseng* root extract. The *ginseng* root extract can be present in the formulation, individually, in each case, in an amount of from about 5 mg to about 50 mg. The agent to help maintain healthy blood circulation can be turmeric root extract. The turmeric root extract can be present in the formulation, individually, in each case, in an amount of from about 10 mg to about 100 mg or from about 10 mg to about 150 mg. The agent to maintain healthy absorption of nutrients can be cayenne pepper. The cayenne pepper can be present in the formulation, individually, in each case, in an amount of from about 5 mg to about 100 mg. In some embodiments, the cayenne pepper can be present in the formulation, individually, in each case, in an amount of from about 10 mg to about 100 mg. In some embodiments, one or more antioxidants can optionally comprise soybean oil. The soybean oil can optionally be present in the formulation, individually, in each case, in an amount of from about 10 mg to about 200 mg. The one or more adaptogens can comprise boswellia extract. The boswellia extract can be present in the formulation, individually, in each case, in an amount of from about 10 mg to about 50 mg. The one or more antioxidants can comprise rosemary leaf extract. The rosemary leaf extract can be present in the formulation, individually, in each case, in an amount of from about 10 mg to about 50 mg. The one or more antioxidants can comprise ginger root extract. The ginger root extract can be present in the formulation, individually, in each case, in an amount of from about 10 mg to about 80 mg. The ginger root extract can be present in the formulation in an amount of from about 40 mg. The formulation can comprise optionally soybean oil, optionally flax seed oil, turmeric root extract, boswellia extract, grape seed extract, rosemary leaf extract, cayenne pepper, ginkgo leaf extract, Korean *ginseng* root extract, ginger root extract, citrus bioflavonoids concentrate, and garlic bulb, wherein the omega-3 DHA is present in said formulation, individually, in each case, in an amount of from about 10 mg to about 500 mg and the omega-3 EPA is present in said formulation, individually, in each case, in an amount of from about 10 mg to about 200 mg.

In another aspect, the formulation can comprise omega-3 DHA, omega-3 EPA, phosphatidylcholine or a salt thereof, myo-inositol, choline, optionally soy lecithin or a salt thereof, alpha-glycerophosphocholine or a salt thereof, phosphatidylserine or a salt thereof, optionally citicoline or a salt thereof, L-arginine or a salt thereof, L-citrulline or a salt thereof, taurine or a salt thereof, beet root extract, acetyl-L-carnitine or a salt thereof, alpha lipoic acid or a salt thereof, resveratrol or a salt thereof, quercetin or a salt thereof, astaxanthin or a salt thereof, chlorophyll or a salt thereof, menaquinone MK7 (K2) or a salt thereof, CoQ10, optionally soybean oil, optionally flax seed oil, turmeric root extract, boswellia extract, grape seed extract, rosemary leaf extract, cayenne pepper, ginkgo leaf extract, Korean *ginseng* root extract, ginger root extract, citrus bioflavonoids concentrate, and garlic bulb. The formulation can be formulated as a capsule. The formulation can be formulated as a tablet. The formulation can be a heterogeneous mixture. The formulation can be a homogenous mixture. The formulation further can comprise an excipient, wherein the excipient can be selected from the group consisting of cellulose (cellulose gum), stearic acid, silicon dioxide (bamboo extract), magnesium stearate, titanium dioxide, natural vanillin, polyethylene glycol, riboflavin, carnauba wax, and any combination thereof. The formulation can be contained in a container. The formulation can retain at least about 80% of supplement activity for at least a year when stored in a sealed container, wherein the sealed container can be placed in an environment having a temperature of about 25° C. and about 50% relative humidity.

In another aspect, a method can comprise orally administering the formulation in unit dose form to a human. A method can be a method of supporting brain health of the human. A method can be a method of supporting energy, supporting vitality, or supporting energy and vitality of the human. A method can be a method of supporting a healthy lifestyle, supporting well-being, or supporting a healthy lifestyle and well-being of the human. A method of making a supplement formulation in unit dose form can comprise combining one or more agents to maintain healthy cognitive function, one or more ingredients to help maintain healthy memory performance, and a compound to help maintain healthy brain function, wherein the compound to help maintain healthy brain function can be present in the formulation, individually, in each case, in an amount of from about 10 mg to about 160 mg. In some embodiments, a method of making a supplement formulation in unit dose form can comprise combining one or more antioxidants, an amino acid or a salt thereof, one or more agents to help maintain healthy blood circulation, and a compound to help maintain healthy brain function, wherein the compound to help maintain healthy brain function can be present in the formulation, individually, in each case, in an amount of from about 10 mg to about 50 mg. In some embodiments, a method of making a supplement formulation in unit dose form can comprise combining one or more antioxidants, one or more adaptogens, an agent to help maintain healthy blood circulation, an agent to maintain healthy absorption of nutrients, and an agent to maintain healthy heart function, wherein the agent to maintain healthy heart function can be present in the formulation, individually, in each case, in an amount of from about 10 mg to about 150 mg.

In another aspect, the subject matter disclosed herein comprises an orally administered supplement formulation in unit dose form, comprising one or more adaptogens, one or more antioxidants, an agent to maintain healthy absorption of nutrients, and an agent to maintain healthy cognitive function, wherein said agent to maintain healthy cognitive function is present in said formulation, individually, in each case, in an amount of from about 0.5 mg to about 4 mg. In some embodiments, said one or more adaptogens comprise *ginseng* root, or said *ginseng* root comprises Korean *ginseng* root, or said one or more adaptogens comprise ginkgo leaf extract, or said agent to maintain healthy cognitive function comprises *rhodiola* root extract, or said one or more antioxidants comprise green tea leaf extract, or said one or more antioxidants comprise ginger root extract, or said agent to maintain healthy absorption of nutrients comprises cayenne pepper, or combinations thereof.

In some embodiments, said *ginseng* root is present in said formulation, individually, in each case, in an amount of from about 0.5 mg to about 4 mg. In some embodiments, said ginkgo leaf extract is present in said formulation, individually, in each case, in an amount of from about 10 mg to about 80 mg. In some embodiments, said green tea leaf extract is present in said formulation, individually, in each case, in an amount of from about 50 mg to about 600 mg. In some embodiments, said ginger root extract is present in said formulation, individually, in each case, in an amount of from about 10 mg to about 80 mg. In some embodiments, said cayenne pepper is present in said formulation, individually, in each case, in an amount of from about 8 mg to about 30 mg.

In another aspect, the subject matter disclosed herein comprises an orally administered supplement formulation in unit dose form, comprising an antioxidant, one or more compounds to maintain healthy cognitive performance; and an amino acid or a salt thereof, wherein said amino acid or a salt thereof is present in said formulation, individually, in each case, in an amount of from about 10 mg to about 400 mg. In some embodiments, said amino acid that is L-theanine, or said antioxidant comprises resveratrol or a salt thereof, or said one or more compounds to maintain healthy cognitive performance comprise bacopa leaf extract, or said one or more compounds to maintain healthy cognitive performance comprise dimethylaminoethanol or a salt thereof, or said one or more compounds to maintain cognitive performance comprise pyrroloquinoline quinone or a salt thereof, or combinations thereof.

In some embodiments, said L-theanine is present in said formulation in an amount of about 180 mg. In some embodiments, said resveratrol or a salt thereof is present in said formulation, individually, in each case, in an amount of from about 8 mg to about 30 mg. In some embodiments, said bacopa leaf extract is present in said formulation, individually, in each case, in an amount of from about 10 mg to about 600 mg. In some embodiments, said dimethylaminoethanol or a salt thereof is present in said formulation, individually, in each case, in an amount of from about 8 mg to about 30 mg. In some embodiments, said pyrroloquinoline quinone or a salt thereof is present in said formulation, individually, in each case, in an amount of from about 0.1 mg to about 4 mg.

In another aspect, the subject matter disclosed herein comprises an orally administered supplement formulation in unit dose form, comprising an energy recycler, a first amino acid or a salt thereof, a second amino acid or a salt thereof, a third amino acid or a salt thereof, a fourth amino acid or a salt thereof, and an antioxidant, wherein said antioxidant is present in said formulation, individually, in each case, in an amount of from about 10 mg to about 150 mg. In some embodiments, said antioxidant comprises taurine or a salt thereof, or said first amino acid comprises DL-phenylalanine or a salt thereof, or said second amino acid or a salt thereof comprises L-tyrosine or a salt thereof, or said third amino acid or a salt thereof comprises L-arginine or a salt thereof, or said fourth amino acid that is 5-hydroxytryptophan, or said energy recycler comprises creatine or a salt thereof, or combinations thereof.

In some embodiments, said taurine or a salt thereof is present in said formulation, individually, in each case, in an amount of about 60 mg. In some embodiments, said DL-phenylalanine is present in said formulation in an amount of from about 10 mg to about 150 mg. In some embodiments, said L-tyrosine is present as a hydrochloric acid salt in said formulation in an amount of from about 10 mg to about 150 mg. In some embodiments, said L-arginine is present as a hydrochloric acid salt in said formulation in an amount of from about 10 mg to about 150 mg. In some embodiments, said 5-hydroxytryptophan is present in said formulation, individually, in each case, in an amount of from about 10 mg to about 50 mg. In some embodiments, said creatine that is creatine monohydrate, wherein said creatine monohydrate is present in said formulation in an amount of from about 10 mg to about 50 mg.

In another aspect, the subject matter disclosed herein comprises a method of supporting cognitive health of a human, refining clarity and concentration in a human, increasing energy and alertness in a human, strengthening mental stamina in a human, or any combination thereof, by orally administering a supplement formulation comprising one or more adaptogens, one or more first antioxidants, an agent to maintain healthy absorption of nutrients, and an agent to maintain healthy cognitive function, wherein said agent to maintain healthy cognitive function is present in said formulation, individually, in each case, in an amount of from about 0.5 mg to about 4 mg; or a second antioxidant, one or more compounds to maintain healthy cognitive performance, and a first amino acid or a salt thereof, wherein said first amino acid or a salt thereof is present in said formulation, individually, in each case, in an amount of from about 10 mg to about 400 mg; or an energy recycler, a second amino acid or a salt thereof, a third amino acid or a salt thereof, a fourth amino acid or a salt thereof, a fifth amino acid or a salt thereof, and a third antioxidant, wherein said third antioxidant is present in said formulation, individually, in each case, in an amount of from about 10 mg to about 150 mg.

In some embodiments, a method comprises orally administering a supplement formulation comprising one or more adaptogens, one or more first antioxidants, an agent to maintain healthy absorption of nutrients, and an agent to maintain healthy cognitive function, wherein said agent to maintain healthy cognitive function is present in said formulation, individually, in each case, in an amount of from about 0.5 mg to about 4 mg; and a second antioxidant, one or more compounds to maintain healthy cognitive performance, and a first amino acid or a salt thereof, wherein said first amino acid or a salt thereof is present in said formulation, individually, in each case, in an amount of from about 10 mg to about 400 mg; and an energy recycler, a second amino acid or a salt thereof, a third amino acid or a salt thereof, a fourth amino acid or a salt thereof, a fifth amino acid or a salt thereof, and a third antioxidant, wherein said third antioxidant is present in said formulation, individually, in each case, in an amount of from about 10 mg to about 150 mg.

In another aspect, the subject matter disclosed herein comprises an orally administered supplement formulation comprising a first amino acid or a salt thereof, a second amino acid or a salt thereof, an antioxidant, a precursor for a neurotransmitter, an agent to promote healthy sleep, an agent to maintain healthy cognitive function, and a compound to help maintain healthy brain function, wherein said compound to help maintain healthy brain function is present in said formulation in an amount of from about 8 mg to about 40 mg. In some embodiments, said compound to help maintain healthy brain function comprises myo-inositol, or said first amino acid is L-glutamine or a salt thereof, or said second amino acid is L-theanine, or said antioxidant comprises taurine or a salt thereof, or said precursor for a neurotransmitter comprises gamma-aminobutyric acid (GABA), or said agent to promote healthy sleep comprises melatonin or a salt thereof, or said agent to maintain healthy cognitive function comprises phosphatidylserine or a salt thereof, or any combination thereof.

In some embodiments, said myo-inositol is present in said formulation in an amount of about 16 mg. In some embodiments, said L-glutamine or a salt thereof is present in said formulation in an amount of from about 8 mg to about 50 mg. In some embodiments, said L-theanine is present in said formulation in an amount of from about 10 mg to about 300 mg. In some embodiments, said taurine or a salt thereof is present in said formulation in an amount of from about 10 mg to about 120 mg. In some embodiments, said GABA is present in said formulation in an amount of from about 10 mg to about 600 mg. In some embodiments, said melatonin or a salt thereof is present in said formulation in an amount of from about 7 mg to about 20 mg. In some embodiments, said phosphatidylserine or a salt thereof is present in said formulation in an amount of from about 0.5 mg to about 4 mg.

In another aspect, the subject matter disclosed herein comprises an orally administered supplement formulation comprising one or more compounds to promote healthy sleep, a precursor for a neurotransmitter, and an antioxidant, wherein said antioxidant is present in said formulation in an amount of from about 8 mg to about 60 mg. In some embodiments, said antioxidant comprises ashwagandha root extract, or said one or more compounds to promote healthy sleep comprise valerian root extract, or said one or more compounds to promote healthy sleep comprise chamomile flower extract, or said one or more compounds to promote healthy sleep comprise hops flower extract, or said one or more compounds to promote healthy sleep comprise passion flower extract, or said one or more compounds to promote healthy sleep comprise lemon balm leaf extract, or said precursor for a neurotransmitter comprises 5-hydroxytryptophan or a salt thereof, or any combination thereof.

In some embodiments, said ashwagandha root extract is present in said formulation in an amount of about 28 mg. In some embodiments, said valerian root extract is present in said formulation in an amount of from about 50 mg to about 300 mg. In some embodiments, said chamomile flower extract is present in said formulation in an amount of from about 10 mg to about 50 mg. In some embodiments, said hops flower extract is present in said formulation in an amount of from about 10 mg to about 50 mg. In some embodiments, said 5-hydroxytryptophan or a salt thereof is present in said formulation in an amount of from about 8 mg to about 60 mg. In some embodiments, said passion flower extract is present in said formulation in an amount of from about 8 mg to about 60 mg. In some embodiments, said lemon balm leaf extract is present in said formulation in an amount of from about 8 mg to about 60 mg.

In another aspect, the subject matter disclosed herein comprises a method of promoting sleep, supporting health, supporting well-being, helping an individual wake up feeling refreshed, or any combination thereof, by orally administering a supplement formulation comprising a first amino acid or a salt thereof, a second amino acid or a salt thereof, a first antioxidant, a first precursor for a neurotransmitter, an agent to promote healthy sleep, an agent to maintain healthy cognitive function, and a compound to help maintain healthy brain function, wherein said compound to help maintain healthy brain function is present in said formulation in an amount of from about 8 mg to about 40 mg; or one or more compounds to promote healthy sleep, a second precursor for a neurotransmitter, and a second antioxidant, wherein said second antioxidant is present in said formulation in an amount of from about 8 mg to about 60 mg.

In some embodiments, a method comprises orally administering a supplement formulation comprising a first amino acid or a salt thereof, a second amino acid or a salt thereof, a first antioxidant, a first precursor for a neurotransmitter, an agent to promote healthy sleep, an agent to maintain healthy cognitive function, a compound to help maintain healthy brain function, wherein said compound to help maintain healthy brain function is present in said formulation in an amount of from about 8 mg to about 40 mg; and one or more compounds to promote healthy sleep, a second precursor for a neurotransmitter, and a second antioxidant, wherein said second antioxidant is present in said formulation in an amount of from about 8 mg to about 60 mg.

In another aspect, the subject matter disclosed herein comprises an orally administered supplement formulation in unit dose form, comprising one or more agents to maintain healthy cognitive function, one or more ingredients to help maintain healthy memory performance, and a compound to help maintain healthy brain function, wherein said compound to help maintain healthy brain function is present in said formulation, individually, in each case, in an amount of from about 10 mg to about 160 mg. In some embodiments, said compound to help maintain healthy brain function comprises myo-inositol, or said one or more agents to maintain healthy cognitive function comprise phosphatidylcholine or a salt thereof, or said one or more agents to maintain healthy cognitive function comprise phosphatidylserine or a salt thereof, or said one or more ingredients to help maintain healthy memory performance comprise alpha-glycerophosphocholine or a salt thereof, or said one or more ingredients to help maintain healthy memory performance comprise choline (optionally as choline bitartrate, citicoline, phosphatidylcholine, and/or glycerophosphatocholine), or any combinations thereof.

In some embodiments, said myo-inositol is present in said formulation, individually, in each case, in an amount of about 80 mg. In some embodiments, said phosphatidylcholine or a salt thereof is present in said formulation, individually, in each case, in an amount of from about 10 mg to about 300 mg or about 1 to about 300 mg. In some embodiments, said phosphatidylserine or a salt thereof is present in said formulation, individually, in each case, in an amount of from about 6 mg to about 20 mg or about 1 mg to about 20 mg. In some embodiments, said alpha-glycerophosphocholine or a salt thereof is present in said formulation, individually, in each case, in an amount of from about 6 mg to about 20 mg or from about 1 mg to about 20 mg. In some embodiments, said one or more ingredients to help maintain healthy memory performance comprise choline. In some embodiments, said choline is present in said formulation, individually, in each case, in an amount of from about 10 mg to about 100 mg or about 10 to about 200 mg.

In another aspect, the subject matter disclosed herein comprises an orally administered supplement formulation in unit dose form, comprising one or more antioxidants, an amino acid or a salt thereof, one or more agents to help maintain healthy blood circulation, and a compound to help maintain healthy brain function, wherein said compound to help maintain healthy brain function is present in said formulation, individually, in each case, in an amount of from about 10 mg to about 50 mg. In some embodiments, said compound to help maintain healthy brain function comprises acetyl-L-carnitine or a salt thereof, or said one or more antioxidants comprise taurine or a salt thereof, or said one or more antioxidants comprise alpha lipoic acid or a salt thereof, or said one or more antioxidants comprise resveratrol or a salt thereof, or said one or more antioxidants comprise quercetin or a salt thereof, or said one or more antioxidants comprise astaxanthin or a salt thereof, or said one or more antioxidants comprise CoQ10, or said amino acid is L-arginine, or said one or more agents to help maintain healthy blood circulation comprise L-citrulline or a salt thereof, or said one or more agents to help maintain healthy blood circulation comprise beet root extract, or said formulation further comprises chlorophyll, or said formulation further comprises menaquinone MK7 (K2), or any combination thereof.

In some embodiments, said acetyl-L-carnitine or a salt thereof is present in said formulation, individually, in each case, in an amount of about 25 mg. In some embodiments, said taurine or a salt thereof is present in said formulation, individually, in each case, in an amount of from about 10 mg to about 80 mg. In some embodiments, said alpha lipoic acid or a salt thereof is present in said formulation, individually, in each case, in an amount of from about 10 mg to about 50 mg. In some embodiments, said resveratrol or a salt thereof is present in said formulation, individually, in each case, in an amount of from about 10 mg to about 50 mg. In some embodiments, said quercetin or a salt thereof is present in said formulation, individually, in each case, in an amount of from about 0.5 mg to about 5 mg or from about 0.5 mg to about 10 mg. In some embodiments, said astaxanthin or a salt thereof is present in said formulation, individually, in each case, in an amount of from about 0.5 mg to about 4 mg or from about 0.1 mg to about 4 mg. In some embodiments, said CoQ10 is present in said formulation, individually, in each case, in an amount of from about 0.01 mg to about 4 mg. In some embodiments, said L-arginine is present as a hydrochloric acid salt in said formulation, individually, in each case, in an amount of from about 10 mg to about 100 mg. In some embodiments, wherein said L-citrulline or a salt thereof is present in said formulation, individually, in each case, in an amount of from about 8 mg to about 80 mg. In some embodiments, said beet root extract is present in said formulation, individually, in each case, in an amount of from about 8 mg to about 80 mg. In some embodiments, said chlorophyll is present in said formulation in an amount from about 0.1 mg to about 5 mg. In some embodiments, said menaquinone MK7 (K2) is present in said formulation in an amount from about 0.001 mg to about 0.1 mg.

In another aspect, the subject matter disclosed herein comprises an orally administered supplement formulation in unit dose form, comprising one or more antioxidants, one or more adaptogens, an agent to help maintain healthy blood circulation, an agent to maintain healthy absorption of nutrients; and an agent to maintain healthy heart function, wherein said agent to maintain healthy heart function is present in said formulation, individually, in each case, in an amount of from about 10 mg to about 150 mg. In some embodiments, said one or more antioxidants comprise grape seed extract, or said one or more antioxidants comprise garlic bulb, or said one or more adaptogens comprise ginkgo leaf extract, or said one or more adaptogens comprise *ginseng* root extract, or said *ginseng* root extract is Korean *ginseng* root extract, or said agent to help maintain healthy blood circulation is turmeric root extract, or said agent to maintain healthy absorption of nutrients is cayenne pepper, or said one or more adaptogens comprise boswellia extract, or said one or more antioxidants comprise rosemary leaf extract, or said one or more antioxidants comprise ginger root extract, or the formulation further comprises citrus bioflavonoids concentrate, or said formulation further comprises omega-3 DHA and omega-3 EPA, or any combinations thereof.

In some embodiments, said grape seed extract is present in said formulation, individually, in each case, in an amount of from about 10 mg to about 50 mg. In some embodiments, said garlic bulb is present in said formulation, individually, in each case, in an amount of from about 5 mg to about 50 mg. In some embodiments, said ginkgo leaf extract is present in said formulation, individually, in each case, in an amount of from about 5 mg to about 50 mg or from about 5 mg to about 100 mg. In some embodiments, said *ginseng* root extract is present in said formulation, individually, in each case, in an amount of from about 5 mg to about 50 mg. In some embodiments, said turmeric root extract is present in said formulation, individually, in each case, in an amount of from about 10 mg to about 100 mg. In some embodiments, said cayenne pepper is present in said formulation, individually, in each case, in an amount of from about 10 mg to about 100 mg or about 5 mg to about 100 mg. In some embodiments, said boswellia extract is present in said formulation, individually, in each case, in an amount of from about 10 mg to about 50 mg. In some embodiments, said rosemary leaf extract is present in said formulation, individually, in each case, in an amount of from about 10 mg to about 50 mg. In some embodiments, said ginger root extract can be present in the formulation in an amount of from about 10 mg to about 80 mg. In some embodiments, said citrus bioflavonoids concentrate is present in the formulation in an amount from about 10 mg to about 150 mg. In some embodiments, said omega-3 DHA is present in the formulation, individually, in each case, in an amount of from about 10 mg to about 500 mg. In some embodiments, said omega-3 EPA is present in the formulation, individually, in each case, in an amount of from about 10 mg to about 200 mg In another aspect, the subject matter disclosed herein comprises a method of supporting memory and a better mood in humans, increasing energy and vitality in humans, increasing overall health and wellness in humans, promoting cognitive health in humans, or any combination thereof, comprising orally administering a supplement formation comprising one or more agents to maintain healthy cognitive function, one or more ingredients to help maintain healthy memory performance, and a first compound to help maintain healthy brain function, wherein said first compound to help maintain healthy brain function is present in said formulation, individually, in each case, in an amount of from about 10 mg to about 160 mg; or one or more first antioxidants, an amino acid or a salt thereof, one or more first agents to help maintain healthy blood circulation, and a second compound to help maintain healthy brain function, wherein said second compound to help maintain healthy brain function is present in said formulation, individually, in each case, in an amount of from about 10 mg to about 50 mg; or one or more second antioxidants, one or more adaptogens, a second agent to help maintain healthy blood circulation, an agent to maintain healthy absorption of nutrients; and an agent to maintain healthy heart function, wherein said agent to maintain healthy heart function is present in said formulation, individually, in each case, in an amount of from about 10 mg to about 150 mg.

In some embodiments, the subject matter disclosed herein comprises orally administering a supplement formulation comprising one or more agents to maintain healthy cognitive function, one or more ingredients to help maintain healthy memory performance, and a first compound to help maintain healthy brain function, wherein said first compound to help maintain healthy brain function is present in said formulation, individually, in each case, in an amount of from about 10 mg to about 160 mg; and one or more first antioxidants, an amino acid or a salt thereof, one or more first agents to help maintain healthy blood circulation, and a second compound to help maintain healthy brain function, wherein said second compound to help maintain healthy brain function is present in said formulation, individually, in each case, in an amount of from about 10 mg to about 50 mg; and one or more second antioxidants, one or more adaptogens, a second agent to help maintain healthy blood circulation, an agent to maintain healthy absorption of nutrients; and an agent to maintain healthy heart function, wherein said agent to maintain healthy heart function is present in said formulation, individually, in each case, in an amount of from about 10 mg to about 150 mg.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION

Figure 1:
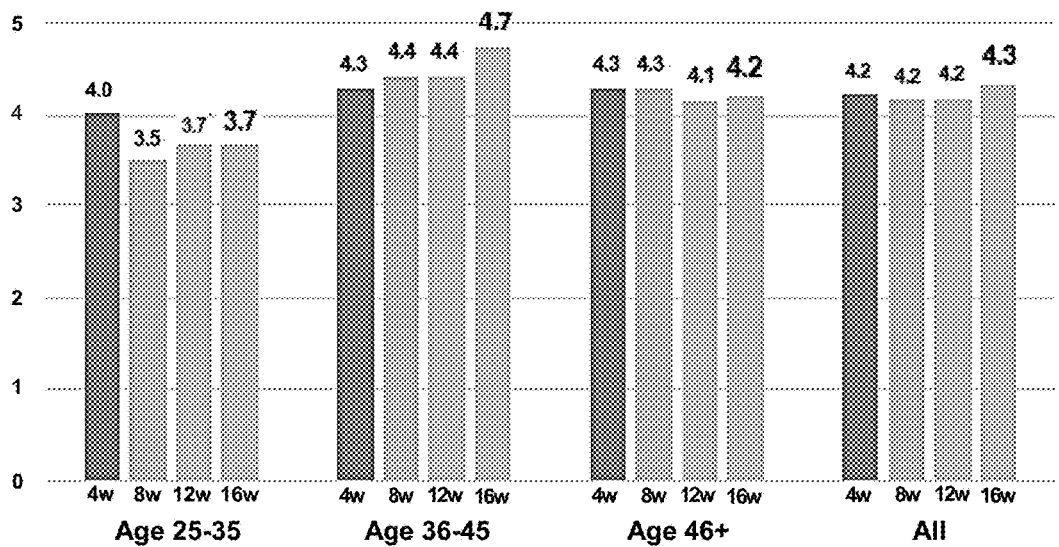
FIG. 1 shows the results of the 16-week study on the effects of category 1 formulations, category 2 formulations, and category 3 formulations on participants. The results were reported at the end of the 4-week trial, at the 8-week mark, at 12 weeks and again at 16 weeks of use.

While various embodiments of the invention have been shown and described herein, it will be obvious to those skilled in the art that such embodiments are provided by way of example only. Numerous variations, changes, and substitutions can occur to those skilled in the art without departing from the invention. It should be understood that various alternatives to the embodiments of the invention described herein can be employed. It shall be understood that different aspects of the invention can be appreciated individually, collectively, or in combination with each other.

Disclosed herein can be dietary supplement formulations and methods. These formulations and methods can be useful for helping individuals, among other things, enhance cognitive function and alertness, facilitate memory processing, support central nervous system performance and regulation, increase motivation and drive, improve focus, clarity, and concentration, increase speed of cognition and information processing, improve wakefulness and alertness, reduce anxiety and stress, increase energy levels, increase stamina or endurance, improve reaction times, enhance creativity, balance mood, enhance clarity, increase mental stamina, eliminate mental gridlock, boost speed of thought, regulate the synthesis of a number of neurotransmitters, improve brain cell function and production, increase antioxidant activity and brain blood flow, modulate pain receptors, or enhance neural growth and neuroplasticity.

The formulations of dietary supplements and methods of use thereof disclosed herein can also be useful for helping individuals, among other things, induce and maintain sleep, calm down, stabilize their mod, regulate their clock and sleep-wake cycle, facilitate memory processing, support nervous system health, promote relaxation, reduce symptoms of stress and anxiety, improve cognition and memory, improve quality of sleep, reduce time required to fall asleep, achieve deep and restful sleep, uplift mood, offset caffeine in other dietary supplements, reduce brain cell activity, result in a relaxed state, wake up feeling refreshed and enable rejuvenated mornings, optimize memory consolidation and neuroprotective processes, enhance cognition generally and the day after quality night of sleep, or feel more relaxed and balanced.

The formulations of dietary supplements and methods of use thereof disclosed herein can also be useful for helping individuals, among other things, promote learning and memory, support cognitive function, restore and stabilize cells, facilitate energy production, improve mental and emotional health, stabilize metabolism rate and mood, facilitate chemical reactions critical to health, limit stress and anxiety, improve attention and focus, improve mental performance and ability to concentrate, improve overall well-being and better energy, or support long-term brain health.

Provided herein are methods and formulations of dietary supplements that when administered to individuals, can support and/or enhance at least one of: detoxification, eyes and ears health, natural blood sugar metabolism, male reproductive health, weight control, skin, soft tissue, skeletal tissue health, natural blood sugar levels, female reproductive health, healthy blood pressure levels, male sexual function health, glutathione levels, connective tissue health, triglyceride levels, circulatory system health, homocysteine levels, musculoskeletal health, LDL levels, antioxidant health, energy levels, reproductive health, natural pH levels, natural insulin response to glucose load, healthy HDL cholesterol levels, natural stress responses, natural glutathione levels, natural growth and repair of tissues, natural biliary levels, natural glucose tolerance, adrenal function, natural insulin receptor site sensitivity, platelet function, natural recovery time, brain function and memory, natural nerve transmission, heart and cardiovascular health, natural cell division, liver health, natural breakdown of fats, insulin health, natural bone growth, natural white blood cell levels, natural tryptophan metabolism, healthy red blood cells, natural thermogenesis, small blood vessel health, natural iron and sugar utilization, health and integrity of cellular tissue, natural secretions of insulin and glucagon, the immune system health, natural nutrient utilization, metabolism health, natural absorption of minerals, cardiovascular health, natural protein synthesis, kidney health, natural production of nucleic acids, creatine phosphate, gall bladder health, natural heme production, blood circulation, muscle health, natural enzymatic reactions, bone health, healthy stress responses, oral health, methionine metabolism, joint health, maintenance of a healthy nervous system, hormone health, appetite control, digestion health, glycemic control, colon health, gene expression, menstruation health, cellular repair, scalp health, nutrient transportation, intestinal health, adrenal hormones, respiratory health, chemical reactions, healthy hair, mucous membranes, nails, and overall physical and mental well-being health. In certain embodiments, the formulations and can methods further comprise fish oils or derivatives thereof, administration of which can enhance and/or supports at least one of: heart health, cardiovascular health, immune system, natural liver function, natural hormones function, natural brain function, cell health, natural adrenal glands function, healthy cholesterol levels, normal blood pressure levels, and insulin health.

Unless defined otherwise, all technical and scientific terms used herein have the same meaning as is commonly understood by one of skill in the art to which the claimed subject matter belongs. It is to be understood that the foregoing general description and the following detailed description are exemplary and explanatory only and are not restrictive of any subject matter claimed. In this application, the use of the singular includes the plural unless specifically stated otherwise.

As used herein, "essential" means a biomolecule that the human body cannot make in sufficient amounts, and therefore, must be ingested.

In the present description, any concentration range, percentage range, ratio range, or integer range is to be understood to include the value of any integer within the recited range and, when appropriate, fractions thereof (such as one tenth and one hundredth of an integer), unless otherwise indicated. As used herein, "about" means±10% of the indicated range, value, sequence, or structure, unless otherwise indicated. It should be understood that the terms "a" and "an" as used herein refer to "one or more" of the enumerated components unless otherwise indicated or dictated by its context. The use of the alternative (e.g., "or") should be understood to mean either one, both, or any combination thereof of the alternatives. As used herein, the terms "include" and "comprise" are used synonymously. As used herein, the use of the term "derivative" should be understood to include the term "salt."

It is to be understood that the methods, formulations and compositions described herein are not limited to the particular methodology, protocols, methods, and reagents described herein and as such can vary. It is also to be understood that the terminology used herein is for the purpose of describing particular embodiments only, and is not intended to limit the scope of the methods and compositions described herein, which will be limited only by the appended claims.

Exemplary Ingredients

The methods and dietary supplement formulations described herein can comprise at least one of the ingredients discussed below. The formulations described herein can comprise a plurality of ingredients described below. Two or more ingredients can be combined in an amount suitable to provide synergistic effects. The formulations described herein can contain other active and inactive ingredients in addition to one or more ingredients described herein. Although each of the ingredients can be described under one category (vitamins or salts thereof, minerals, etc.), it is to be understood that each of these ingredients can also be categorized under more than one categories. For example, vitamin D can be categorized under vitamins or salts thereof, but it can also be categorized under antioxidants.

1. Vitamins or Salts Thereof

The ingredients can include at least 1, 2, 3, 4, 5, 6, 7, 8, 9, 10, 11, 12, 13, or more essential vitamins or salts thereof. These essential vitamins or salts thereof can include, but not limited to, vitamin A or a salt thereof, vitamin C or a salt thereof, vitamin D or a salt thereof, vitamin E or a salt thereof, vitamin K (optionally as Menaquinone MK7 (K2)) or a salt thereof and the B vitamins or salts thereof. The B vitamins or salts thereof can include thiamine or a salt thereof (vitamin B1), riboflavin or a salt thereof (vitamin B2), niacin or a salt thereof (vitamin B3), pantothenic acid or a salt thereof (vitamin B5), pyroxidine or a salt thereof (vitamin B6), biotin or a salt thereof (vitamin B7), folate or a salt thereof (vitamin B9) including levomefolic acid or a salt thereof (optionally as L-5-Methyltetahydrofolate), and cobalamin or a salt thereof (vitamin B12). Examples of some of these essential vitamins or salts thereof are discussed below.

Vitamin A: Certain methods and formulations described herein can comprise a suitable amount of vitamin A or derivative or analog thereof. Certain methods and formulations of dietary supplements can comprise vitamin A or derivative or analog thereof in an amount suitable to support and/or enhance at least one of: eye health, healthy vision, cofactors for toxin breakdown, memory processing, healthy cognitive function, homocysteine levels, moisture levels for eyes/skin/mucous membranes, antioxidant levels, heart health, and skin/soft tissue/skeletal tissue health.

Vitamin C: Certain methods and formulations described herein can comprise a suitable amount of vitamin C or derivative or analog thereof. Certain methods and formulations of dietary supplements can comprise vitamin C or derivative or analog thereof in an amount suitable to support and/or enhance at least one of: neutralization of toxins, glutathione levels, immune system, removal of heavy metal toxins, blood sugar metabolism, beta cells of the pancreas, antioxidation, neuronal function, and growth and repair of tissues.

Vitamin D: Certain methods and formulations described herein can comprise a suitable amount of vitamin D or derivative or analog thereof. Certain methods and formulations of dietary supplements can comprise vitamin D or derivative or analog thereof in an amount suitable to support and/or enhance at least one of: cognitive function, calcium regulation, blood sugar metabolism, heart and cardiovascular health, immune function, insulin receptor site activity, bone health, reducing the risk of some forms of cancer, and alleviating musculoskeletal pain.

Vitamin E: Certain methods and formulations described herein can comprise a suitable amount of vitamin E or derivative or analog thereof. Certain methods and formulations of dietary supplements can comprise vitamin E or derivative or analog thereof in an amount suitable to support and/or enhance at least one of: free radical elimination, health and integrity of cellular tissue, healthy insulin receptor site activity, triglyceride levels, LDL levels, platelet function, glycemic control, antioxidant levels, protecting brain cells, and immune function.

Vitamin K (Menaquinone MK7 (K2)): Certain methods and formulations described herein can comprise a suitable amount of vitamin K or derivative or analog thereof. Methods and formulations of dietary supplements can comprise vitamin K or derivative or analog thereof in an amount suitable to support and/or enhance at least one of: regulating calcium in brain, neuronal activity, antioxidant levels, bone health, healthy heart function, healthy cognitive function, and healthy blood circulation.

Vitamin B1: Certain methods and formulations described herein can comprise a suitable amount of vitamin B1 or derivative or analog thereof. Certain methods and formulations of dietary supplements can comprise vitamin B1 or derivative or analog thereof in an amount suitable to support and/or enhance at least one of: cofactor levels for energy production, antioxidation, neuro-protection, small blood vessel health, blood sugar metabolism, cholesterol levels, heart and cardiovascular health, and brain function and memory.

Vitamin B2: Certain methods and formulations described herein can comprise a suitable amount of vitamin B2 or derivative or analog thereof. In certain embodiments, methods and formulations of dietary supplements comprise vitamin B2 or derivative or analog thereof in an amount suitable to support and/or enhance at least one of: antioxidation, energy production, immune function, energy levels, and maintenance of healthy hair, skin, mucous membranes, and nails, reproductive function, and memory.

Niacin: Certain methods and formulations described herein can comprise a suitable amount of niacin or derivative or analog thereof. Certain methods and formulations of dietary supplements can comprise niacin or derivative or analog thereof in an amount suitable to support and/or enhance at least one of: energy production, oxidation, cholesterol levels, blood sugar metabolism, beta cells of the pancreas, adrenal function, healthy nervous system, one or more metabolic processes, memory processing, and healthy cardiovascular function.

Pantothenic Acid: Certain methods and formulations described herein can comprise a suitable amount of pantothenic acid or derivative or analog thereof. Certain methods and formulations of dietary supplements can comprise pantothenic acid or derivative or analog thereof in an amount suitable to support and/or enhance at least one of: acetylcholine, hair, mood stabilization, stress responses, heart health, immune health, joint health, adrenal hormones, formation of fats/proteins/carbohydrates/amino acids/antibiotics, healthy nervous system, balancing blood sugar, lower cholesterol level, energy production, formation of blood cells, and stamina. As used herein and throughout, "pantothenic acid," can refer to both dicalcium pantothenate and d-calcium pantothenate.

Levomefolic Acid (L-5-Methyltetahydrofolate): Certain methods and formulations described herein can comprise a suitable amount of levomefolic acid or derivative or analog thereof. Certain methods and formulations of dietary supplements can comprise levomefolic acid or derivative or analog thereof in an amount suitable to support and/or enhance at least one of: red blood cell formation, hair, mood stabilization, stress responses, heart health, immune health, joint health, adrenal hormones, formation of fats/proteins/carbohydrates/amino acids/antibiotics, healthy nervous system, balancing blood sugar, lower cholesterol level, energy production, and stamina.

Vitamin B6: Certain methods and formulations described herein can comprise a suitable amount of vitamin B6 or derivative or analog thereof. Certain methods and formulations of dietary supplements can comprise vitamin B6 or derivative or analog thereof in an amount suitable to support and/or enhance at least one of: antioxidation, energy production, homocysteine levels, blood sugar metabolism, glucose tolerance, secretions of insulin and glucagon, tryptophan metabolism, memory, and neuro-protection.

Biotin: Certain methods and formulations described herein can comprise a suitable amount of biotin or derivative or analog thereof. Certain methods and formulations of dietary supplements can comprise biotin or derivative or analog thereof in an amount suitable to support and/or enhance at least one of: energy production, blood sugar control, cholesterol levels, insulin response to glucose load, manufacture and utilization of carbohydrates/fats/amino acids, maintenance of insulin receptor site sensitivity, glucokinase activity, hair growth, nail health, and metabolism.

Vitamin B9: Certain methods and formulations described herein can comprise a suitable amount of vitamin B9 or derivative or analog thereof. Certain methods and formulations of dietary supplements can comprise vitamin B9 or derivative or analog thereof in an amount suitable to support and/or enhance at least one of: healthy blood circulation, healthy red blood cells, energy production, healthy brain function, healthy immune system, bone strength, fertility, emotional healthy, mental health, and vision.

Vitamin B12: Certain methods and formulations described herein can comprise a suitable amount of vitamin B12 or derivative or analog thereof. Certain methods and formulations of dietary supplements can comprise vitamin B12 or derivative or analog thereof in an amount suitable to support and/or enhance at least one of: healthy homocysteine levels, healthy red blood cells, energy production, immune system, healthy cognitive function, memory processing, and neuro-protection.

2. Minerals

The ingredients can include at least about 1, 2, 3, 4, 5, 6, 7, 8, 9, 10, 11, 12, 13, 14, 15, 16, or more essential minerals. These essential minerals can comprise, but not limited to, calcium, zinc, potassium, chlorine, magnesium, phosphorous, sodium, chromium, copper, fluoride, iodine, iron, molybdenum, selenium, manganese, and sulphur. Examples of some of these essential minerals are discussed below.

Magnesium: Certain methods and formulations described herein can comprise a suitable amount of magnesium or derivative or analog thereof. Certain methods and formulations of dietary supplements can comprise magnesium or derivative or analog thereof in an amount suitable to support and/or enhance at least one of: mood stabilization, muscle health, blood pressure, cardiovascular system, bone health, metabolism, blood sugar levels, insulin receptor site sensitivity, cholesterol levels, cognitive function, regulating neurotransmitters, regulating hormone melatonin, energy production, and platelet activity. As used herein and throughout, "magnesium," can refer to both magnesium oxide and magnesium aspartate.

Zinc: Certain methods and formulations described herein can comprise a suitable amount of zinc or derivative or analog thereof. Certain methods and formulations of dietary supplements can comprise zinc or derivative or analog thereof in an amount suitable to support and/or enhance at least one of: immune function, cell division, hormone levels, antioxidation, healthy stress responses, red blood cells, white blood cells, male reproductive health, female reproductive health, cardiovascular system, blood sugar metabolism, brain health, cholesterol stabilization, energy production, and mood stabilization. As used herein and throughout, "zinc," can refer to both zinc oxide or an a zinc amino acid chelate.

Calcium: Certain methods and formulations described herein can comprise a suitable amount of calcium or derivative or analog thereof. Certain methods and formulations of dietary supplements can comprise calcium or derivative or analog thereof in an amount suitable to support and/or enhance at least one of: bone health, nerve transmission, blood sugar metabolism, oral health, weight regulation, colon health, muscle health, heart health, blood pressure, joint health, kidney health, pH level, healthy sleep, balancing hormone, and nutrient transportation. As used herein and throughout, "calcium," can refer to both calcium carbonate and d-calcium pantothenate.

Selenium: Certain methods and formulations described herein can comprise a suitable amount of selenium or derivative or analog thereof. Certain methods and formulations of dietary supplements can comprise selenium or derivative or analog thereof in an amount suitable to support and/or enhance at least one of: thyroid health, DNA synthesis, immune function, reproduction, blood sugar metabolism, antioxidation, healthy brain function, healthy cognitive function, memory processing, and bone growth.

Phosphorus: Certain methods and formulations described herein can comprise a suitable amount of phosphorous or derivative or analog thereof. Certain methods and formulations of dietary supplements can comprise phosphorus or derivative or analog thereof in an amount suitable to support and/or enhance at least one of: bone health, digestion, hormones, energy, cellular repair, chemical reactions, proper nutrient utilization, kidneys, brain support, and protein formation.

Copper: Certain methods and formulations described herein can comprise a suitable amount of copper or derivative or analog thereof. Certain methods and formulations of dietary supplements can comprise copper or derivative or analog thereof in an amount suitable to support and/or enhance at least one of: joint health, proper growth, connective tissues, brain, enzymatic reactions, iron and sugar utilization, energy production, thyroid health, red blood cell formation, immune system, healthy cognitive function, and memory processing.

Manganese: Certain methods and formulations described herein can comprise a suitable amount of manganese or derivative or analog thereof. Certain methods and formulations of dietary supplements can comprise manganese or derivative or analog thereof in an amount suitable to support and/or enhance at least one of: GABA, bones, antioxidation, blood sugar metabolism, overall metabolism, regulating calcium and glucose level, energy production, healthy cognitive function, healthy memory, inflammation alleviation, thyroid, absorption, brain, nervous system, and digestion.

Molybdenum: Certain methods and formulations described herein can comprise a suitable amount of molybdenum or derivative or analog thereof. Certain methods and formulations of dietary supplements can comprise molybdenum or derivative or analog thereof in an amount suitable to support and/or enhance at least one of: uric acid stabilization, sulfation, enzyme levels, inflammation alleviation, regulating copper, and detoxification.

Iron: Certain methods and formulations described herein can comprise a suitable amount of iron or derivative or analog thereof. Certain methods and formulations of dietary supplements can comprise iron or derivative or analog thereof in an amount suitable to support and/or enhance at least one of: energy production, healthy cognitive function, healthy brain function, memory processing, cardiovascular system, and healthy blood circulation.

Iodine: Certain methods and formulations described herein can comprise a suitable amount of iodine or derivative or analog thereof. Certain methods and formulations of dietary supplements can comprise iodine or derivative or analog thereof in an amount suitable to support and/or enhance at least one of: stabilizing metabolism rate, healthy mood, healthy brain function, and brain development.

Chromium: Certain methods and formulations described herein can comprise a suitable amount of chromium or derivative or analog thereof. Certain methods and formulations of dietary supplements can comprise chromium or derivative or analog thereof in an amount suitable to support and/or enhance at least one of: stabilizing glucose metabolism, healthy brain function, healthy cognitive function, and memory.

Potassium: Certain methods and formulations described herein can comprise a suitable amount of potassium or derivative or analog thereof. Certain methods and formulations of dietary supplements can comprise potassium or derivative or analog thereof in an amount suitable to support and/or enhance at least one of: nerve transmission, blood sugar metabolism, oral health, weight regulation, muscle health, heart health, kidney health, pH level, healthy sleep, balancing hormone, and nutrient transportation.

3. Adaptogens

The ingredients can include one or more adaptogens. Adaptogens can greatly improve individual's ability to adapt to stress, whether it's a hectic schedule, heat or cold, noise, high altitudes or any number of other stressors. Adaptogens can impart strength, energy, stamina, endurance, and they improve mental clarity. Adaptogens can include, but not limited to, ashwagandha root, boswellia, eleuthero, holy basil (Tulsi), maca, *ginseng* root, *rhodiola* root, schisandra, *astragalus*, licorice, moringa, ginkgo leaf, and gotu kola. Examples of some of the adaptogens are discussed below.

*Ginseng* root: Certain methods and formulations described herein can comprise a suitable amount of *ginseng* root or extract or derivative or analog thereof. Certain methods and formulations of dietary supplements can comprise *ginseng* root or extract or derivative or analog thereof in an amount suitable to support and/or enhance at least one of: antioxidation, healthy nervous system, healthy mood, heart health, liver health, kidney health, healthy cognitive function, immune function, carbohydrate absorption by the intestines, blood sugar metabolism, insulin production, menstruation, weight control, physical and mental well-being, and male sexual function.

Ginkgo leaf: Certain methods and formulations described herein can comprise a suitable amount of ginko leaf or extract or derivative or analog thereof. Certain methods and formulations of dietary supplements can comprise ginko leaf or extract or derivative or analog thereof in an amount suitable to support and/or enhance at least one of: boosting neurotransmitters, platelet function, reducing free radicals, memory, blood flow to the brain, oxygen utilization, vision, eyes, healthy cognitive function, and mood stabilization.

Boswellia: Certain methods and formulations described herein can comprise a suitable amount of boswellia or extract or derivative or analog thereof. Certain methods and formulations of dietary supplements can comprise boswellia or extract or derivative or analog thereof in an amount suitable to support and/or enhance at least one of: inflammation reduction, dental health, healthy cognitive function, liver health, immune system, blood sugar metabolism, and healthy brain function.

4. Antioxidant

The ingredients can include one or more antioxidants. Antioxidants can be man-made or natural substances that can prevent or delay some types of cell damage. Antioxidant can include one or more botanical antioxidants. Antioxidant can include, but not limited to, acai berries, alpha lipoic acid, astaxanthin, ashwagandha root, beta carotene, bilberry, blueberries, boswellia, CoQ-10, cucurmin, cysteine, blutathione, grape seed, green tea leaf, ginger root, garlic bulb, hydrogen peroxide, mangosteen, melatonin, oligomeric proanthocyanidins, olive leaf, optionally soy bean, polycosanol, pychnogenol, taurine, quercetin, resveratrol, and rosemary leaf. Examples of some of the antioxidants are discussed below.

Green tea leaf: Certain methods and formulations described herein can comprise a suitable amount of green tea leaf or extract or derivative or analog thereof. Certain methods and formulations of dietary supplements can comprise green tea leaf or extract or derivative or analog thereof in an amount suitable to support and/or enhance at least one of: reduction of atherosclerosis and risk of heart disease, antioxidation, lower blood pressure, reduction of cholesterol levels, healthy bone, and healthy cognitive function.

Ginger root: Certain methods and formulations described herein can comprise a suitable amount of ginger root or extract or derivative or analog thereof. Certain methods and formulations of dietary supplements can comprise ginger root or extract or derivative or analog thereof in an amount suitable to support and/or enhance at least one of: bile secretion, liver cholesterol levels, inflammation alleviation, antioxidation, blood sugar metabolism, cholesterol management, insulin levels, insulin sensitivity, digestion, heart health, healthy cognitive function, and weight management.

Bioflavonoids (Citrus): Certain methods and formulations described herein can comprise a suitable amount of citrus bioflavonoids concentrate or derivatives or analogs thereof. Certain methods and formulations of dietary supplements can comprise citrus bioflavonoids concentrate or derivatives or analogs thereof in an amount suitable to support and/or enhance at least one of: bile secretion, liver cholesterol levels, inflammation alleviation, antioxidation, blood sugar metabolism, cholesterol management, insulin levels, insulin sensitivity, digestion, heart health, healthy cognitive function, and weight management.

Resveratrol: Certain methods and formulations described herein can comprise a suitable amount of resveratrol or derivative or analog thereof. Certain methods and formulations of dietary supplements can comprise resveratrol or derivative or analog thereof in an amount suitable to support and/or enhance at least one of: inflammatory reduction, antioxidation, healthy blood circulation, reduction of oxidative stress, healthy mental function, and healthy muscle.

Taurine: Certain methods and formulations described herein can comprise a suitable amount of taurine or derivative or analog thereof. Certain methods and formulations of dietary supplements can comprise taurine or derivative or analog thereof in an amount suitable to support and/or enhance at least one of: healthy heart function, antioxidation, healthy cholesterol level, healthy vision, healthy muscle, healthy cognitive function, and healthy skin.

Ashwagandha root: Certain methods and formulations described herein can comprise a suitable amount of ashwagandha root or extract or derivative or analog thereof. Certain methods and formulations of dietary supplements can comprise ashwagandha root or extract or derivative or analog thereof in an amount suitable to support and/or enhance at least one of: antioxidation, healthy cognitive function, blood sugar metabolism, heart health, stress reduction, memory, nerve function, and brain function.

Quercetin: Certain methods and formulations described herein can comprise a suitable amount of quercetin or derivative or analog thereof. Certain methods and formulations of dietary supplements can comprise quercetin or derivative or analog thereof in an amount suitable to support and/or enhance at least one of: healthy brain function, healthy immune system, healthy heart function, healthy blood circulation, antioxidation, pain reducer, healthy cognitive function, and healthy cholesterol level.

Astaxanthin: Certain methods and formulations described herein can comprise a suitable amount of astaxanthin or derivative or analog thereof. Certain methods and formulations of dietary supplements can comprise astaxanthin or derivative or analog thereof in an amount suitable to support and/or enhance at least one of: healthy nerve system, healthy immune system, healthy heart function, healthy blood circulation, healthy vision, and healthy cholesterol level.

CoQ10: Certain methods and formulations described herein can comprise a suitable amount of CoQ10 or derivative or analog thereof. Certain methods and formulations of dietary supplements can comprise CoQ10 or derivative or analog thereof in an amount suitable to support and/or enhance at least one of: healthy nerve system, energy production, healthy heart function, healthy cognitive function, and healthy blood circulation.

Rosemary leaf: Certain methods and formulations described herein can comprise a suitable amount of rosemary leaf or extract or derivative or analog thereof. Certain methods and formulations of dietary supplements can comprise rosemary leaf or extract or derivative or analog thereof in an amount suitable to support and/or enhance at least one of: healthy nerve system, and healthy cognitive function.

Alpha lipoic acid: Certain methods and formulations described herein can comprise a suitable amount of alpha lipoic acid or derivative or analog thereof. Certain methods and formulations of dietary supplements can comprise alpha lipoic acid or derivative or analog thereof in an amount suitable to support and/or enhance at least one of: energy production, healthy nerve system, memory, and healthy cognitive function.

Grape seed: Certain methods and formulations described herein can comprise a suitable amount of grape seed or extract or derivative or analog thereof. Certain methods and formulations of dietary supplements can comprise grape seed or extract or derivative or analog thereof in an amount suitable to support and/or enhance at least one of: antioxidation, lower blood pressure, reduction of cholesterol levels, healthy bone, and healthy cognitive function.

5. Amino Acids or Salts Thereof

The ingredients can include one or more amino acids or salts thereof. Amino acids or salts thereof can include, but not limited to, L-theanine or a salt thereof, DL-phenylalanine or a salt thereof, L-tyrosine or a salt thereof, L-arginine or a salt thereof, 5-hydroxytryptophan or a salt thereof, and gamma aminobutyric acid (GABA) or a salt thereof. Examples of some of the amino acids or salts thereof are discussed below.

L-theanine: Certain methods and formulations described herein can comprise a suitable amount of L-theanine or derivative or analog thereof. Certain methods and formulations of dietary supplements can comprise L-theanine or derivative or analog thereof in an amount suitable to support and/or enhance at least one of: stress reduction, healthy sleep, obesity management, heart health, immunity health, stomach health, mood stabilization, and brain function.

5-hydroxytryptophan (5-HTP): Certain methods and formulations described herein can comprise a suitable amount of 5-HTP or derivative or analog thereof. Certain methods and formulations of dietary supplements can comprise 5-HTP or derivative or analog thereof in an amount suitable to support and/or enhance at least one of: memory, healthy sleep, healthy brain function, forming neurotransmitters, and healthy mood.

Gamma aminobutyric acid (GABA): Certain methods and formulations described herein can comprise a suitable amount of GABA or derivative or analog thereof. Certain methods and formulations of dietary supplements can comprise GABA or derivative or analog thereof in an amount suitable to support and/or enhance at least one of: healthy nerve system, healthy immune system, healthy brain function, mood, stress reduction, and calming nerves before performing in front of an audience.

DL-phenylalanine: Certain methods and formulations described herein can comprise a suitable amount of DL-phenylalanine or derivative or analog thereof. Certain methods and formulations of dietary supplements can comprise DL-phenylalanine or derivative or analog thereof in an amount suitable to support and/or enhance at least one of: memory, pain releaser, healthy cognitive function, healthy appetite, healthy energy levels, healthy sleep cycles, and mood.

L-tyrosine: Certain methods and formulations described herein can comprise a suitable amount of L-tyrosine or derivative or analog thereof. Certain methods and formulations of dietary supplements can comprise L-tyrosine or derivative or analog thereof in an amount suitable to support and/or enhance at least one of: memory, stress reduction, healthy appetite, healthy energy levels, healthy sleep cycles and mood, healthy brain cognitive function, and healthy nerve system.

L-arginine: Certain methods and formulations described herein can comprise a suitable amount of L-arginine or derivative or analog thereof. Certain methods and formulations of dietary supplements can comprise L-arginine or derivative or analog thereof in an amount suitable to support and/or enhance at least one of: healthy appetite, healthy energy levels, healthy sleep cycles and mood, healthy brain cognitive function, and healthy blood circulation.

6. Additional Ingredients

The ingredients can include one or more additional ingredients. The additional ingredients can comprise an agent to maintain healthy absorption of nutrients. The additional ingredients can comprise an agent to maintain healthy cognitive function. The additional ingredients can comprise one or more ingredients to help maintain healthy memory performance. The additional ingredients can comprise one or more compounds to maintain healthy cognitive performance. The additional ingredients can comprise an energy recycler. The additional ingredients can comprise one or more compounds to promote or encourage healthy sleep. The additional ingredients can comprise one or more precursors for neurotransmitters. The additional ingredients can comprise one or more agents to help maintain healthy blood circulation. The additional ingredients can comprise one or more compounds to help maintain healthy brain function. The one or more ingredients can comprise an agent to maintain healthy heart function. The additional ingredients can comprise, but not limited to, fish oil, Omega-3 DHA, Omega-3 EPA, *rhodiola* root, cayenne pepper, bacopa leaf, dimethylaminoethanol, pyrroloquinoline quinone, optionally huperzine A, creatine, L-glutamine, melatonin, phosphatidylserine, valerian root, chamomile flower, hops flower, passion flower, lemon balm leaf, phosphatidylcholine, myo-inositol, choline, optionally soy lecithin, alpha-glycerophosphocholine, optionally citicoline, L-carnitine, L-citrulline, beet root, acetyl-L-carnitine, optionally soybean oil, optionally flax seed oil, and turmeric root. It is to be understood that each of these additional ingredients can be categorized under previous 5 categories. For embodiments, *rhodiola* root can also be categorized under adaptogens. Examples of some of the additional ingredients are discussed below.

*Rhodiola* root: Certain methods and formulations described herein can comprise a suitable amount of *rhodiola* root or extract or derivative or analog thereof. Certain methods and formulations of dietary supplements can comprise *rhodiola* root or extract or derivative or analog thereof in an amount suitable to support and/or enhance at least one of: healthy cognitive performance, central nervous system, mood stabilization, heart health, cardiovascular health, stress reduction, immune system, cognitive function, and mental energy.

Cayenne pepper: Certain methods and formulations described herein can comprise a suitable amount of cayenne pepper or extract or derivative or analog thereof. Certain methods and formulations of dietary supplements can comprise cayenne pepper or extract or derivative or analog thereof in an amount suitable to support and/or enhance at least one of: healthy absorption of nutrients, pain reducer, stress reducer, and immune system.

Bacopa leaf: Certain methods and formulations described herein can comprise a suitable amount of bacopa leaf or extract or derivative or analog thereof. Certain methods and formulations of dietary supplements can comprise bacopa leaf or extract or derivative or analog thereof in an amount suitable to support and/or enhance at least one of: central nervous system, mood stabilization, heart health, stress reduction, cognitive function, and mental energy.

Dimethylaminoethanol: Certain methods and formulations described herein can comprise a suitable amount of dimethylaminoethanol or derivative or analog thereof. Certain methods and formulations of dietary supplements can comprise dimethylaminoethanol or derivative or analog thereof in an amount suitable to support and/or enhance at least one of: neuronal cell structure, healthy cognitive function, healthy brain function, and healthy mood.

Pyrroloquinoline quinone: Certain methods and formulations described herein can comprise a suitable amount of pyrroloquinoline quinone or derivative or analog thereof. Certain methods and formulations of dietary supplements can comprise pyrroloquinoline quinone or derivative or analog thereof in an amount suitable to support and/or enhance at least one of: neural growth, healthy cognitive function, healthy brain and mental function, and energy production.

Huperzine A: Certain methods and formulations described herein can comprise a suitable amount of huperzine A or derivative or analog thereof. Certain methods and formulations of dietary supplements can comprise huperzine A or derivative or analog thereof in an amount suitable to support and/or enhance at least one of: neurological repair, healthy cognitive performance, and healthy brain function.

Creatine: Certain methods and formulations described herein can comprise a suitable amount of creatine or derivative or analog thereof. Certain methods and formulations of dietary supplements can comprise creatine or derivative or analog thereof in an amount suitable to support and/or enhance at least one of: memory, healthy brain function, energy production, energy recycling, healthy cognitive function, and hormone balance.

Melatonin: Certain methods and formulations described herein can comprise a suitable amount of melatonin or derivative or analog thereof. Certain methods and formulations of dietary supplements can comprise melatonin or derivative or analog thereof in an amount suitable to support and/or enhance at least one of: healthy sleep, healthy brain function, healthy cognitive function, and hormone balance.

L-glutamine: Certain methods and formulations described herein can comprise a suitable amount of L-glutamine or derivative or analog thereof. Certain methods and formulations of dietary supplements can comprise L-glutamine or derivative or analog thereof in an amount suitable to support and/or enhance at least one of: healthy cognitive function, neural plasticity, forming neurotransmitters, sulfation, methylation, detoxification, glutathione storage, oxidative stress management, and small intestine health.

Phosphatidylserine: Certain methods and formulations described herein can comprise a suitable amount of phosphatidylserine or derivative or analog thereof. Certain methods and formulations of dietary supplements can comprise phosphatidylserine or derivative or analog thereof in an amount suitable to support and/or enhance at least one of: cellular chemical signaling, healthy cognitive function, brain health, stress alleviation, cortisol levels, mood, memory, and sleep.

Phosphatidylcholine: Certain methods and formulations described herein can comprise a suitable amount of phosphatidylcholine or derivative or analog thereof. Certain methods and formulations of dietary supplements can comprise phosphatidylcholine or derivative or analog thereof in an amount suitable to support and/or enhance at least one of: memory, liver health, healthy cognitive function, brain health, fat breakdown, inflammation reduction, and brain development.

Valerian root: Certain methods and formulations described herein can comprise a suitable amount of valerian root or extract or derivative or analog thereof. Certain methods and formulations of dietary supplements can comprise valerian root or extract or derivative or analog thereof in an amount suitable to support and/or enhance at least one of: stress reduction, healthy sleep, and healthy mood.

Chamomile flower: Certain methods and formulations described herein can comprise a suitable amount of chamomile flower or extract or derivative or analog thereof. Certain methods and formulations of dietary supplements can comprise chamomile flower or extract or derivative or analog thereof in an amount suitable to support and/or enhance at least one of: stress reduction, healthy sleep, and healthy mood.

Hops flower: Certain methods and formulations described herein can comprise a suitable amount of chamomile flower or extract or derivative or analog thereof. Certain methods and formulations of dietary supplements can comprise chamomile flower or extract or derivative or analog thereof in an amount suitable to support and/or enhance at least one of: stress reduction, healthy sleep, and healthy mood.

Passion flower: Certain methods and formulations described herein can comprise a suitable amount of passion flower or extract or derivative or analog thereof. Certain methods and formulations of dietary supplements can comprise passion flower or extract or derivative or analog thereof in an amount suitable to support and/or enhance at least one of: stress reduction, healthy sleep, and healthy mood.

Lemon balm leaf: Certain methods and formulations described herein can comprise a suitable amount of lemon balm leaf or extract or derivative or analog thereof. Certain methods and formulations of dietary supplements can comprise lemon balm leaf or extract or derivative or analog thereof in an amount suitable to support and/or enhance at least one of: healthy sleep, memory, stress reducer, healthy brain function, and healthy mood.

Myo-inositol: Certain methods and formulations described herein can comprise a suitable amount of myo-inositol or derivative or analog thereof. Certain methods and formulations of dietary supplements can comprise myo-inositol or derivative or analog thereof in an amount suitable to support and/or enhance at least one of: healthy female fertility, restoring insulin sensitivity, healthy appetite, stress reduction, healthy sleep, healthy brain function, and healthy mood.

Choline: Certain methods and formulations described herein can comprise a suitable amount of choline or derivative or analog thereof. Certain methods and formulations of dietary supplements can comprise choline or derivative or analog thereof in an amount suitable to support and/or enhance at least one of: liver function, moods, healthy memory performance, endurance, and cholesterol levels. As used herein and throughout, "choline" includes, and is not limited to, choline bitartrate, citicoline, phosphatidylcholine, and glycerophosphatocholine. Certain methods and formulations described herein can comprise a suitable amount of citicoline or derivative or analog thereof. Certain methods and formulations of dietary supplements can comprise citicoline or derivative or analog thereof in an amount suitable to support and/or enhance at least one of: energy production, healthy memory performance, and healthy brain function. "Glycerophosphatocholine" includes, but is not limited to, alpha-glycerophosphocholine. Certain methods and formulations described herein can comprise a suitable amount of alpha-glycerophosphocholine or derivative or analog thereof. Certain methods and formulations of dietary supplements can comprise alpha-glycerophosphocholine or derivative or analog thereof in an amount suitable to support and/or enhance at least one of: healthy brain function, healthy memory performance, and healthy cognitive function.

Lecithin: Certain methods and formulations described herein can comprise a suitable amount of lecithin or derivative or analog thereof. Certain methods and formulations of dietary supplements can comprise lecithin or derivative or analog thereof in an amount suitable to support and/or enhance at least one of: healthy cognitive function, biliary system, lipids, nervous system, circulatory system, metabolism, heart health, and memory.

L-carnitine: Certain methods and formulations described herein can comprise a suitable amount of L-carnitine or derivative or analog thereof. Certain methods and formulations of dietary supplements can comprise L-carnitine or derivative or analog thereof in an amount suitable to support and/or enhance at least one of: heart health, cardiovascular system, fat burning, brain, fatty liver alleviation, insulin sensitivity, blood sugar metabolism, neuroprotection, and cholesterol maintenance.

L-citrulline: Certain methods and formulations described herein can comprise a suitable amount of L-citrulline or derivative or analog thereof. Certain methods and formulations of dietary supplements can comprise L-citrulline or derivative or analog thereof in an amount suitable to support and/or enhance at least one of: healthy cognitive function, healthy blood circulation, and healthy brain function.

Acetyl-L-carnitine: Certain methods and formulations described herein can comprise a suitable amount of acetyl-L-carnitine or derivative or analog thereof. Certain methods and formulations of dietary supplements can comprise acetyl-L-carnitine or derivative or analog thereof in an amount suitable to support and/or enhance at least one of: energy production, memory, healthy brain function, healthy heart, and healthy mood.

Beet root: Certain methods and formulations described herein can comprise a suitable amount of beet root or extract or derivative or analog thereof. Certain methods and formulations of dietary supplements can comprise beet root or extract or derivative or analog thereof in an amount suitable to support and/or enhance at least one of: healthy cognitive function, blood pressure, stamina, inflammation management, and detoxification.

Turmeric root: Certain methods and formulations described herein can comprise a suitable amount of turmeric root or extract or derivative or analog thereof. Certain methods and formulations of dietary supplements can comprise turmeric root or extract or derivative or analog thereof in an amount suitable to support and/or enhance at least one of: healthy mood, healthy blood circulation, and healthy cognitive function.

Omega-3 DHA: Certain methods and formulations described herein can comprise a suitable amount of Omega-3 DHA or derivative or analog thereof. Certain methods and formulations of dietary supplements can comprise Omega-3 DHA or derivative or analog thereof in an amount suitable to support and/or enhance at least one of: cell structure, neuronal structure and function, memory, and healthy cognitive function.

Omega-3 EPA: Certain methods and formulations described herein can comprise a suitable amount of Omega-3 EPA or derivative or analog thereof. Certain methods and formulations of dietary supplements can comprise Omega-3 EPA or derivative or analog thereof in an amount suitable to support and/or enhance at least one of: cell structure, neuronal structure and function, memory, and healthy cognitive function.

Any ingredient or its salt thereof can be present in the formulation in any form, individually, in each case, in an amount of from about 0.001 mg to about 1 mg, from about 0.001 to about 2 mg, from about 0.001 mg to about 3 mg, from about 0.001 mg to about 4 mg, from about 0.001 to about 5 mg, from about 0.001 mg to about 6 mg, from about 0.001 mg to about 7 mg, from about 0.001 to about 8 mg, from about 0.001 mg to about 9 mg, from 0.001 mg to about 10 mg, from about 0.001 to about 20 mg, from about 0.001 mg to about 30 mg, from about 0.001 mg to about 40 mg, from about 0.001 to about 50 mg, from 0.001 mg to about 60 mg, from about 0.001 mg to about 70 mg, from about 0.001 to about 80 mg, from about 0.001 mg to about 90 mg, from about 0.001 mg to about 100 mg, from about 0.001 to about 200 mg, from about 0.001 mg to about 300 mg, from about 0.001 mg to about 400 mg, from about 0.001 to about 500 mg, from about 0.001 mg to about 600 mg, from about 0.001 mg to about 700 mg, from about 0.001 to about 800 mg, from about 0.001 mg to about 900 mg, from about 0.001 to about 1000 mg, from about 0.001 mg to about 2000 mg, from about 0.001 mg to about 3000 mg, from about 0.001 to about 4000 mg, from about 0.001 mg to about 5000 mg, from about 0.001 mg to about 6000 mg, from about 0.001 to about 7000 mg, from about 0.001 mg to about 8000 mg, and from about 0.001 mg to about 8000 mg.

Any ingredient or its salt thereof can be present in the formulation in any form, individually, in each case, in an amount of at least about 0.001 mg, about 0.01 mg, about 0.1 mg, about 0.2 mg, about 0.3 mg, about 0.4 mg, about 0.5 mg, about 0.6 mg, about 0.7 mg, about 0.8 mg, about 0.9 mg, about 1 mg, about 2 mg, about 3 mg, about 4 mg, about 5 mg, about 6 mg, about 7 mg, about 8 mg, about 9 mg, about 10 mg, about 11 mg, about 12 mg, about 13 mg, about 14 mg, about 15 mg, about 16 mg, about 17 mg, about 18 mg, about 19 mg, about 20 mg, about 21 mg, about 22 mg, about 23 mg, about 24 mg, about 25 mg, about 26 mg, about 27 mg, about 28 mg, about 29 mg, about 30 mg, about 31 mg, about 32 mg, about 33 mg, about 34 mg, about 35 mg, about 36 mg, about 37 mg, about 38 mg, about 39 mg, about 40 mg, about 41 mg, about 42 mg, about 43 mg, about 44 mg, about 45 mg, about 46 mg, about 47 mg, about 48 mg, about 49 mg, about 50 mg, about 51 mg, about 52 mg, about 53 mg, about 54 mg, about 55 mg, about 56 mg, about 57 mg, about 58 mg, about 59 mg, about 60 mg, about 61 mg, about 62 mg, about 63 mg, about 64 mg, about 65 mg, about 66 mg, about 67 mg, about 68 mg, about 69 mg, about 70 mg, about 80 mg, about 90 mg, about 100 mg, about 110 mg, about 120 mg, about 130 mg, about 140 mg, about 150 mg, about 160 mg, about 170 mg, about 180 mg, about 190 mg, about 200 mg, about 210 mg, about 220 mg, about 230 mg, about 240 mg, about 250 mg, about 260 mg, about 270 mg, about 280 mg, about 290 mg, about 300 mg, about 310 mg, about 320 mg, about 330 mg, about 340 mg, about 350 mg, about 360 mg, about 370 mg, about 380 mg, about 390 mg, about 400 mg, about 410 mg, about 420 mg, about 430 mg, about 440 mg, about 450 mg, about 460 mg, about 470 mg, about 480 mg, about 490 mg, about 500 mg, about 510 mg, about 520 mg, about 530 mg, about 540 mg, about 550 mg, about 560 mg, about 570 mg, about 580 mg, about 590 mg, about 600 mg, about 700 mg, about 800 mg, about 900 mg, about 1000 mg, about 2000 mg, about 3000 mg, about 4000 mg, about 5000 mg, about 6000 mg, about 7000 mg, about 8000 mg, or greater.

Exemplary Formulations

1. Formulations: Category 1

Disclosed herein are dietary supplement formulations and methods. These formulations and methods can be useful for helping individuals, among other things, enhance cognitive function and alertness, facilitate memory processing, support central nervous system performance and regulation, increase motivation and drive, improve focus, clarity, and concentration, increase speed of cognition and information processing, improve wakefulness and alertness, reduce anxiety and stress, increase energy levels, increase stamina or endurance, improve reaction times, enhance creativity, balance mood, enhance clarity, increase mental stamina, eliminate mental gridlock, boost speed of thought, regulate the synthesis of a number of neurotransmitters, improve brain cell function and production, increase antioxidant activity and brain blood flow, modulate pain receptors, and enhance neural growth and neuroplasticity.

In an aspect, an orally administered supplement formulation in unit dose form can comprise one or more adaptogens, one or more antioxidants, an agent to maintain healthy absorption of nutrients, and an agent to maintain healthy cognitive function, wherein the agent to maintain healthy cognitive function can be present in the formulation, individually, in each case, in an amount of from about 0.5 mg to about 4 mg. The one or more adaptogens can include, but not limited to, ashwagandha root extract, boswellia extract, eleuthero, holy basil (Tulsi), maca, ginseng root, rhodiola root extract, schisandra, astragalus, licorice, moringa, ginkgo root extract, and gotu kola. The one or more antioxidants can include, but not limited to acai berries, alpha lipoic acid, astaxanthin, ashwagandha root extract, beta carotene, bilberry, blueberries, boswellia extract, CoQ-10, cucurmin, cysteine, blutathione, grape seed extract, green tea leaf extract, ginger root, garlic bulb, hydrogen peroxide, mangosteen, melatonin, oligomeric proanthocyanidins, olive leaf, soy bean, polycosanol, pychnogenol, taurine, quercetin, resveratrol, and rosemary leaf extract. The agent to maintain healthy cognitive function can include bacopa leaf extract, rhodiola root extract, optionally huperzine A or a salt thereof, phosphatidylserine or a salt thereof, phosphatidylcholine or a salt thereof, and optionally soy lecithin or a salt thereof. The orally administered supplement can further comprise one or more vitamins or salts thereof. These vitamins or salts thereof can include, but not limited to, vitamin A or a salt thereof (optionally as retinyl acetate and beta carotene), vitamin C or a salt thereof (optionally as ascorbic acid), vitamin D or a salt thereof (optionally as cholecalciferol), vitamin E or a salt thereof (optionally as d-alpha tocopheryl succinate), vitamin K or a salt thereof (optionally as phytonadione (K1)), and the B vitamins or salts thereof. The B vitamins or salts thereof can include thiamine or a salt thereof (vitamin B1), riboflavin or a salt thereof (vitamin B2), niacin or a salt thereof (vitamin B3), pantothenic acid or a salt thereof (vitamin B5), pyroxidine or a salt thereof including pyridoxyl 5 phosphate (vitamin B6), biotin or a salt thereof (vitamin B7), folate or a salt thereof (vitamin B9) including levomefolic acid or a salt thereof (L-5-Methyltetrahydrofolate), and cobalamin or a salt thereof including methylcobalamin or cyanocobalamin (vitamin B12). The orally administered supplement can also comprise one or more minerals. The one or more minerals can include calcium (optionally as calcium carbonate or d-calcium pantothenate), zinc (optionally as zinc oxide or an a zinc amino acid chelate), potassium, chlorine, magnesium (optionally as magnesium oxide, magnesium glycinate, magnesium bisglycinate, or magnesium aspartate), phosphorous, sodium, chromium (optionally as chromium picolinate), copper (optionally as copper gluconate), fluoride, iodine (optionally as potassium iodide), iron (optionally as carbonyl iron), molybdenum (optionally as sodium molybdate), selenium (optionally as 1-selenomethionine), manganese (optionally as manganese glycinate), and sulphur.

The one or more adaptogens can comprise *ginseng* root. The *ginseng* root can be Korean *ginseng* root. The *ginseng* root can be American *ginseng* root, red *ginseng* root, Chinese *ginseng* root, Indian *ginseng* root, Siberian *ginseng* root, or Brazilian *ginseng* root. The *ginseng* root can be present in the formulation, individually, in each case, in an amount of from about 0.1 mg to about 6 mg. In some embodiments, the *ginseng* root can be present in the formulation, individually, in each case, in an amount of from about 0.5 mg to about 4 mg. The *ginseng* root can be present in the formulation, individually, in each case, in an amount of about 3 mg. The Korean *ginseng* root can be present in the formulation, individually, in each case, in an amount of about 3 mg. The one or more adaptogens can comprise ginkgo leaf extract. The ginkgo leaf extract can be present in the formulation, individually, in each case, in an amount of from about 10 mg to about 80 mg. The ginkgo leaf extract can be present in the formulation in an amount of about 40 mg. The agent to maintain healthy cognitive function can comprise *rhodiola* root extract. The *rhodiola* root extract can be present in the formulation, individually, in each case, in an amount of from about 0.5 mg to about 4 mg. The *rhodiola* root extract can be present in the formulation, individually, in each case, in an amount of about 3 mg. The one or more antioxidants can comprise green tea leaf extract. The green tea leaf extract can be present in the formulation, individually, in each case, in an amount of from about 50 mg to about 600 mg. The green tea leaf extract can be present in the formulation, individually, in each case, in an amount of about 300 mg. The one or more antioxidants can comprise ginger root extract. The ginger root extract can be present in the formulation, individually, in each case, in an amount of from about 10 mg to about 80 mg. The ginger root extract can be present in the formulation in an amount of from about 40 mg. The agent to maintain healthy absorption of nutrients can comprise cayenne pepper. The cayenne pepper can be present in the formulation, individually, in each case, in an amount of from about 8 mg to about 30 mg. The cayenne pepper can be present in the formulation in an amount of about 14 mg.

The formulation can comprise *ginseng* root, ginkgo leaf extract, ginger root extract, cayenne pepper, *rhodiola* root extract, and green tea leaf extract. In the formulation, the *rhodiola* root extract can be present in the formulation in an amount of from about 0.5 mg to about 4 mg, the *ginseng* root can be present in the formulation in an amount of from about 0.5 mg to about 4 mg, ginkgo leaf extract can be present in the formulation in an amount of from about 10 mg to about 80 mg, the green tea leaf extract can be present in the formulation in an amount of from about 50 mg to about 600 mg, the ginger root extract can be present in the formulation in an amount of from about 10 mg to about 80 mg, and the cayenne pepper can be present in the formulation in an amount of from about 8 mg to about 30 mg. In the formulation, the *rhodiola* root extract can be present in the formulation in an amount of 3 mg, the *ginseng* root can be present in the formulation in an amount of about 3 mg, ginkgo leaf extract can be present in the formulation in an amount of about 40 mg, the green tea leaf extract can be present in the formulation in an amount of about 300 mg, the ginger root extract can be present in the formulation in an amount of about 40 mg, and the cayenne pepper can be present in the formulation in an amount of about 14 mg.

In another aspect, an orally administered supplement formulation in unit dose form can comprise an antioxidant, one or more compounds to maintain healthy cognitive performance, and an amino acid or a salt thereof, wherein the amino acid or a salt thereof can be present in the formulation, individually, in each case, in an amount of from about 10 mg to about 400 mg. The antioxidant can include, but not limited to, acai berries, alpha lipoic acid, astaxanthin, ashwagandha root extract, beta carotene, bilberry, blueberries, boswellia extract, CoQ-10, cucurmin, cysteine, bluta-thione, grape seed extract, green tea leaf extract, ginger root extract, garlic bulb, hydrogen peroxide, mangosteen, melatonin, oligomeric proanthocyanidins, olive leaf, soy bean, polycosanol, pychnogenol, taurine, quercetin, resveratrol, and rosemary leaf extract. The one or more compounds to maintain healthy cognitive performance can include bacopa leaf extract, *rhodiola* root extract, dimethylaminoethanol or a salt thereof, optionally huperzine A or a salt thereof, phosphatidylserine or a salt thereof, phosphatidylcholine or a salt thereof, and optionally soy lecithin or a salt thereof. The amino acid or a salt thereof can be L-theanine or a salt thereof, DL-phenylalanine or a salt thereof, L-tyrosine or a salt thereof, L-arginine or a salt thereof, 5-hydroxytryptophan or a salt thereof, and gamma aminobutyric acid (GABA) or a salt thereof. The orally administered supplement can further comprise one or more vitamins or salts thereof. These vitamins or salts thereof can include, but not limited to, vitamin A or a salt thereof (optionally as retinyl acetate and beta carotene), vitamin C or a salt thereof (optionally as ascorbic acid), vitamin D or a salt thereof (optionally as cholecalciferol), vitamin E or a salt thereof (optionally as d-alpha tocopheryl succinate), vitamin K or a salt thereof (optionally as phytonadione (K1)), and the B vitamins or salts thereof. The B vitamins or salts thereof can include thiamine or a salt thereof (vitamin B1), riboflavin or a salt thereof (vitamin B2), niacin or a salt thereof (vitamin B3), pantothenic acid or a salt thereof (vitamin B5), pyroxidine or a salt thereof including pyridoxyl 5 phosphate (vitamin B6), biotin or a salt thereof (vitamin B7), folate or a salt thereof (vitamin B9) including levomefolic acid or a salt thereof (L-5-Methyltetahydrofolate), and cobalamin or a salt thereof including methylcobalamin or cyanocobalamin (vitamin B12). The orally administered supplement can also comprise one or more minerals. The one or more minerals can include calcium (optionally as calcium carbonate or d-calcium pantothenate), zinc (optionally as zinc oxide or an a zinc amino acid chelate), potassium, chlorine, magnesium (optionally as magnesium oxide, magnesium glycinate, magnesium bisglycinate, or magnesium aspartate), phosphorous, sodium, chromium (optionally as chromium picolinate), copper (optionally as copper gluconate), fluoride, iodine (optionally as potassium iodide), iron (optionally as carbonyl iron), molybdenum (optionally as sodium molybdate), selenium (optionally as 1-selenomethionine), manganese (optionally as manganese glycinate), and sulphur.

The orally administered supplement can comprise the amino acid that can be L-theanine. The L-theanine can be present in the formulation in an amount of about 180 mg. The antioxidant can comprise resveratrol or a salt thereof. The resveratrol or a salt thereof can be present in the formulation, individually, in each case, in an amount of from about 8 mg to about 30 mg. The resveratrol or a salt thereof can be present in the formulation, individually, in each case, in an amount of about 10 mg. The one or more compounds to maintain healthy cognitive performance can comprise bacopa leaf extract. The bacopa leaf extract can be present in the formulation, individually, in each case, in an amount of from about 10 mg to about 600 mg. The bacopa leaf extract can be present in the formulation, individually, in each case, in an amount of about 300 mg. The one or more compounds to maintain healthy cognitive performance can comprise dimethylaminoethanol or a salt thereof. The dimethylaminoethanol or a salt thereof can be present in the formulation, individually, in each case, in an amount of from about 8 mg to about 30 mg. The dimethylaminoethanol or a salt thereof can be present in the formulation, individually, in each case, in an amount of about 10 mg. The one or more compounds to maintain cognitive performance can comprise pyrroloquinoline quinone or a salt thereof. The pyrroloquinoline quinone or a salt thereof can be present in the formulation, individually, in each case, in an amount of from about 0.1 mg to about 4 mg. The pyrroloquinoline quinone or a salt thereof can be present in the formulation, individually, in each case, in an amount of about 0.5 mg. The one or more compounds to maintain healthy cognitive performance can optionally comprise huperzine A or a salt thereof. The huperzine A or a salt thereof can be present in the formulation, individually, in each case, in an amount of from about 0.05 mg to about 4 mg. The huperzine A or a salt thereof can be present in the formulation in an amount of about 0.2 mg.

The formulation can comprise bacopa leaf extract, L-theanine or a salt thereof, resveratrol or a salt thereof, dimethylaminoethanol or a salt thereof, pyrroloquinoline quinone or a salt thereof, and optionally huperzine A or a salt thereof. In the formulation, the L-theanine can be present in the formulation in an amount of from about 10 mg to about 400 mg, the resveratrol or a salt thereof can be present in the formulation, individually, in each case, in an amount of from about 8 mg to about 30 mg, the bacopa leaf extract can be present in the formulation, individually, in each case, in an amount of from about 10 mg to about 600 mg, the dimethylaminoethanol or a salt thereof can be present in the formulation, individually, in each case, in an amount of from about 8 mg to about 30 mg, the pyrroloquinoline quinone or a salt thereof can be present in the formulation, individually, in each case, in an amount of from about 0.1 mg to about 4 mg, and optionally the huperzine A or a salt thereof can be present in the formulation, individually, in each case, in an amount of from about 0.05 mg to about 4 mg. In the formulation, the L-theanine can be present in the formulation in an amount of about 180 mg, the resveratrol or a salt thereof can be present in the formulation, individually, in each case, in an amount of about 10 mg, the bacopa leaf extract can be present in the formulation, individually, in each case, in an amount of about 300 mg, the dimethylaminoethanol or a salt thereof can be present in the formulation, individually, in each case, in an amount of about 10 mg, the pyrroloquinoline quinone or a salt thereof can be present in the formulation, individually, in each case, in an amount of about 0.5 mg, and the huperzine A or a salt thereof can optionally be present in the formulation, individually, in each case, in an amount of about 0.2 mg.

In another aspect, an orally administered supplement formulation in unit dose form can comprise an energy recycler, a first amino acid or a salt thereof, a second amino acid or a salt thereof, a third amino acid or a salt thereof, a fourth amino acid or a salt thereof, and an antioxidant, wherein the antioxidant can be present in the formulation, individually, in each case, in an amount of from about 10 mg to about 150 mg. The amino acids or salts thereof can include, but not limited to, L-theanine or a salt thereof, DL-phenylalanine or a salt thereof, L-tyrosine or a salt thereof, L-arginine or a salt thereof, 5-hydroxytryptophan or a salt thereof, L-glutamine or a salt thereof, and gamma aminobutyric acid (GABA) or a salt thereof. The antioxidant can include, but not limited to, acai berries, alpha lipoic acid, astaxanthin, ashwagandha root extract, beta carotene, bilberry, blueberries, boswellia extract, Co Q-10, cucurmin, cysteine, blutathione, grape seed extract, green tea leaf extract, ginger root extract, garlic bulb, hydrogen peroxide, mangosteen, melatonin, oligomeric proanthocyanidins, olive leaf, soy bean, polycosanol, pychnogenol, taurine, quercetin, resveratrol, and rosemary leaf extract. The orally administered supplement can further comprise one or more vitamins or salts thereof. These vitamins or salts thereof can include, but not limited to, vitamin A or a salt thereof (optionally as retinyl acetate and beta carotene), vitamin C or a salt thereof (optionally as ascorbic acid), vitamin D or a salt thereof (optionally as cholecalciferol), vitamin E or a salt thereof (optionally as d-alpha tocopheryl succinate), vitamin K or a salt thereof (optionally as phytonadione (K1)), and the B vitamins or salts thereof. The B vitamins or salts thereof can include thiamine or a salt thereof (vitamin B1), riboflavin or a salt thereof (vitamin B2), niacin or a salt thereof (vitamin B3), pantothenic acid or a salt thereof (vitamin B5), pyroxidine or a salt thereof including pyridoxyl 5 phosphate (vitamin B6), biotin or a salt thereof (vitamin B7), folate or a salt thereof (vitamin B9) including levomefolic acid or a salt thereof (L-5-Methyltetahydrofolate), and cobalamin or a salt thereof including methylcobalamin or cyanocobalamin (vitamin B12). The orally administered supplement can also comprise one or more minerals. The one or more minerals can include calcium (optionally as calcium carbonate or d-calcium pantothenate), zinc (optionally as zinc oxide or an a zinc amino acid chelate), potassium, chlorine, magnesium (optionally as magnesium oxide, magnesium glycinate, magnesium bisglycinate, or magnesium aspartate), phosphorous, sodium, chromium (optionally as chromium picolinate), copper (optionally as copper gluconate), fluoride, iodine (optionally as potassium iodide), iron (optionally as carbonyl iron), molybdenum (optionally as sodium molybdate), selenium (optionally as 1-selenomethionine), manganese (optionally as manganese glycinate), and sulphur.

The antioxidant can comprise taurine or a salt thereof. The taurine or a salt thereof can be present in the formulation, individually, in each case, in an amount of about 60 mg. The orally administered supplement can comprise the first amino acid that is DL-phenylalanine. The DL-phenylalanine can be present in the formulation in an amount of from about 10 mg to about 150 mg. The DL-phenylalanine can be present in the formulation in an amount of about 70 mg. The second amino acid or a salt thereof can comprise L-tyrosine or a salt thereof. The L-tyrosine can be present as a hydrochloric acid salt in the formulation in an amount of from about 10 mg to about 150 mg. The L-tyrosine can be present as a hydrochloric acid salt in the formulation in an amount of about 65 mg. The third amino acid or a salt thereof can comprise L-arginine or a salt thereof. The L-arginine can be present as a hydrochloric acid salt in the formulation in an amount of from about 10 mg to about 150 mg. The L-arginine can be present as a hydrochloric acid salt in the formulation in an amount of about 65 mg. The fourth amino acid can comprise 5-hydroxytryptophan. The 5-hydroxytryptophan can be present in the formulation, individually, in each case, in an amount of from about 10 mg to about 50 mg. The 5-hydroxytryptophan can be present in the formulation, individually, in each case, in an amount of about 20 mg. The energy recycler can comprise creatine or a salt thereof. The creatine can comprise creatine monohydrate, wherein the creatine monohydrate can be present in the formulation in an amount of from about 10 mg to about 50 mg. The creatine can comprise creatine monohydrate, wherein the creatine monohydrate can be present in the formulation in an amount of about 20 mg.

The formulation can comprise DL-phenylalanine or a salt thereof, L-tyrosine or a salt thereof, L-arginine or a salt thereof, taurine or a salt thereof, 5-hydroxytryptophan or a salt thereof, and creatine or a salt thereof. In the formulation, the taurine or a salt thereof can be present in the formulation, individually, in each case, in an amount of from about 10 mg to about 150 mg, the DL-phenylalanine can be present in the formulation in an amount of from about 10 mg to about 150 mg, the L-tyrosine can be present as a hydrochloric acid salt in the formulation in an amount of from about 10 mg to about 150 mg, the L-arginine can be present as a hydrochloric acid salt in the formulation in an amount of from about 10 mg to about 150 mg, the 5-hydroxytryptophan can be present in the formulation, individually, in each case, in an amount of from about 10 mg to about 50 mg, and the creatine monohydrate can be present in the formulation in an amount of from about 10 mg to about 50 mg. In the formulation, the taurine or a salt thereof can be present in the formulation, individually, in each case, in an amount of about 60 mg, the DL-phenylalanine can be present in the formulation in an amount of about 70 mg, the L-tyrosine can be present as a hydrochloric acid salt in the formulation in an amount of about 65 mg, the L-arginine can be present as a hydrochloric acid salt in the formulation in an amount of about 65 mg, the 5-hydroxytryptophan can be present in the formulation, individually, in each case, in an amount of about 20 mg, and the creatine monohydrate can be present in the formulation in an amount of about 20 mg.

In another aspect, the formulation can comprise *ginseng* root, ginkgo leaf extract, ginger root extract, cayenne pepper, *rhodiola* root extract, green tea leaf extract, bacopa leaf extract, L-theanine or a salt thereof, resveratrol or a salt thereof, dimethylaminoethanol or a salt thereof, pyrroloquinoline quinone or a salt thereof, optionally huperzine A or a salt thereof, DL-phenylalanine or a salt thereof, L-tyrosine or a salt thereof, L-arginine or a salt thereof, taurine or a salt thereof, 5-hydroxytryptophan or a salt thereof, and creatine or a salt thereof. In the formulation, the *rhodiola* root extract can be present in the formulation in an amount of from about 0.5 mg to about 4 mg, the *ginseng* root can be present in the formulation in an amount of from about 0.5 mg to about 4 mg, the ginkgo leaf extract can be present in the formulation in an amount of from about 10 mg to about 80 mg, the green tea leaf extract can be present in the formulation in an amount of from about 50 mg to about 600 mg, the ginger root extract can be present in the formulation in an amount of from about 10 mg to about 80 mg, the cayenne pepper can be present in the formulation in an amount of from about 8 mg to about 30 mg, the L-theanine can be present in the formulation in an amount of from about 10 mg to about 400 mg, the resveratrol or a salt thereof can be present in the formulation, individually, in each case, in an amount of from about 8 mg to about 30 mg, the bacopa leaf extract can be present in the formulation, individually, in each case, in an amount of from about 10 mg to about 600 mg, the dimethylaminoethanol or a salt thereof can be present in the formulation, individually, in each case, in an amount of from about 8 mg to about 30 mg, the pyrroloquinoline quinone or a salt thereof can be present in the formulation, individually, in each case, in an amount of from about 0.1 mg to about 4 mg, the huperzine A or a salt thereof can optionally be present in the formulation, individually, in each case, in an amount of from about 0.05 mg to about 4 mg, the taurine or a salt thereof can be present in the formulation, individually, in each case, in an amount of from about 10 mg to about 60 mg, the DL-phenylalanine can be present in the formulation in an amount of from about 10 mg to about 150 mg, the L-tyrosine can be present as a hydrochloric acid salt in the formulation in an amount of from about 10 mg to about 150 mg, the L-arginine can be present as a hydrochloric acid salt in the formulation in an amount of from about 10 mg to about 150 mg, the 5-hydroxytryptophan can be present in the formulation, individually, in each case, in an amount of from about 10 mg to about 50 mg, and the creatine monohydrate can be present in the formulation in an amount of from about 10 mg to about 50 mg.

In the formulation, the *rhodiola* root extract can be present in the formulation in an amount of about 3 mg, the *ginseng* root can be present in the formulation in an amount of about 3 mg, the ginkgo leaf extract can be present in the formulation in an amount of about 40 mg, the green tea leaf extract can be present in the formulation in an amount of about 300 mg, the ginger root extract can be present in the formulation in an amount of about 40 mg, the cayenne pepper can be present in the formulation in an amount of about 14 mg, the L-theanine can be present in the formulation in an amount of about 180 mg, the resveratrol or a salt thereof can be present in the formulation, individually, in each case, in an amount of about 10 mg, the bacopa leaf extract can be present in the formulation, individually, in each case, in an amount of about 300 mg, the dimethylaminoethanol or a salt thereof can be present in the formulation, individually, in each case, in an amount of about 10 mg, the pyrroloquinoline quinone or a salt thereof can be present in the formulation, individually, in each case, in an amount of about 0.5 mg, the huperzine A or a salt thereof can optionally be present in the formulation, individually, in each case, in an amount of about 0.2 mg, the taurine or a salt thereof can be present in the formulation, individually, in each case, in an amount of about 60 mg, the DL-phenylalanine can be present in the formulation in an amount of about 70 mg, the L-tyrosine can be present as a hydrochloric acid salt in the formulation in an amount of about 65 mg, the L-arginine can be present as a hydrochloric acid salt in the formulation in an amount of about 65 mg, the 5-hydroxytryptophan can be present in the formulation, individually, in each case, in an amount of about 20 mg, and the creatine monohydrate can be present in the formulation in an amount of about 20 mg.

The formulation can be formulated as a capsule, tablet, juice, powder, suspension, emulsifier, granules, troch, pill, suspension, spirit, and syrup. The formulation can be contained in capsules. Capsules suitable for oral administration can include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. The formulation can be a heterogeneous mixture. The formulation can be a homogenous mixture.

The formulation can further comprise physiologically or pharmaceutically acceptable excipients. Excipients can be selected to provide formulations for specific routes of administration and/or other types of administration, e.g., administration by tablet, capsule, or liquid dose. The excipient can be selected from the group consisting of vegetable oil, cellulose (cellulose gum), stearic acid, silicon dioxide (bamboo extract), magnesium stearate, titanium dioxide, natural vanillin and peppermint, polyethylene glycol, riboflavin, carnauba wax, and any combination thereof.

The formulation can be contained in a container. The formulation can retain at least about 80% of supplement activity for at least a year when stored in a sealed container, wherein the sealed container can be placed in an environment having a temperature of about 25° C. and about 50% relative humility. The formulation can retain at least about 70% of supplement activity for at least a year when stored in a sealed container, wherein the sealed container can be placed in an environment having a temperature of about 25° C. and about 40% relative humility. The formulation can retain at least about 90% of supplement activity for at least two years when stored in a sealed container, wherein the sealed container can be placed in an environment having a temperature of about 25° C. and about 50% relative humility. The formulation can retain at least about 95% of supplement activity for at least two years when stored in a sealed container, wherein the sealed container can be placed in an environment having a temperature of about 25° C. and about 50% relative humility.

2. Formulations: Category 2

The formulations of dietary supplements and methods of use thereof disclosed herein can be useful for helping individuals, among other things, induce and maintain sleep, calm down, stabilize their mod, regulate their clock, sleep-wake cycle, facilitate memory processing, support nervous system health, promote relaxation, reduce symptoms of stress and anxiety, improve cognition and memory, improve quality of sleep, reduce time required to fall asleep, achieve deep, restful sleep, uplift mood, offset caffeine in other dietary supplements, reduce brain cell activity, result in a relaxed state, wake up feeling refreshed and enable rejuvenated mornings, optimize memory consolidation, recovery, and neuroprotective processes, enhance cognition generally and the day after quality night of sleep, or feel more relaxed and balanced.

In an aspect, an orally administered supplement formulation in unit dose form can comprise a first amino acid or a salt thereof, a second amino acid or a salt thereof, an antioxidant, a precursor for a neurotransmitter, an agent to promote or encourage healthy sleep, an agent to maintain healthy cognitive function, and a compound to help maintain healthy brain function, wherein the compound to help maintain healthy brain function can be present in the formulation, individually, in each case, in an amount of from about 8 mg to about 40 mg. The antioxidant can include, but not limited to, acai berries, alpha lipoic acid, astaxanthin, ashwagandha root extract, beta carotene, bilberry, blueberries, boswellia extract, CoQ-10, cucurmin, cysteine, blutathione, grape seed extract, green tea leaf extract, ginger root extract, garlic bulb, hydrogen peroxide, mangosteen, melatonin, oligomeric proanthocyanidins, olive leaf, soy bean, polycosanol, pychnogenol, taurine, quercetin, resveratrol, and rosemary leaf extract. The one or more compounds to maintain healthy cognitive performance can include bacopa leaf extract, *rhodiola* root extract, dimethylaminoethanol or a salt thereof, optionally huperzine A or a salt thereof, phosphatidylserine or a salt thereof, phosphatidylcholine or a salt thereof, and optionally soy lecithin or a salt thereof. The amino acids or salts thereof can comprise, but not limited to, L-theanine or a salt thereof, DL-phenylalanine or a salt thereof, L-tyrosine or a salt thereof, L-arginine or a salt thereof, 5-hydroxytryptophan or a salt thereof, or gamma aminobutyric acid (GABA) or a salt thereof. The precursor for a neurotransmitter can include 5-hydroxytryptophan or a salt thereof, gamma aminobutyric acid (GABA) or a salt thereof, and L-glutamine or a salt thereof. The compound to help maintain healthy brain function can include myo-inositol and acetyl-L-carnitine or a salt thereof. The agent to promote or encourage healthy sleep can include melatonin or a salt thereof, valerian root extract, chamomile flower extract, hops flower extract, passion flower extract, and lemon balm leaf extract. The orally administered supplement can further comprise one or more vitamins or salts thereof. These vitamins or salts thereof can include, but not limited to, vitamin A or a salt thereof (optionally as retinyl acetate and beta carotene), vitamin C or a salt thereof (optionally as ascorbic acid), vitamin D or a salt thereof (optionally as cholecalciferol), vitamin E or a salt thereof (optionally as d-alpha tocopheryl succinate), vitamin K or a salt thereof (optionally as phytonadione (K1)), and the B vitamins or salts thereof. The B vitamins or salts thereof can include thiamine or a salt thereof (vitamin B1), riboflavin or a salt thereof (vitamin B2), niacin or a salt thereof (vitamin B3), pantothenic acid or a salt thereof (vitamin B5), pyroxidine or a salt thereof including pyridoxyl 5 phosphate (vitamin B6), biotin or a salt thereof (vitamin B7), folate or a salt thereof (vitamin B9) including levomefolic acid or a salt thereof (L-5-Methyltetahydrofolate), and cobalamin or a salt thereof including methylcobalamin or cyanocobalamin (vitamin B12). The orally administered supplement can also comprise one or more minerals. The one or more minerals can include calcium (optionally as calcium carbonate or d-calcium pantothenate), zinc (optionally as zinc oxide or an a zinc amino acid chelate), potassium, chlorine, magnesium (optionally as magnesium oxide, magnesium glycinate, magnesium bisglycinate, or magnesium aspartate), phosphorous, sodium, chromium (optionally as chromium picolinate), copper (optionally as copper gluconate), fluoride, iodine (optionally as potassium iodide), iron (optionally as carbonyl iron), molybdenum (optionally as sodium molybdate), selenium (optionally as l-selenomethionine), manganese (optionally as manganese glycinate), and sulphur.

The compound to help maintain healthy brain function can comprise myo-inositol. The myo-inositol can be present in the formulation in an amount from about 8 mg to about 40 mg. In some embodiments, the myo-inositol can be present in the formulation in an amount of about 16 mg. The first amino acid can comprise gamma-aminobutyric acid (GABA) or L-glutamine. The GABA can be present in the formulation, individually, in each case, in an amount of from about 10 mg to about 600 mg. The GABA can be present in the formulation, individually, in each case, in an amount of about 300 mg. The second amino acid can comprise L-theanine. The L-theanine can be present in the formulation, individually, in each case, in an amount of from about 10 mg to about 300 mg. The L-theanine can be present in the formulation, individually, in each case, in an amount of about 140 mg. The antioxidant can comprise taurine or a salt thereof. The taurine or a salt thereof can be present in the formulation, individually, in each case, in an amount of from about 10 mg to about 120 mg. The taurine or a salt thereof can be present in the formulation, individually, in each case, in an amount of about 64 mg. The precursor for a neurotransmitter can comprise L-glutamine or a salt thereof, or GABA or a salt thereof. The L-glutamine or a salt thereof can be present in the formulation, individually, in each case, in an amount of from about 8 mg to about 50 mg. The L-glutamine or a salt thereof can be present in the formulation, individually, in each case, in an amount of about 20 mg. The agent to promote or encourage healthy sleep can comprise melatonin or a salt thereof. The melatonin or a salt thereof can be present in the formulation, individually, in each case, in an amount of from about 7 mg to about 20 mg. The melatonin or a salt thereof can be present in the formulation, individually, in each case, in an amount of about 8 mg. The agent to maintain healthy cognitive function can comprise phosphatidylserine or a salt thereof. The phosphatidylserine or a salt thereof can be present in the formulation, individually, in each case, in an amount of from about 0.5 mg to about 4 mg or from about 0.1 mg to about 4 mg. The phosphatidylserine or a salt thereof can be present in the formulation, individually, in each case, in an amount of about 2 mg.

The formulation can comprise GABA or a salt thereof, L-theanine or a salt thereof, taurine or a salt thereof, L-glutamine or a salt thereof, myo-inositol, melatonin or a salt thereof, and phosphatidylserine or a salt thereof. In the formulation, the myo-inositol can be present in the formulation in an amount of from about 8 mg to about 40 mg, the GABA can be present in the formulation, individually, in each case, in an amount of from about 10 mg to about 600 mg, the L-theanine can be present in the formulation, individually, in each case, in an amount of from about 10 mg to about 300 mg, the taurine or a salt thereof can be present in the formulation, individually, in each case, in an amount of from about 10 mg to about 120 mg, the L-glutamine or a salt thereof can be present in the formulation, individually, in each case, in an amount of from about 8 mg to about 50 mg, the melatonin or a salt thereof can be present in the formulation, individually, in each case, in an amount of from about 7 mg to about 20 mg, and the phosphatidylserine or a salt thereof can be present in the formulation, individually, in each case, in an amount of from about 0.5 mg to about 4 mg or from about 0.1 mg to about 4 mg. In the formulation, the myo-inositol can be present in the formulation in an amount of about 16 mg, the GABA can be present in the formulation, individually, in each case, in an amount of about 300 mg, the L-theanine can be present in the formulation, individually, in each case, in an amount of about 140 mg, the taurine or a salt thereof can be present in the formulation, individually, in each case, in an amount of about 64 mg, the L-glutamine or a salt thereof can be present in the formulation, individually, in each case, in an amount of about 20 mg, the melatonin or a salt thereof can be present in the formulation, individually, in each case, in an amount of about 8 mg, and the phosphatidylserine or a salt thereof can be present in the formulation, individually, in each case, in an amount of about 2 mg.

In another aspect, an orally administered supplement formulation in unit dose form can comprise one or more compounds to promote or encourage healthy sleep, a precursor for a neurotransmitter, and an antioxidant, wherein the antioxidant can be present in the formulation, individually, in each case, in an amount of from about 8 mg to about 60 mg. The antioxidant can include, but not limited to acai berries, alpha lipoic acid, astaxanthin, ashwagandha root extract, beta carotene, bilberry, blueberries, boswellia extract, CoQ-10, cucurmin, cysteine, blutathione, grape seed extract, green tea leaf extract, ginger root extract, garlic bulb, hydrogen peroxide, mangosteen, melatonin, oligomeric proanthocyanidins, olive leaf, soy bean, polycosanol, pychnogenol, taurine, quercetin, resveratrol, and rosemary leaf extract. The precursor for a neurotransmitter can include 5-hydroxytryptophan or a salt thereof, GABA or a salt thereof, and L-glutamine or a salt thereof. The one or more compounds to promote or encourage healthy sleep can include melatonin or a salt thereof, valerian root extract, chamomile flower extract, hops flower extract, passion flower extract, and lemon balm leaf extract. The compound to help maintain healthy brain function can include myo-inositol and acetyl-L-carnitine or a salt thereof. The orally administered supplement can further comprise one or more vitamins or salts thereof. These vitamins or salts thereof can include, but not limited to, vitamin A or a salt thereof (optionally as retinyl acetate and beta carotene), vitamin C or a salt thereof (optionally as ascorbic acid), vitamin D or a salt thereof (optionally as cholecalciferol), vitamin E or a salt thereof (optionally as d-alpha tocopheryl succinate), vitamin K or a salt thereof (optionally as phytonadione (K1)), and the B vitamins or salts thereof. The B vitamins or salts thereof can include thiamine or a salt thereof (vitamin B1), riboflavin or a salt thereof (vitamin B2), niacin or a salt thereof (vitamin B3), pantothenic acid or a salt thereof (vitamin B5), pyroxidine or a salt thereof including pyridoxyl 5 phosphate (vitamin B6), biotin or a salt thereof (vitamin B7), folate or a salt thereof (vitamin B9) including levomefolic acid or a salt thereof (L-5-Methyltetahydrofolate), and cobalamin or a salt thereof including methylcobalamin or cyanocobalamin (vitamin B12). The orally administered supplement can also comprise one or more minerals. The one or more minerals can include calcium (optionally as calcium carbonate or d-calcium pantothenate), zinc (optionally as zinc oxide or an a zinc amino acid chelate), potassium, chlorine, magnesium (optionally as magnesium oxide, magnesium glycinate, magnesium bisglycinate, or magnesium aspartate), phosphorous, sodium, chromium (optionally as chromium picolinate), copper (optionally as copper gluconate), fluoride, iodine (optionally as potassium iodide), iron (optionally as carbonyl iron), molybdenum (optionally as sodium molybdate), selenium (optionally as 1-selenomethionine), manganese (optionally as manganese glycinate), and sulphur.

The antioxidant can comprise ashwagandha root extract. The ashwagandha root extract can be present in the formulation, individually, in each case, in an amount of about 28 mg. The one or more compounds to promote or encourage healthy sleep can comprise valerian root extract. The valerian root extract can be present in the formulation, individually, in each case, in an amount of from about 50 mg to about 300 mg. The valerian root extract can be present in the formulation, individually, in each case, in an amount of about 140 mg. The one or more compounds to promote or encourage healthy sleep can comprise chamomile flower extract. The chamomile flower extract can be present in the formulation, individually, in each case, in an amount of from about 10 mg to about 50 mg. The chamomile flower extract can be present in the formulation, individually, in each case, in an amount of about 24 mg. The one or more compounds to promote or encourage healthy sleep can comprise hops flower extract. The hops flower extract can be present in the formulation, individually, in each case, in an amount of from about 10 mg to about 50 mg. The hops flower extract can be present in the formulation, individually, in each case, in an amount of about 24 mg. The precursor for a neurotransmitter can comprise 5-hydroxytryptophan or a salt thereof. The 5-hydroxytryptophan or a salt thereof can be present in the formulation, individually, in each case, in an amount of from about 8 mg to about 60 mg. The 5-hydroxytryptophan or a salt thereof can be present in the formulation, individually, in each case, in an amount of about 34 mg. The one or more compounds to promote or encourage healthy sleep can comprise passion flower extract. The passion flower extract can be present in the formulation, individually, in each case, in an amount of from about 8 mg to about 60 mg. The passion flower extract can be present in the formulation, individually, in each case, in an amount of about 20 mg. The one or more compounds to promote or encourage healthy sleep can comprise lemon balm leaf extract. The lemon balm leaf extract can be present in the formulation, individually, in each case, in an amount of from about 8 mg to about 60 mg. The lemon balm leaf extract can be present in the formulation, individually, in each case, in an amount of about 10 mg.

The formulation can comprise valerian root extract, 5-hydroxytryptophan or a salt thereof, ashwagandha root extract, chamomile flower extract, hops flower extract, passion flower extract, and lemon balm leaf extract. In the formulation, the ashwagandha root extract can be present in the formulation, individually, in each case, in an amount of from about 8 to about 60 mg, the valerian root extract can be present in the formulation, individually, in each case, in an amount of from about 50 mg to about 300 mg, the chamomile flower extract can be present in the formulation, individually, in each case, in an amount of from about 10 mg to about 50 mg, the hops flower extract can be present in the formulation, individually, in each case, in an amount of from about 10 mg to about 50 mg, the 5-hydroxytryptophan or a salt thereof can be present in the formulation, individually, in each case, in an amount of from about 8 mg to about 60 mg, the passion flower extract can be present in the formulation, individually, in each case, in an amount of from about 8 mg to about 60 mg, and the lemon balm leaf extract can be present in the formulation, individually, in each case, in an amount of from about 8 mg to about 60 mg. In the formulation, the ashwagandha root extract can be present in the formulation, individually, in each case, in an amount of about 28 mg, the valerian root extract can be present in the formulation, individually, in each case, in an amount of about 140 mg, the chamomile flower extract can be present in the formulation, individually, in each case, in an amount of about 24 mg, the hops flower extract can be present in the formulation, individually, in each case, in an amount of about 24 mg, the 5-hydroxytryptophan or a salt thereof can be present in the formulation, individually, in each case, in an amount of about 34 mg, the passion flower extract can be present in the formulation, individually, in each case, in an amount of about 20 mg, and the lemon balm leaf extract can be present in the formulation, individually, in each case, in an amount of about 10 mg.

In another aspect, the formulation can comprise GABA or a salt thereof, L-theanine or a salt thereof, taurine or a salt thereof, L-glutamine or a salt thereof, myo-inositol, melatonin or a salt thereof, phosphatidylserine or a salt thereof, valerian root extract, 5-hydroxytryptophan or a salt thereof, ashwagandha root extract, chamomile flower extract, hops flower extract, passion flower extract, and lemon balm leaf extract. In the formulation, the myo-inositol can be present in the formulation in an amount of from about 8 mg to about 40 mg, the GABA can be present in the formulation, individually, in each case, in an amount of from about 10 mg to about 600 mg, the L-theanine can be present in the formulation, individually, in each case, in an amount of from about 10 mg to about 300 mg, the taurine or a salt thereof can be present in the formulation, individually, in each case, in an amount of from about 10 mg to about 120 mg, the L-glutamine or a salt thereof can be present in the formulation, individually, in each case, in an amount of from about 8 mg to about 50 mg, the melatonin or a salt thereof can be present in the formulation, individually, in each case, in an amount of from about 7 mg to about 20 mg, the phosphatidylserine or a salt thereof can be present in the formulation, individually, in each case, in an amount of from about 0.5 mg to about 4 mg or from about 0.1 mg to about 4 mg, the ashwagandha root extract can be present in the formulation, individually, in each case, in an amount of from about 8 to about 60 mg, the valerian root extract can be present in the formulation, individually, in each case, in an amount of from about 50 mg to about 300 mg, the chamomile flower extract can be present in the formulation, individually, in each case, in an amount of from about 10 mg to about 50 mg, the hops flower extract can be present in the formulation, individually, in each case, in an amount of from about 10 mg to about 50 mg, the 5-hydroxytryptophan or a salt thereof can be present in the formulation, individually, in each case, in an amount of from about 8 mg to about 60 mg, the passion flower extract can be present in the formulation, individually, in each case, in an amount of from about 8 mg to about 60 mg, and the lemon balm leaf extract can be present in the formulation, individually, in each case, in an amount of from about 8 mg to about 60 mg.

In the formulation, the myo-inositol can be present in the formulation in an amount of about 16 mg, the GABA can be present in the formulation, individually, in each case, in an amount of about 300 mg, the L-theanine can be present in the formulation, individually, in each case, in an amount of about 140 mg, the taurine or a salt thereof can be present in the formulation, individually, in each case, in an amount of about 64 mg, the L-glutamine or a salt thereof can be present in the formulation, individually, in each case, in an amount of about 20 mg, the melatonin or a salt thereof can be present in the formulation, individually, in each case, in an amount of about 8 mg, the phosphatidylserine or a salt thereof can be present in the formulation, individually, in each case, in an amount of about 2 mg, the ashwagandha root extract can be present in the formulation, individually, in each case, in an amount of about 28 mg, the valerian root extract can be present in the formulation, individually, in each case, in an amount of about 140 mg, the chamomile flower extract can be present in the formulation, individually, in each case, in an amount of about 24 mg, the hops flower extract can be present in the formulation, individually, in each case, in an amount of about 24 mg, the 5-hydroxytryptophan or a salt thereof can be present in the formulation, individually, in each case, in an amount of about 34 mg, the passion flower extract can be present in the formulation, individually, in each case, in an amount of about 20 mg, and the lemon balm leaf extract can be present in the formulation, individually, in each case, in an amount of about 10 mg.

The formulation can be formulated as a capsule, tablet, juice, powder, suspension, emulsifier, granules, troch, pill, suspension, spirit, and syrup. The formulation can be contained in capsules. Capsules suitable for oral administration can include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. The formulation can be a heterogeneous mixture. The formulation can be a homogenous mixture.

The formulation can further comprise physiologically or pharmaceutically acceptable excipients. Excipients can be selected to provide formulations for specific routes of administration and/or other types of administration, e.g., administration by tablet, capsule, or liquid dose. The excipient can be selected from the group consisting of vegetable oil, cellulose (cellulose gum), stearic acid, silicon dioxide (bamboo extract), magnesium stearate, titanium dioxide, natural vanillin, polyethylene glycol, riboflavin, carnauba wax, and any combination thereof.

The formulation can be contained in a container. The formulation can retain at least about 80% of supplement activity for at least a year when stored in a sealed container, wherein the sealed container can be placed in an environment having a temperature of about 25° C. and about 50% relative humility. The formulation can retain at least about 70% of supplement activity for at least a year when stored in a sealed container, wherein the sealed container can be placed in an environment having a temperature of about 25° C. and about 40% relative humility. The formulation can retain at least about 90% of supplement activity for at least two years when stored in a sealed container, wherein the sealed container can be placed in an environment having a temperature of about 25° C. and about 50% relative humility. The formulation can retain at least about 95% of supplement activity for at least two years when stored in a sealed container, wherein the sealed container can be placed in an environment having a temperature of about 25° C. and about 50% relative humility.

3. Formulations: Category 3

The formulations of dietary supplements disclosed herein can be useful for helping individuals, among other things, promote learning and memory, support cognitive function, restore and stabilize cells, facilitate energy production, improve mental and emotional health, stabilize metabolism rate and mood, facilitate chemical reactions critical to health, limit stress and anxiety, improve attention and focus, improve mental performance and ability to concentrate, improve overall well-being and vitality, increase energy, or support long-term brain health.

In an aspect, an orally administered supplement formulation in unit dose form can comprise one or more agents to maintain healthy cognitive function, one or more ingredients to help maintain healthy memory performance, and a compound to help maintain healthy brain function, wherein the compound to help maintain healthy brain function can be present in the formulation, individually, in each case, in an amount of from about 10 mg to about 160 mg. The one or more agents to maintain healthy cognitive function can include bacopa leaf extract, *rhodiola* root extract, dimethylaminoethanol or a salt thereof, optionally huperzine A or a salt thereof, phosphatidylserine or a salt thereof, phosphatidylcholine or a salt thereof, and optionally soy lecithin or a salt thereof. The compound to help maintain healthy brain function can include myo-inositol and acetyl-L-carnitine or a salt thereof. The one or more ingredients to help maintain healthy memory performance can include alpha-glycerophosphocholine or a salt thereof, optionally citicoline or a salt thereof, and choline. The orally administered supplement can further comprise one or more vitamins or salts thereof. These vitamins or salts thereof can include, but not limited to, vitamin A or a salt thereof (optionally as retinyl acetate and beta carotene), vitamin C or a salt thereof (optionally as ascorbic acid), vitamin D or a salt thereof (optionally as cholecalciferol), vitamin E or a salt thereof (optionally as d-alpha tocopheryl succinate), vitamin K or a salt thereof (optionally as phytonadione (K1)), and the B vitamins or salts thereof. The B vitamins or salts thereof can include thiamine or a salt thereof (vitamin B1), riboflavin or a salt thereof (vitamin B2), niacin or a salt thereof (vitamin B3), pantothenic acid or a salt thereof (vitamin B5), pyroxidine or a salt thereof including pyridoxyl 5 phosphate (vitamin B6), biotin or a salt thereof (vitamin B7), folate or a salt thereof (vitamin B9) including levomefolic acid or a salt thereof (L-5-Methyltetahydrofolate), and cobalamin or a salt thereof including methylcobalamin or cyanocobalamin (vitamin B12). The orally administered supplement can also comprise one or more minerals. The one or more minerals can include calcium (optionally as calcium carbonate or d-calcium pantothenate), zinc (optionally as zinc oxide or an a zinc amino acid chelate), potassium, chlorine, magnesium (optionally as magnesium oxide, magnesium glycinate, magnesium bisglycinate, or magnesium aspartate), phosphorous, sodium, chromium (optionally as chromium picolinate), copper (optionally as copper gluconate), fluoride, iodine (optionally as potassium iodide), iron (optionally as carbonyl iron), molybdenum (optionally as sodium molybdate), selenium (optionally as 1-selenomethionine), manganese (optionally as manganese glycinate), and sulphur.

The compound to help maintain healthy brain function can comprise myo-inositol. The myo-inositol can be present in the formulation, individually, in each case, in an amount from about 40 mg to about 120 mg. In some embodiments, the myo-inositol can be present in the formulation, individually, in each case, in an amount of about 80 mg. The one or more agents to maintain healthy cognitive function can comprise phosphatidylcholine or a salt thereof. The phosphatidylcholine or a salt thereof can be present in the formulation, individually, in each case, in an amount of from about 10 mg to about 300 mg or from about 1 mg to about 300 mg. The phosphatidylcholine or a salt thereof can be present in the formulation, individually, in each case, in an amount of about 148 mg or 20 mg. The one or more agents to maintain healthy cognitive function can comprise phosphatidylserine or a salt thereof. The phosphatidylserine or a salt thereof can be present in the formulation, individually, in each case, in an amount of from about 6 mg to about 20 mg or from about 1 mg to about 20 mg. The phosphatidylserine or a salt thereof can be present in the formulation, individually, in each case, in an amount of about 6 mg. The one or more ingredients to help maintain healthy memory performance can comprise alpha-glycerophosphocholine or a salt thereof. The alpha-glycerophosphocholine or a salt thereof can be present in the formulation, individually, in each case, in an amount of from about 6 mg to about 20 mg or from about 1 mg to about 20 mg. The alpha-glycerophosphocholine or a salt thereof can be present in the formulation, individually, in each case, in an amount of about 6 mg. The one or more ingredients to help maintain healthy memory performance can optionally comprise citicoline or a salt thereof. The citicoline or a salt thereof can optionally be present in the formulation, individually, in each case, in an amount of from about 5 mg to about 30 mg or from about 1 mg to about 30 mg. The citicoline or a salt thereof can optionally be present in the formulation, individually, in each case, in an amount of about 5 mg or about 3 mg. The one or more ingredients to help maintain healthy memory performance can comprise choline. The choline can be present in the formulation, individually, in each case, in an amount of from about 10 mg to about 100 mg or about 10 mg to about 200 mg. The choline can be present in the formulation, individually, in each case, in an amount of about 55 mg or about 110 mg. The one or more agents to maintain healthy cognitive function can optionally comprise soy lecithin or a salt thereof. The soy lecithin or a salt thereof can optionally be present in the formulation, individually, in each case, in an amount of from about 10 mg to about 100 mg. The soy lecithin or a salt thereof can optionally be present in the formulation, individually, in each case, in an amount of about 20 mg.

The formulation can comprise phosphatidylcholine or a salt thereof, myo-inositol, choline, optionally soy lecithin or a salt thereof, alpha-glycerophosphocholine or a salt thereof, phosphatidylserine or a salt thereof, and optionally citicoline or a salt thereof. In the formulation, the myo-inositol can be present in the formulation, individually, in each case, in an amount of from about 10 mg to about 160 mg, the phosphatidylcholine or a salt thereof can be present in the formulation, individually, in each case, in an amount of from about 10 mg to about 300 mg or about 1 mg to about 300 mg, the phosphatidylserine or a salt thereof can be present in the formulation, individually, in each case, in an amount of from about 6 mg to about 20 mg or from about 1 mg to about 20 mg, the alpha-glycerophosphocholine or a salt thereof can be present in the formulation, individually, in each case, in an amount of from about 6 mg to about 20 mg or from about 1 mg to about 20 mg, the citicoline or a salt thereof can optionally be present in the formulation, individually, in each case, in an amount of from about 5 mg to about 30 mg or about 1 mg to about 30 mg, the choline can be present in the formulation, individually, in each case, in an amount of from about 10 mg to about 100 mg or from about 10 mg to about 200 mg, and the soy lecithin or a salt thereof can optionally be present in the formulation, individually, in each case, in an amount of from about 10 mg to about 100 mg. In the formulation, the myo-inositol can be present in the formulation, individually, in each case, in an amount of about 80 mg, the phosphatidylcholine or a salt thereof can be present in the formulation, individually, in each case, in an amount of about 148 mg or 20 mg, the phosphatidylserine or a salt thereof can be present in the formulation, individually, in each case, in an amount of about 6 mg, the alpha-glycerophosphocholine or a salt thereof can be present in the formulation, individually, in each case, in an amount of about 6 mg, the citicoline or a salt thereof can optionally be present in the formulation, individually, in each case, in an amount of about 5 mg or about 3 mg, the choline can be present in the formulation, individually, in each case, in an amount of about 55 mg or about 110 mg, and the soy lecithin or a salt thereof can optionally be present in the formulation, individually, in each case, in an amount of about 20 mg.

In another aspect, an orally administered supplement formulation in unit dose form can comprise one or more antioxidants, an amino acid or a salt thereof, one or more agents to help maintain healthy blood circulation, and a compound to help maintain healthy brain function, wherein the compound to help maintain healthy brain function can be present in the formulation, individually, in each case, in an amount of from about 10 mg to about 50 mg. In some embodiments, the formulation can further comprise chlorophyll and menaquinone MK7 (K2). The antioxidant can include, but not limited to acai berries, alpha lipoic acid, astaxanthin, ashwagandha root extract, beta carotene, bilberry, blueberries, boswellia extract, CoQ-10, cucurmin, cysteine, blutathione, grape seed extract, green tea leaf extract, ginger root, garlic bulb, hydrogen peroxide, mangosteen, melatonin, oligomeric proanthocyanidins, olive leaf, soy bean, polycosanol, pychnogenol, taurine, quercetin, resveratrol, and rosemary leaf extract. The compound to help maintain healthy brain function can include myo-inositol and acetyl-L-carnitine or a salt thereof. The one or more agents to help maintain healthy blood circulation can include L-citrulline or a salt thereof, beet root extract, and turmeric root extract. The amino acid or a salt thereof can be L-theanine or a salt thereof, DL-phenylalanine or a salt thereof, L-tyrosine or a salt thereof, L-arginine or a salt thereof, 5-hydroxytryptophan or a salt thereof, or gamma aminobutyric acid (GABA) or a salt thereof. The orally administered supplement can further comprise one or more vitamins or salts thereof. These vitamins or salts thereof can include, but not limited to, vitamin A or a salt thereof (optionally as retinyl acetate and beta carotene), vitamin C or a salt thereof (optionally as ascorbic acid), vitamin D or a salt thereof (optionally as cholecalciferol), vitamin E or a salt thereof (optionally as d-alpha tocopheryl succinate), vitamin K or a salt thereof (optionally as phytonadione (K1)), and the B vitamins or salts thereof. The B vitamins or salts thereof can include thiamine or a salt thereof (vitamin B1), riboflavin or a salt thereof (vitamin B2), niacin or a salt thereof (vitamin B3), pantothenic acid or a salt thereof (vitamin B5), pyroxidine or a salt thereof including pyridoxyl 5 phosphate (vitamin B6), biotin or a salt thereof (vitamin B7), folate or a salt thereof (vitamin B9) including levomefolic acid or a salt thereof (L-5-Methyltetahydrofolate), and cobalamin or a salt thereof including methylcobalamin or cyanocobalamin (vitamin B12). The orally administered supplement can also comprise one or more minerals. The one or more minerals can include calcium (optionally as calcium carbonate or d-calcium pantothenate), zinc (optionally as zinc oxide or an a zinc amino acid chelate), potassium, chlorine, magnesium (optionally as magnesium oxide, magnesium glycinate, magnesium bisglycinate, or magnesium aspartate), phosphorous, sodium, chromium (optionally as chromium picolinate), copper (optionally as copper gluconate), fluoride, iodine (optionally as potassium iodide), iron (optionally as carbonyl iron), molybdenum (optionally as sodium molybdate), selenium (optionally as 1-selenomethionine), manganese (optionally as manganese glycinate), and sulphur.

The compound to help maintain healthy brain function can comprise acetyl-L-carnitine or a salt thereof. The acetyl-L-carnitine or a salt thereof can be present in the formulation, individually, in each case, in an amount from about 10 mg to about 50 mg. In some embodiments, the acetyl-L-carnitine or a salt thereof can be present in the formulation, individually, in each case, in an amount of about 25 mg. The one or more antioxidants can comprise taurine or a salt thereof. The taurine or a salt thereof can be present in the formulation, individually, in each case, in an amount of from about 10 mg to about 80 mg. The taurine or a salt thereof can be present in the formulation, individually, in each case, in an amount of about 40 mg. The one or more antioxidants can comprise alpha lipoic acid or a salt thereof. The alpha lipoic acid or a salt thereof can be present in the formulation, individually, in each case, in an amount of from about 10 mg to about 50 mg. The alpha lipoic acid or a salt thereof can be present in the formulation, individually, in each case, in an amount from about 1 mg to about 100 mg. In some embodiments, the alpha lipoic acid or a salt thereof can be present in the formulation, individually, in each case, in an amount of about 25 mg. The one or more antioxidants can comprise resveratrol or a salt thereof. The resveratrol or a salt thereof can be present in the formulation, individually, in each case, in an amount of from about 10 mg to about 50 mg. The resveratrol or a salt thereof can be present in the formulation, individually, in each case, in an amount of about 20 mg. The one or more antioxidants can comprise quercetin or a salt thereof. The quercetin or a salt thereof can be present in the formulation, individually, in each case, in an amount of from about 0.5 mg to about 5 mg or from about 0.5 mg to about 10 mg. The quercetin or a salt thereof can be present in the formulation, individually, in each case, in an amount of about 5 mg. The chlorophyll or a salt thereof can be present in the formulation, individually, in each case, in an amount from about 0.1 mg to about 5 mg. The chlorophyll or a salt thereof can be present in the formulation, individually, in each case, in an amount of about 2 mg. The menaquinone MK7 (K2) or a salt thereof can be present in the formulation, individually, in each case, in an amount from about 0.001 mg to about 0.1 mg. The menaquinone MK7 (K2) or a salt thereof can be present in the formulation, individually, in each case, in an amount of about 0.01 mg. The one or more antioxidants can comprise astaxanthin or a salt thereof. The astaxanthin or a salt thereof can be present in the formulation, individually, in each case, in an amount of from about 0.5 mg to about 4 mg or from about 0.1 mg to about 4 mg. The astaxanthin or a salt thereof can be present in the formulation, individually, in each case, in an amount of about 1 mg. The one or more antioxidants can comprise CoQ10. The CoQ10 can be present in the formulation, individually, in each case, in an amount of from about 0.01 mg to about 4 mg. The CoQ10 can be present in the formulation, individually, in each case, in an amount of about 0.5 mg. The amino acid can be L-arginine. The L-arginine can be present as a hydrochloric acid salt in the formulation, individually, in each case, in an amount of from about 10 mg to about 100 mg. The L-arginine can be present as a hydrochloric acid salt in the formulation, individually, in each case, in an amount of about 55 mg. The one or more agents to help maintain healthy blood circulation can comprise L-citrulline or a salt thereof. The L-citrulline or a salt thereof can be present in the formulation, individually, in each case, in an amount of from about 8 mg to about 80 mg. The L-citrulline or a salt thereof can be present in the formulation, individually, in each case, in an amount of about 40 mg. The one or more agents to help maintain healthy blood circulation can comprise beet root extract. The beet root extract can be present in the formulation, individually, in each case, in an amount of from about 8 mg to about 80 mg. The beet root extract can be present in the formulation, individually, in each case, in an amount of about 40 mg.

The formulation can comprise L-arginine or a salt thereof, L-citrulline or a salt thereof, taurine or a salt thereof, beet root extract, acetyl-L-carnitine or a salt thereof, alpha lipoic acid or a salt thereof, resveratrol or a salt thereof, quercetin or a salt thereof, astaxanthin or a salt thereof, and CoQ10. In the formulation, the acetyl-L-carnitine or a salt thereof can be present in the formulation, individually, in each case, in an amount of from about 10 mg to about 50 mg, the taurine or a salt thereof can be present in the formulation, individually, in each case, in an amount of from about 10 mg to about 80 mg, the alpha lipoic acid or a salt thereof can be present in the formulation, individually, in each case, in an amount of from about 10 mg to about 50 mg, the resveratrol or a salt thereof can be present in the formulation, individually, in each case, in an amount of from about 10 mg to about 50 mg, the quercetin or a salt thereof can be present in the formulation, individually, in each case, in an amount of from about 0.5 mg to about 5 mg or from about 0.5 mg to about 10 mg, the astaxanthin or a salt thereof can be present in the formulation, individually, in each case, in an amount of from about 0.5 mg to about 4 mg or from about 0.1 mg to about 4 mg, the chlorophyll or a salt thereof can be present in the formulation, individually, in each case, in an amount from about 0.1 mg to about 5 mg, the menaquinone MK7 (K2) or a salt thereof can be present in the formulation, individually, in each case, in an amount from about 0.001 mg to about 0.1 mg, the CoQ10 can be present in the formulation, individually, in each case, in an amount of from about 0.01 mg to about 4 mg, the L-arginine can be present as a hydrochloric acid salt in the formulation, individually, in each case, in an amount of from about 10 mg to about 100 mg, the L-citrulline or a salt thereof can be present in the formulation, individually, in each case, in an amount of from about 8 mg to about 80 mg, and the beet root extract can be present in the formulation, individually, in each case, in an amount of from about 8 mg to about 80 mg. In the formulation, the acetyl-L-carnitine or a salt thereof can be present in the formulation, individually, in each case, in an amount of about 25 mg, the taurine or a salt thereof can be present in the formulation, individually, in each case, in an amount of about 40 mg, the alpha lipoic acid or a salt thereof can be present in the formulation, individually, in each case, in an amount of about 25 mg, the resveratrol or a salt thereof can be present in the formulation, individually, in each case, in an amount of about 20 mg, the quercetin or a salt thereof can be present in the formulation, individually, in each case, in an amount of about 5 mg, the astaxanthin or a salt thereof can be present in the formulation, individually, in each case, in an amount of about 1 mg, the chlorophyll or a salt thereof can be present in the formulation, individually, in each case, in an amount of about 2 mg, the menaquinone MK7 (K2) or a salt thereof can be present in the formulation, individually, in each case, in an amount of about 0.01 mg, the CoQ10 can be present in the formulation, individually, in each case, in an amount of about 0.5 mg, the L-arginine can be present as a hydrochloric acid salt in the formulation, individually, in each case, in an amount of about 55 mg, the L-citrulline or a salt thereof can be present in the formulation, individually, in each case, in an amount of about 40 mg, and the beet root extract can be present in the formulation, individually, in each case, in an amount of about 40 mg.

In another aspect, an orally administered supplement formulation in unit dose form can comprise one or more antioxidants, one or more adaptogens, an agent to help maintain healthy blood circulation, an agent to maintain healthy absorption of nutrients, and an agent to maintain healthy heart function, wherein the agent to maintain healthy heart function can be present in the formulation, individually, in each case, in an amount of from about 10 mg to about 150 mg. The one or more antioxidants can include, but not limited to, acai berries, alpha lipoic acid, astaxanthin, ashwagandha root extract, beta carotene, bilberry, blueberries, boswellia extract, CoQ-10, cucurmin, cysteine, blutathione, grape seed extract, green tea leaf extract, ginger root extract, garlic bulb, hydrogen peroxide, mangosteen, melatonin, oligomeric proanthocyanidins, olive leaf, soy bean, polycosanol, pychnogenol, taurine, quercetin, resveratrol, and rosemary leaf extract. The one or more adaptogens can include, but not limited to, ashwagandha root extract, boswellia extract, eleuthero, holy basil (Tulsi), maca, *ginseng, rhodiola* root extract, schisandra, *astragalus*, licorice, moringa, ginkgo root extract, and gotu kola. The one or more agents to help maintain healthy blood circulation can include L-citrulline or a salt thereof, beet root extract, and turmeric root extract. The agent to maintain healthy absorption of nutrients can include cayenne pepper. The agent to maintain healthy heart function can optionally include flax seed oil.

The orally administered supplement can further comprise one or more vitamins or salts thereof. These vitamins or salts thereof can include, but not limited to, vitamin A or a salt thereof (optionally as retinyl acetate and beta carotene), vitamin C or a salt thereof (optionally as ascorbic acid), vitamin D or a salt thereof (optionally as cholecalciferol), vitamin E or a salt thereof (optionally as d-alpha tocopheryl succinate), vitamin K or a salt thereof (optionally as phytonadione (K1)), and the B vitamins or salts thereof. The B vitamins or salts thereof can include thiamine or a salt thereof (vitamin B1), riboflavin or a salt thereof (vitamin B2), niacin or a salt thereof (vitamin B3), pantothenic acid or a salt thereof (vitamin B5), pyroxidine or a salt thereof including pyridoxyl 5 phosphate (vitamin B6), biotin or a salt thereof (vitamin B7), folate or a salt thereof (vitamin B9) including levomefolic acid or a salt thereof (L-5-Methyltetahydrofolate), and cobalamin or a salt thereof including methylcobalamin or cyanocobalamin (vitamin B12). The orally administered supplement can also comprise one or more minerals. The one or more minerals can include calcium (optionally as calcium carbonate or d-calcium pantothenate), zinc (optionally as zinc oxide or an a zinc amino acid chelate), potassium, chlorine, magnesium (optionally as magnesium oxide, magnesium glycinate, magnesium bis-glycinate, or magnesium aspartate), phosphorous, sodium, chromium (optionally as chromium picolinate), copper (optionally as copper gluconate), fluoride, iodine (optionally as potassium iodide), iron (optionally as carbonyl iron), molybdenum (optionally as sodium molybdate), selenium (optionally as 1-selenomethionine), manganese (optionally as manganese glycinate), and sulphur.

The agent to maintain healthy heart function can optionally comprise flax seed oil. The flax seed oil can optionally be present in the formulation, individually, in each case, in an amount of about 100 mg. The one or more antioxidants can comprise grape seed extract. The grape seed extract can be present in the formulation, individually, in each case, in an amount of from about 10 mg to about 50 mg. The grape seed extract can be present in the formulation, individually, in each case, in an amount from about 1 mg to about 100 mg. In some embodiments, the grape seed extract can be present in the formulation, individually, in each case, in an amount of about 25 mg. The one or more antioxidants can comprise garlic bulb. The garlic bulb can be present in the formulation, individually, in each case, in an amount of from about 5 mg to about 50 mg. The garlic bulb can be present in the formulation, individually, in each case, in an amount of about 5 mg. The one or more adaptogens can comprise ginkgo leaf extract. The ginkgo leaf extract can be present in the formulation, individually, in each case, in an amount of from about 5 mg to about 50 mg or from about 5 mg to about 100 mg. The ginkgo leaf extract can be present in the formulation, individually, in each case, in an amount of about 5 mg or about 20 mg. The one or more adaptogens can comprise *ginseng* root extract. The *ginseng* root can be American *ginseng* root, red *ginseng* root, Chinese *ginseng* root, Indian *ginseng* root, Siberian *ginseng* root, or Brazilian *ginseng* root. The *ginseng* root extract can be Korean *ginseng* root extract. The *ginseng* root extract can be present in the formulation, individually, in each case, in an amount of from about 5 mg to about 50 mg. The *ginseng* root extract can be present in the formulation, individually, in each case, in an amount of about 5 mg. The agent to help maintain healthy blood circulation can be turmeric root extract. The turmeric root extract can be present in the formulation, individually, in each case, in an amount of from about 10 mg to about 100 mg or from about 10 mg to about 150 mg. The turmeric root extract can be present in the formulation, individually, in each case, in an amount of about 55 mg or about 80 mg. The agent to maintain healthy absorption of nutrients can be cayenne pepper. The cayenne pepper can be present in the formulation, individually, in each case, in an amount of from about 10 mg to about 100 mg or from about 5 mg to about 100 mg. The cayenne pepper can be present in the formulation, individually, in each case, in an amount of about 20 mg. In some embodiments, one or more antioxidants can optionally comprise soybean oil. The soybean oil can optionally be present in the formulation, individually, in each case, in an amount of from about 10 mg to about 200 mg. The soybean oil can optionally be present in the formulation, individually, in each case, in an amount of about 120 mg. The one or more adaptogens can comprise boswellia extract. The boswellia extract can be present in the formulation, individually, in each case, in an amount of from about 10 mg to about 50 mg. The boswellia extract can be present in the formulation, individually, in each case, in an amount of about 26 mg. The one or more antioxidants can comprise rosemary leaf extract. The rosemary leaf extract can be present in the formulation, individually, in each case, in an amount of from about 10 mg to about 50 mg. The rosemary leaf extract can be present in the formulation, individually, in each case, in an amount of about 24 mg. The one or more antioxidants can comprise ginger root extract. The ginger root extract can be present in the formulation, individually, in each case, in an amount of from about 10 mg to about 80 mg. The ginger root extract can be present in the formulation in an amount of from about 40 mg.

The formulation can comprise optionally soybean oil, optionally flax seed oil, turmeric root extract, boswellia extract, grape seed extract, rosemary leaf extract, cayenne pepper, ginkgo leaf extract, Korean *ginseng* root extract, ginger root extract, citrus bioflavonoids concentrate, and garlic bulb. In the formulation, the flax seed oil can optionally be present in the formulation, individually, in each case, in an amount of from about 10 mg to about 150 mg, the grape seed extract can be present in the formulation, individually, in each case, in an amount of from about 10 mg to about 50 mg, the garlic bulb can be present in the formulation, individually, in each case, in an amount of from about 5 mg to about 50 mg, the ginkgo leaf extract can be present in the formulation, individually, in each case, in an amount of from about 5 mg to about 50 mg or from about 5 mg to about 100 mg, the *ginseng* root extract can be present in the formulation, individually, in each case, in an amount of from about 5 mg to about 50 mg, the turmeric root extract can be present in the formulation, individually, in each case, in an amount of from about 10 mg to about 100 mg or from about 10 mg to about 150 mg, the cayenne pepper can be present in the formulation, individually, in each case, in an amount of from about 10 mg to about 100 mg or from about 5 mg to about 100 mg, the soybean oil can optionally be present in the formulation, individually, in each case, in an amount of from about 10 mg to about 200 mg, the boswellia extract can be present in the formulation, individually, in each case, in an amount of from about 10 mg to about 50 mg, the ginger root extract can be present in the formulation, individually, in each case, in an amount of from about 10 mg to about 80 mg, and the rosemary leaf extract can be present in the formulation, individually, in each case, in an amount of from about 10 mg to about 50 mg. In the formulation, the flax seed oil can optionally be present in the formulation, individually, in each case, in an amount of about 100 mg, the grape seed extract can be present in the formulation, individually, in each case, in an amount of about 25 mg, the garlic bulb can be present in the formulation, individually, in each case, in an amount of about 5 mg, the ginkgo leaf extract can be present in the formulation, individually, in each case, in an amount of about 5 mg or 20 mg, the *ginseng* root extract can be present in the formulation, individually, in each case, in an amount of about 5 mg, the turmeric root extract can be present in the formulation, individually, in each case, in an amount of about 55 mg or about 80 mg, the cayenne pepper can be present in the formulation, individually, in each case, in an amount of about 20 mg, the soybean oil can optionally be present in the formulation, individually, in each case, in an amount of about 120 mg, the boswellia extract can be present in the formulation, individually, in each case, in an amount of about 26 mg, the rosemary leaf extract can be present in the formulation, individually, in each case, in an amount of about 24 mg, and the ginger root extract can be present in the formulation in an amount of from about 40 mg.

In another aspect, the formulation can comprise omega-3 DHA, omega-3 EPA, phosphatidylcholine or a salt thereof, myo-inositol, choline, optionally soy lecithin or a salt thereof, alpha-glycerophosphocholine or a salt thereof, phosphatidylserine or a salt thereof, optionally citicoline or a salt thereof, L-arginine or a salt thereof, L-citrulline or a salt thereof, taurine or a salt thereof, beet root extract, acetyl-L-carnitine or a salt thereof, alpha lipoic acid or a salt thereof, resveratrol or a salt thereof, quercetin or a salt thereof, astaxanthin or a salt thereof, chlorophyll, menaquinone MK7 (K2), CoQ10, optionally soybean oil, optionally flax seed oil, turmeric root extract, boswellia extract, grape seed extract, rosemary leaf extract, cayenne pepper, ginkgo leaf extract, Korean *ginseng* root extract, ginger root extract, citrus bioflavonoids concentrate, and garlic bulb. In the formulation, the omega-3 DHA can be present in the formulation, individually, in each case, in an amount of from about 10 mg to about 500 mg, the omega-3 EPA can be present in the formulation, individually, in each case, in an amount of from about 10 mg to about 200 mg, the myo-inositol can be present in the formulation, individually, in each case, in an amount of from about 10 mg to about 160 mg, the phosphatidylcholine or a salt thereof can be present in the formulation, individually, in each case, in an amount of from about 10 mg to about 300 mg or about 1 mg to about 300 mg, the phosphatidylserine or a salt thereof can be present in the formulation, individually, in each case, in an amount of from about 6 mg to about 20 mg or from about 1 mg to about 20 mg, the alpha-glycerophosphocholine or a salt thereof can be present in the formulation, individually, in each case, in an amount of from about 6 mg to about 20 mg or from about 1 mg to about 20 mg, the citicoline or a salt thereof can optionally be present in the formulation, individually, in each case, in an amount of from about 5 mg to about 30 mg or from about 1 mg to about 30 mg, the choline can be present in the formulation, individually, in each case, in an amount of from about 10 mg to about 100 mg or from about 10 mg to about 200 mg, the soy lecithin or a salt thereof can optionally be present in the formulation, individually, in each case, in an amount of from about 10 mg to about 100 mg, the acetyl-L-carnitine or a salt thereof can be present in the formulation, individually, in each case, in an amount of from about 10 mg to about 50 mg, the taurine or a salt thereof can be present in the formulation, individually, in each case, in an amount of from about 10 mg to about 80 mg, the alpha lipoic acid or a salt thereof can be present in the formulation, individually, in each case, in an amount of from about 10 mg to about 50 mg, the resveratrol or a salt thereof can be present in the formulation, individually, in each case, in an amount of from about 10 mg to about 50 mg, the quercetin or a salt thereof can be present in the formulation, individually, in each case, in an amount of from about 0.5 mg to about 5 mg or from about 0.5 mg to about 10 mg, the astaxanthin or a salt thereof can be present in the formulation, individually, in each case, in an amount of from about 0.5 mg to about 4 mg or from about 0.1 mg to about 4 mg, the chlorophyll or a salt thereof can be present in the formulation, individually, in each case, in an amount from about 0.1 mg to about 5 mg, the menaquinone MK7 (K2) or a salt thereof can be present in the formulation, individually, in each case, in an amount from about 0.001 mg to about 0.1 mg, the CoQ10 can be present in the formulation, individually, in each case, in an amount of from about 0.01 mg to about 4 mg, the L-arginine can be present as a hydrochloric acid salt in the formulation, individually, in each case, in an amount of from about 10 mg to about 100 mg, the L-citrulline or a salt thereof can be present in the formulation, individually, in each case, in an amount of from about 8 mg to about 80 mg, the beet root extract can be present in the formulation, individually, in each case, in an amount of from about 8 mg to about 80 mg, the flax seed oil can optionally be present in the formulation, individually, in each case, in an amount of from about 10 mg to about 150 mg, the grape seed extract can be present in the formulation, individually, in each case, in an amount of from about 10 mg to about 50 mg, the garlic bulb can be present in the formulation, individually, in each case, in an amount of from about 5 mg to about 50 mg, the ginkgo leaf extract can be present in the formulation, individually, in each case, in an amount of from about 5 mg to about 50 mg or from about 5 mg to about 100 mg, the *ginseng* root extract can be present in the formulation, individually, in each case, in an amount of from about 5 mg to about 50 mg, the turmeric root extract can be present in the formulation, individually, in each case, in an amount of from about 10 mg to about 100 mg or from about 10 mg to about 150 mg, the cayenne pepper can be present in the formulation, individually, in each case, in an amount of from about 10 mg to about 100 mg or about 5 mg to about 100 mg, the soybean oil can optionally be present in the formulation, individually, in each case, in an amount of from about 10 mg to about 200 mg, the boswellia extract can be present in the formulation, individually, in each case, in an amount of from about 10 mg to about 50 mg, the ginger root extract can be present in the formulation in an amount of from about 40 mg, and the rosemary leaf extract can be present in the formulation, individually, in each case, in an amount of from about 10 mg to about 50 mg.

In the formulation, the omega-3 DHA can be present in the formulation, individually, in each case, in an amount of about 250 mg or 180 mg, the omega-3 EPA can be present in the formulation, individually, in each case, in an amount of about 100 mg or 30 mg, the myo-inositol can be present in the formulation, individually, in each case, in an amount of about 80 mg, the phosphatidylcholine or a salt thereof can be present in the formulation, individually, in each case, in an amount of about 148 mg or about 20 mg, the phosphatidylserine or a salt thereof can be present in the formulation, individually, in each case, in an amount of about 6 mg, the alpha-glycerophosphocholine or a salt thereof can be present in the formulation, individually, in each case, in an amount of about 6 mg, the citicoline or a salt thereof can optionally be present in the formulation, individually, in each case, in an amount of about 5 mg or about 3 mg, the choline can be present in the formulation, individually, in each case, in an amount of about 55 mg or 110 mg, the soy lecithin or a salt thereof can optionally be present in the formulation, individually, in each case, in an amount of about 20 mg, the acetyl-L-carnitine or a salt thereof can be present in the formulation, individually, in each case, in an amount of about 25 mg, the taurine or a salt thereof can be present in the formulation, individually, in each case, in an amount of about 40 mg, the alpha lipoic acid or a salt thereof can be present in the formulation, individually, in each case, in an amount of about 25 mg, the resveratrol or a salt thereof can be present in the formulation, individually, in each case, in an amount of about 20 mg, the quercetin or a salt thereof can be present in the formulation, individually, in each case, in an amount of about 5 mg, the astaxanthin or a salt thereof can be present in the formulation, individually, in each case, in an amount of about 1 mg, the chlorophyll or a salt thereof can be present in the formulation, individually, in each case, in an amount of about 2 mg, the menaquinone MK7 (K2) or a salt thereof can be present in the formulation, individually, in each case, in an amount of about 0.01 mg, the CoQ10 can be present in the formulation, individually, in each case, in an amount of about 0.5 mg, the L-arginine can be present as a hydrochloric acid salt in the formulation, individually, in each case, in an amount of about 55 mg, the L-citrulline or a salt thereof can be present in the formulation, individually, in each case, in an amount of about 40 mg, the beet root extract can be present in the formulation, individually, in each case, in an amount of about 40 mg, the flax seed oil can optionally be present in the formulation, individually, in each case, in an amount of about 100 mg, the grape seed extract can be present in the formulation, individually, in each case, in an amount of about 25 mg, the garlic bulb can be present in the formulation, individually, in each case, in an amount of about 5 mg, the ginkgo leaf extract can be present in the formulation, individually, in each case, in an amount of about 5 mg or about 20 mg, the *ginseng* root extract can be present in the formulation, individually, in each case, in an amount of about 5 mg, the turmeric root extract can be present in the formulation, individually, in each case, in an amount of about 55 mg or about 80 mg, the cayenne pepper can be present in the formulation, individually, in each case, in an amount of about 20 mg, the soybean oil can optionally be present in the formulation, individually, in each case, in an amount of about 120 mg, the boswellia extract can be present in the formulation, individually, in each case, in an amount of about 26 mg, the ginger root extract can be present in the formulation in an amount of from about 40 mg, and the rosemary leaf extract can be present in the formulation, individually, in each case, in an amount of about 24 mg.

The formulation can be formulated as a capsule, tablet, juice, powder, suspension, emulsifier, granules, troch, pill, suspension, spirit, and syrup. The formulation can be contained in capsules. Capsules suitable for oral administration can include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. The formulation can be a heterogeneous mixture. The formulation can be a homogenous mixture.

The formulation can further comprise physiologically or pharmaceutically acceptable excipients. Excipients can be selected to provide formulations for specific routes of administration and/or other types of administration, e.g., administration by tablet, capsule, or liquid dose. The excipient can be selected from the group consisting of vegetable oil, cellulose (cellulose gum), stearic acid, silicon dioxide (bamboo extract), magnesium stearate, titanium dioxide, natural vanillin and peppermint, polyethylene glycol, riboflavin, chlorophyll, carnauba wax, and any combination thereof.

The formulation can be contained in a container. The formulation can retain at least about 80% of supplement activity for at least a year when stored in a sealed container, wherein the sealed container can be placed in an environment having a temperature of about 25° C. and about 50% relative humility. The formulation can retain at least about 70% of supplement activity for at least a year when stored in a sealed container, wherein the sealed container can be placed in an environment having a temperature of about 25° C. and about 40% relative humility. The formulation can retain at least about 90% of supplement activity for at least two years when stored in a sealed container, wherein the sealed container can be placed in an environment having a temperature of about 25° C. and about 50% relative humility. The formulation can retain at least about 95% of supplement activity for at least two years when stored in a sealed container, wherein the sealed container can be placed in an environment having a temperature of about 25° C. and about 50% relative humility. Any formulation disclosed herein can be administered at least about once a day, twice a day, three times a day, four times a day, or more often.

At least one formulation disclosed herein can be suitable for supporting, controlling, restoring, maintaining or enhancing a healthy nervous system. At least one formulation disclosed herein can be suitable for supporting, controlling, restoring, maintaining or enhancing memory performance in a subject. At least one formulation disclosed herein can be suitable for supporting, controlling, restoring, maintaining or enhancing neuro-protection, brain function and memory, natural nerve transmission, or GABA. At least one formulation disclosed herein can be suitable for supporting, controlling, restoring, maintaining or enhancing healthy stress responses, natural stress responses, or physical and mental well-being health. At least one formulation disclosed herein can be suitable for supporting, controlling, restoring, maintaining or enhancing respiratory health. At least one formulation disclosed herein can be suitable for supporting, controlling, restoring, maintaining or enhancing appetite control or weight control. At least one formulation disclosed herein can be suitable for supporting, controlling, restoring, maintaining or enhancing, homocysteine levels, natural production of nucleic acids and creatine phosphate, the manufacture and utilization of carbohydrates, fats, and amino acids, natural protein synthesis, natural enzymatic reactions, or chemical reactions. At least one formulation disclosed herein can be suitable for supporting, controlling, restoring, maintaining or enhancing detoxification or neutralization of toxin. At least one formulation disclosed herein can be suitable for supporting, controlling, restoring, maintaining or enhancing antioxidant health or natural glutathione levels. At least one formulation disclosed herein can be suitable for supporting, controlling, restoring, maintaining or enhancing energy levels (stamina). At least one formulation disclosed herein can be suitable for supporting, controlling, restoring, maintaining or enhancing natural pH levels. At least one formulation disclosed herein can be suitable for supporting, controlling, restoring, maintaining or enhancing natural recovery time. At least one formulation disclosed herein can be suitable for supporting, controlling, restoring, maintaining or enhancing metabolism health. At least one formulation disclosed herein can be suitable for supporting, controlling, restoring, maintaining or enhancing natural tryptophan metabolism, natural blood sugar metabolism, or methionine metabolism. At least one formulation disclosed herein can be suitable for supporting, controlling, restoring, maintaining or enhancing natural thermogenesis. At least one formulation disclosed herein can be suitable for supporting, controlling, restoring, maintaining or enhancing natural cell division. At least one formulation disclosed herein can be suitable for supporting, controlling, restoring, maintaining or enhancing the immune system health. At least one formulation disclosed herein can be suitable for supporting, controlling, restoring, maintaining or enhancing healthy uric acid levels. At least one formulation can be suitable for controlling stress. At least one formulation can be suitable for relieving stress. At least one formulation disclosed herein can be suitable for supporting, controlling, restoring, maintaining or enhancing cognitive performance in a subject.

At least one formulation disclosed herein can be suitable for supporting, controlling, restoring, maintaining or enhancing heart and cardiovascular health. At least one formulation disclosed herein can be suitable for supporting, controlling, restoring, maintaining or enhancing healthy red blood cells, natural white blood cell levels, natural heme production, small blood vessel health, healthy blood pressure levels, or platelet function. At least one formulation disclosed herein can be suitable for supporting, controlling, restoring, maintaining or enhancing blood circulation in a subject. At least one formulation disclosed herein can be suitable for supporting, controlling, restoring, maintaining or enhancing adsorption of nutrients in a subject.

At least one formulation disclosed herein can be suitable for reducing the need for insulin administration. At least one formulation disclosed herein can be used for hippocampus rehabilitation. At least one formulation disclosed herein can be suitable for supporting, controlling, restoring, maintaining or enhancing blood sugar metabolism. At least one formulation disclosed herein can be suitable for stabilizing or reducing hemoglobin A1C levels. At least one formulation disclosed herein can be suitable for supporting, controlling, restoring, maintaining or enhancing liver function in a subject. At least one formulation disclosed herein can be suitable for supporting, controlling, restoring, maintaining or enhancing gall bladder function in a subject. At least one formulation disclosed herein can be suitable for supporting, controlling, restoring, maintaining or enhancing liver detoxification in a subject. At least one formulation disclosed herein can be suitable for supporting, controlling, restoring, maintaining or enhancing the immune system in a subject. At least one formulation disclosed herein can be suitable for supporting, controlling, restoring, maintaining or enhancing healthy brain function in a subject. At least one formulation disclosed herein can be suitable for supporting, controlling, restoring, maintaining or enhancing digestion in a subject. At least one formulation disclosed herein can be suitable for supporting, controlling, restoring, maintaining or enhancing platelet activity in a subject.

At least one formulation disclosed herein can be suitable for supporting, controlling, restoring, maintaining or enhancing blood sugar metabolism. At least one formulation disclosed herein can be suitable for supporting, controlling, restoring, maintaining or enhancing blood sugar in a subject with insufficient insulin. At least one formulation disclosed herein can be suitable for supporting, controlling, restoring, maintaining or enhancing liver function. At least one formulation disclosed herein can be suitable for supporting, controlling, restoring, maintaining or enhancing normal cholesterol level. At least one formulation disclosed herein can be suitable for supporting, controlling, restoring, maintaining or enhancing red blood cell formation. At least one formulation disclosed herein can be suitable for supporting, controlling, restoring, maintaining or enhancing a healthy salt balance within the body fluid. At least one formulation disclosed herein can be suitable for supporting, controlling, restoring, maintaining or enhancing gastrointestinal health. At least one formulation disclosed herein can be suitable for supporting, controlling, restoring, maintaining or enhancing gall bladder function. At least one formulation disclosed herein can be suitable for supporting, controlling, restoring, maintaining or enhancing liver detoxification. At least one formulation disclosed herein can be suitable for supporting, controlling, restoring, maintaining or enhancing the immune system. At least one formulation disclosed herein can be suitable for supporting, controlling, restoring, maintaining or enhancing a healthy brain function. At least one formulation disclosed herein can be suitable for supporting, controlling, restoring, maintaining or enhancing digestion. At least one formulation disclosed herein can be suitable for supporting, controlling, restoring, maintaining or enhancing platelet activity. At least one formulation disclosed herein can be suitable for supporting, controlling, restoring, maintaining or enhancing healthy adrenal feedback loop function. At least one formulation disclosed herein can be suitable for supporting, controlling, restoring, maintaining or enhancing a normal sleep pattern. At least one formulation disclosed herein formulation can be suitable for supporting, controlling, restoring, maintaining or enhancing mental alertness or wakefulness. At least one formulation disclosed herein formulation can be suitable for supporting, controlling, restoring, maintaining or enhancing normal bone density. At least one formulation disclosed herein formulation can be suitable for supporting, controlling, restoring, maintaining or enhancing hormonal balance. At least one formulation can be suitable for supporting, controlling, restoring, maintaining or enhancing cognitive function. At least one formulation can be suitable for supporting, controlling, restoring, maintaining or enhancing thyroid function. At least one formulation can be suitable for supporting, controlling, restoring, maintaining or enhancing normal menstruation. At least one formulation can be suitable for supporting, controlling, restoring, maintaining or enhancing joint health. At least one formulation can be suitable for supporting, controlling, restoring, maintaining or enhancing insulin receptor function. At least one formulation can be suitable for supporting, controlling, restoring, maintaining or enhancing healthy arterial wall. At least one formulation can be suitable for supporting, controlling, restoring, maintaining or enhancing a healthy heart function. At least one formulation can be suitable for supporting, controlling, restoring, maintaining or enhancing DNA repair function. At least one formulation can be suitable for supporting, controlling, restoring, maintaining or enhancing dopamine production and function.

At least one formulation disclosed herein can be suitable for supporting, controlling, restoring, maintaining or enhancing the health of those suffering from diabetes (or complication from diabetes) or those who can be predisposed to pre-diabetes. At least one formulation disclosed herein can be suitable for supporting, controlling, restoring, maintaining or enhancing the health of those concerned with maintaining proper blood sugar control or those who currently have normal blood sugar but who have a history of blood sugar control problem.

At least one formulation disclosed herein can be suitable for supporting, controlling, restoring, maintaining or enhancing organ health. At least one formulation disclosed herein can be suitable for supporting, controlling, restoring, maintaining or enhancing the health of the circulatory system, eyes, ears, skin, mouth (oral), soft tissue, scalp, skeletal tissue, cartilage, connective tissue, liver, kidney, gall bladder, muscle, bone, joint, hair, nails, musculoskeletal, or mucous membranes. At least one formulation disclosed herein can be suitable for supporting, controlling, restoring, maintaining or enhancing natural bone growth, natural growth and repair of tissues, gene expression, cellular repair, or health and integrity of cellular tissue.

At least one formulation disclosed herein can be suitable for supporting, controlling, restoring, maintaining or enhancing reproductive health. At least one formulation disclosed herein can be suitable for supporting, controlling, restoring, maintaining or enhancing female reproductive health, male reproductive health, menstruation health, or male sexual function health.

At least one formulation disclosed herein can be suitable for supporting, controlling, restoring, maintaining or enhancing hormone health. At least one formulation disclosed herein can be suitable for supporting, controlling, restoring, maintaining or enhancing hormone health in a subject suffering from Polycystic Ovarian Syndrome (PCOS). At least one formulation disclosed herein can be suitable for supporting, controlling, restoring, maintaining or enhancing adrenal function or adrenal hormones.

At least one formulation disclosed herein can be suitable for supporting, controlling, restoring, maintaining or enhancing healthy cholesterol levels. At least one formulation disclosed herein can be suitable for supporting, controlling, restoring, maintaining or enhancing triglyceride levels, natural breakdown of fats, or natural biliary levels. At least one formulation disclosed herein can be suitable for supporting, controlling, restoring, maintaining or enhancing digestive health. At least one formulation disclosed herein can be suitable for supporting, controlling, restoring, maintaining or enhancing colon health, nutrient transportation, intestinal health, natural absorption of minerals, or natural nutrient utilization.

Methods of Making and Administering Dietary Supplements

In an aspect, a method can comprise orally administering the supplement formulation in unit dose form to a human. A method can be a method of supporting cognitive health of the human. A method can be a method of supporting clarity, supporting concentration, or supporting clarity and concentration of the human. A method can be a method of boosting alertness, boosting wakefulness, or boosting alertness and wakefulness of the human.

In some embodiments, a method can comprise administering a supplement that comprises amino acids, agents to maintain healthy cognitive function, adaptogens, antioxidants, agents to maintain healthy absorption of nutrients, and combinations thereof. In some embodiments, method comprises administering an effective amount of the supplement to have a synergistic effect that enhances the cognitive health of a human. In some embodiments, a method comprises administering an effective amount of the supplement to have an effect of supporting clarity, supporting concentration, or supporting clarity and concentration of a human. In some embodiments, method comprises administering an effective amount of the supplement to have an effect of boosting alertness, boosting wakefulness, or boosting alertness and wakefulness of a human. In some embodiments, a method comprises administering a serving of the formulation one time per day. In some embodiments, a method comprises administering a serving of the formulation two times per day. In some embodiments, a method comprises administering a serving of the formulation three times per day. In some embodiments, a method comprises administering a serving of the formulation four times per day. In some embodiments, a population that was administered a method described herein reported, including, but not limited to, improved focus, clarity, and concentration. In some embodiments, a population that was administered a method described herein reported, including, but not limited to, improved speed of cognition and information processing. In some embodiments, a population that was administered a method described herein reported, including, but not limited to, improved alertness, energy, and focus.

In another aspect, a method of making a supplement formulation in unit dose form can comprise combining one or more adaptogens, one or more antioxidants, an agent to maintain healthy absorption of nutrients, and an agent to maintain healthy cognitive function. In another aspect, a method of making a supplement formulation in unit dose form can comprise combining one or more adaptogens, one or more antioxidants, an agent to maintain healthy absorption of nutrients, and an agent to maintain healthy cognitive function, wherein the agent to maintain healthy cognitive function can be present in the formulation, individually, in each case, in an amount of from about 0.5 mg to about 4 mg. A method of making a supplement formulation in unit dose form can comprise combining *ginseng* root, ginkgo leaf extract, ginger root extract, cayenne pepper, *rhodiola* root extract, and green tea leaf extract. A method of making a supplement formulation in unit dose form can comprise combining *ginseng* root, ginkgo leaf extract, ginger root extract, cayenne pepper, *rhodiola* root extract, and green tea leaf extract, wherein the green tea leaf extract can be present in the formulation in an amount of from about 50 mg to about 600 mg.

A method of making a supplement formulation in unit dose form can comprise combining an antioxidant, one or more compounds to maintain healthy cognitive performance, and an amino acid or a salt thereof. A method of making a supplement formulation in unit dose form can comprise combining an antioxidant, one or more compounds to maintain healthy cognitive performance, and an amino acid or a salt thereof, wherein the amino acid or a salt thereof can be present in the formulation, individually, in each case, in an amount of from about 10 mg to about 400 mg. A method of making a supplement formulation in unit dose form can comprise combining bacopa leaf extract, L-theanine or a salt thereof, resveratrol or a salt thereof, dimethylaminoethanol or a salt thereof, pyrroloquinoline quinone or a salt thereof, and optionally huperzine A or a salt thereof. A method of making a supplement formulation in unit dose form can comprise combining bacopa leaf extract, L-theanine or a salt thereof, resveratrol or a salt thereof, dimethylaminoethanol or a salt thereof, pyrroloquinoline quinone or a salt thereof, and optionally huperzine A or a salt thereof, wherein the L-theanine can be present in the formulation in an amount of from about 10 mg to about 400 mg.

A method of making a supplement formulation in unit dose form can comprise combining an energy recycler, a first amino acid or a salt thereof, a second amino acid or a salt thereof, a third amino acid or a salt thereof, a fourth amino acid or a salt thereof, and an antioxidant. A method of making a supplement formulation in unit dose form can comprise combining an energy recycler, a first amino acid or a salt thereof, a second amino acid or a salt thereof, a third amino acid or a salt thereof, a fourth amino acid or a salt thereof, and an antioxidant, wherein the antioxidant can be present in the formulation, individually, in each case, in an amount of from about 10 mg to about 150 mg. A method of making a supplement formulation in unit dose form can comprise combining DL-phenylalanine or a salt thereof, L-tyrosine or a salt thereof, L-arginine or a salt thereof, taurine or a salt thereof, 5-hydroxytryptophan or a salt thereof, and creatine or a salt thereof. A method of making a supplement formulation in unit dose form can comprise combining DL-phenylalanine or a salt thereof, L-tyrosine or a salt thereof, L-arginine or a salt thereof, taurine or a salt thereof, 5-hydroxytryptophan or a salt thereof, and creatine or a salt thereof, wherein the taurine or a salt thereof can be present in the formulation, individually, in each case, in an amount of from about 10 mg to about 150 mg.

In another aspect, a method of making a supplement formulation in unit dose form can comprise combining one or more adaptogens, one or more antioxidants, an agent to maintain healthy absorption of nutrients, an agent to maintain healthy cognitive function, one or more compounds to maintain healthy cognitive performance, one or more amino acids or salts thereof, and an energy recycler. In another aspect, a method of making a supplement formulation in unit dose form can comprise combining one or more adaptogens, one or more antioxidants, an agent to maintain healthy absorption of nutrients, an agent to maintain healthy cognitive function, one or more compounds to maintain healthy cognitive performance, one or more amino acids or salts thereof, and an energy recycler, wherein the antioxidant can be present in the formulation, individually, in each case, in an amount of from about 10 mg to about 150 mg.

In another aspect, a method of making a supplement formulation in unit dose form can comprise combining *ginseng* root, ginkgo leaf extract, ginger root extract, cayenne pepper, *rhodiola* root extract, green tea leaf extract, bacopa leaf extract, L-theanine or a salt thereof, resveratrol or a salt thereof, dimethylaminoethanol or a salt thereof, pyrroloquinoline quinone or a salt thereof, optionally huperzine A or a salt thereof, DL-phenylalanine or a salt thereof, L-tyrosine or a salt thereof, L-arginine or a salt thereof, taurine or a salt thereof, 5-hydroxytryptophan or a salt thereof, and creatine or a salt thereof. In another aspect, a method of making a supplement formulation in unit dose form can comprise combining *ginseng* root, ginkgo leaf extract, ginger root extract, cayenne pepper, *rhodiola* root extract, green tea leaf extract, bacopa leaf extract, L-theanine or a salt thereof, resveratrol or a salt thereof, dimethylaminoethanol or a salt thereof, pyrroloquinoline quinone or a salt thereof, optionally huperzine A or a salt thereof, DL-phenylalanine or a salt thereof, L-tyrosine or a salt thereof, L-arginine or a salt thereof, taurine or a salt thereof, 5-hydroxytryptophan or a salt thereof, and creatine or a salt thereof, wherein the *rhodiola* root extract can be present in the formulation in an amount of from about 0.5 mg to about 4 mg.

In another aspect, a method can comprise orally administering the formulation in unit dose form to a human. The method can be a method of promoting or encouraging sleep. The method can be a method of supporting health, supporting well-being, or supporting health and well-being of the human. The method can be a method of helping the human wake up feeling refreshed. The method can be a method of enabling rejuvenated mornings for the human. The method can be a method of supporting cognitive health in the human. The method can be a method of conferring a state of relaxation and balance on the human.

In some embodiments, the method can comprise administering a supplement that comprises amino acids, agents to maintain healthy cognitive function, antioxidants, agents to maintain healthy brain function, precursors for neurotransmitters, agents to promote or encourage healthy sleep, and combinations thereof. In some embodiments, the method comprises administering an effective amount of the supplement to have a synergistic effect that promotes sleep in a human. In some embodiments, method comprises administering an effective amount of the supplement to have an effect of supporting health, supporting well-being, or supporting health and well-being of a human. In some embodiments, method comprises administering an effective amount of the supplement to have an effect of helping a human wake up feeling refreshed. In some embodiments, method comprises administering an effective amount of the supplement to have an effect of enabling rejuvenated mornings for a human. In some embodiments, method comprises administering an effective amount of the supplement to have an effect supporting cognitive health in a human. In some embodiments, method comprises administering an effective amount of the supplement to have an effect of conferring a state of relaxation and balance on a human. In some embodiments, the method comprises administering a serving of the formulation one time per day. In some embodiments, the method comprises administering a serving of the formulation two times per day. In some embodiments, a population that was administered the method reported, including, but not limited to, improved sleep quality. In some embodiments, a population that was administered the method reported, including, but not limited to, improved wakefulness and alertness. In some embodiments, a population that was administered the method reported, including, but not limited to, reduced stress and anxiety.

A method of making a supplement formulation in unit dose form can comprise combining a first amino acid or a salt thereof, a second amino acid or a salt thereof, an antioxidant, a precursor for a neurotransmitter, an agent to promote or encourage healthy sleep, an agent to maintain healthy cognitive function, and a compound to help maintain healthy brain function. A method of making a supplement formulation in unit dose form can comprise combining a first amino acid or a salt thereof, a second amino acid or a salt thereof, an antioxidant, a precursor for a neurotransmitter, an agent to promote or encourage healthy sleep, an agent to maintain healthy cognitive function, and a compound to help maintain healthy brain function, wherein the compound to help maintain healthy brain function can be present in the formulation, individually, in each case, in an amount of from about 8 mg to about 40 mg. A method of making a supplement formulation in unit dose form can comprise combining GABA or a salt thereof, L-theanine or a salt thereof, taurine or a salt thereof, L-glutamine or a salt thereof, myo-inositol, melatonin or a salt thereof, and phosphatidylserine or a salt thereof. A method of making a supplement formulation in unit dose form can comprise combining GABA or a salt thereof, L-theanine or a salt thereof, taurine or a salt thereof, L-glutamine or a salt thereof, myo-inositol, melatonin or a salt thereof, and phosphatidylserine or a salt thereof, wherein the myo-inositol can be present in the formulation in an amount of from about 8 mg to about 40 mg.

A method of making a supplement formulation in unit dose form can comprise combining one or more compounds to promote or encourage healthy sleep, a precursor for a neurotransmitter, and an antioxidant. A method of making a supplement formulation in unit dose form can comprise combining one or more compounds to promote or encourage healthy sleep, a precursor for a neurotransmitter, and an antioxidant, wherein the antioxidant can be present in the formulation, individually, in each case, in an amount of from about 8 mg to about 60 mg. A method of making a supplement formulation in unit dose form can comprise combining valerian root extract, 5-hydroxytryptophan or a salt thereof, ashwagandha root extract, chamomile flower extract, hops flower extract, passion flower extract, and lemon balm leaf extract. A method of making a supplement formulation in unit dose form can comprise combining valerian root extract, 5-hydroxytryptophan or a salt thereof, ashwagandha root extract, chamomile flower extract, hops flower extract, passion flower extract, and lemon balm leaf extract, wherein the ashwagandha root extract can be present in the formulation, individually, in each case, in an amount of from about 8 to about 60 mg.

A method of making a supplement formulation in unit dose form can comprise combining a first amino acid or a salt thereof, a second amino acid or a salt thereof, one or more antioxidants, one or more precursors for neurotransmitters, one or more agents to promote or encourage healthy sleep, an agent to maintain healthy cognitive function, and a compound to help maintain healthy brain function. A method of making a supplement formulation in unit dose form can comprise combining a method of making a supplement formulation in unit dose form can comprise combining a first amino acid or a salt thereof, a second amino acid or a salt thereof, one or more antioxidants, one or more precursors for neurotransmitters, one or more agents to promote or encourage healthy sleep, an agent to maintain healthy cognitive function, and a compound to help maintain healthy brain function, wherein the compound to help maintain healthy brain function can be present in the formulation, individually, in each case, in an amount of from about 8 mg to about 40 mg. In another aspect, a method of making a supplement formulation in unit dose form can comprise combining GABA or a salt thereof, L-theanine or a salt thereof, taurine or a salt thereof, L-glutamine or a salt thereof, myo-inositol, melatonin or a salt thereof, phosphatidylserine or a salt thereof, valerian root extract, 5-hydroxytryptophan or a salt thereof, ashwagandha root extract, chamomile flower extract, hops flower extract, passion flower extract, and lemon balm leaf extract. In another aspect, a method of making a supplement formulation in unit dose form can comprise combining GABA or a salt thereof, L-theanine or a salt thereof, taurine or a salt thereof, L-glutamine or a salt thereof, myo-inositol, melatonin or a salt thereof, phosphatidylserine or a salt thereof, valerian root extract, 5-hydroxytryptophan or a salt thereof, ashwagandha root extract, chamomile flower extract, hops flower extract, passion flower extract, and lemon balm leaf extract, wherein the myo-inositol can be present in the formulation in an amount of from about 8 mg to about 40 mg.

In another aspect, a method can comprise orally administering the formulation in unit dose form to a human. The method can be a method of supporting brain health of the human. The method can be a method of supporting energy, supporting vitality, or supporting energy and vitality of the human. The method can be a method of supporting a healthy lifestyle, supporting well-being, or supporting a healthy lifestyle and well-being of the human.

In some embodiments, the method can comprise administering a supplement that comprises amino acids, agents to maintain healthy cognitive function, agents to help maintain healthy blood circulation, agents to maintain healthy absorption of nutrients, agents to maintain healthy heart function, ingredients to help maintain healthy memory performance, antioxidants, agents to maintain healthy brain function, precursors for neurotransmitters, agents to help maintain healthy blood circulation, and combinations thereof. In some embodiments, the method comprises administering an effective amount of the supplement to have a synergistic effect supporting brain health of a human. In some embodiments, method comprises administering an effective amount of the supplement to have an effect of supporting energy, supporting vitality, or supporting energy and vitality of a human. In some embodiments, method comprises administering an effective amount of the supplement to have an effect of supporting a healthy lifestyle, supporting well-being, or supporting a healthy lifestyle and well-being of a human. In some embodiments, the method comprises administering a serving of the formulation one time per day. In some embodiments, the method comprises administering a serving of the formulation two times per day. In some embodiments, a population that was administered the method reported, including, but not limited to, feeling more energetic. In some embodiments, a population that was administered the method reported, including, but not limited to, enhanced cognitive function. In some embodiments, a population that was administered the method reported, including, but not limited to, improved mental performance.

A method of making a supplement formulation in unit dose form can comprise combining one or more agents to maintain healthy cognitive function, one or more ingredients to help maintain healthy memory performance, and a compound to help maintain healthy brain function. A method of making a supplement formulation in unit dose form can comprise combining one or more agents to maintain healthy cognitive function, one or more ingredients to help maintain healthy memory performance, and a compound to help maintain healthy brain function, wherein the compound to help maintain healthy brain function can be present in the formulation, individually, in each case, in an amount of from about 10 mg to about 160 mg. A method of making a supplement formulation in unit dose form can comprise combining phosphatidylcholine or a salt thereof, myo-inositol, choline, optionally soy lecithin or a salt thereof, alpha-glycerophosphocholine or a salt thereof, phosphatidylserine or a salt thereof, and optionally citicoline or a salt thereof. A method of making a supplement formulation in unit dose form can comprise combining phosphatidylcholine or a salt thereof, myo-inositol, choline, optionally soy lecithin or a salt thereof, alpha-glycerophosphocholine or a salt thereof, phosphatidylserine or a salt thereof, and optionally citicoline or a salt thereof, wherein the myo-inositol can be present in the formulation, individually, in each case, in an amount of from about 10 mg to about 160 mg.

A method of making a supplement formulation in unit dose form can comprise combining one or more antioxidants, an amino acid or a salt thereof, one or more agents to help maintain healthy blood circulation, and a compound to help maintain healthy brain function. A method of making a supplement formulation in unit dose form can comprise combining one or more antioxidants, an amino acid or a salt thereof, one or more agents to help maintain healthy blood circulation, and a compound to help maintain healthy brain function, wherein the compound to help maintain healthy brain function can be present in the formulation, individually, in each case, in an amount of from about 10 mg to about 50 mg. A method of making a supplement formulation in unit dose form can comprise combining L-arginine or a salt thereof, L-citrulline or a salt thereof, taurine or a salt thereof, beet root extract, acetyl-L-carnitine or a salt thereof, alpha lipoic acid or a salt thereof, resveratrol or a salt thereof, quercetin or a salt thereof, astaxanthin or a salt thereof, and CoQ10. A method of making a supplement formulation in unit dose form can comprise combining L-arginine or a salt thereof, L-citrulline or a salt thereof, taurine or a salt thereof, beet root extract, acetyl-L-carnitine or a salt thereof, alpha lipoic acid or a salt thereof, resveratrol or a salt thereof, quercetin or a salt thereof, astaxanthin or a salt thereof, chlorophyll or a salt thereof, menaquinone MK7 (K2) or a salt thereof, and CoQ10, wherein the acetyl-L-carnitine or a salt thereof can be present in the formulation, individually, in each case, in an amount of from about 10 mg to about 50 mg.

A method of making a supplement formulation in unit dose form can comprise combining one or more antioxidants, one or more adaptogens, an agent to help maintain healthy blood circulation, an agent to maintain healthy absorption of nutrients, and an agent to maintain healthy heart function. A method of making a supplement formulation in unit dose form can comprise combining one or more antioxidants, one or more adaptogens, an agent to help maintain healthy blood circulation, an agent to maintain healthy absorption of nutrients, and an agent to maintain healthy heart function, wherein the agent to maintain healthy heart function can be present in the formulation, individually, in each case, in an amount of from about 10 mg to about 150 mg. A method of making a supplement formulation in unit dose form can comprise combining optionally soybean oil, optionally flax seed oil, turmeric root extract, boswellia extract, grape seed extract, rosemary leaf extract, cayenne pepper, ginkgo leaf extract, Korean *ginseng* root extract, ginger root extract, citrus bioflavonoids concentrate, and garlic bulb. A method of making a supplement formulation in unit dose form can comprise combining optionally soybean oil, optionally flax seed oil, turmeric root extract, boswellia extract, grape seed extract, rosemary leaf extract, cayenne pepper, ginkgo leaf extract, Korean *ginseng* root extract, ginger root extract, citrus bioflavonoids concentrate, and garlic bulb, wherein the flax seed oil can optionally be present in the formulation, individually, in each case, in an amount of from about 10 mg to about 150 mg.

A method of making a supplement formulation in unit dose form can comprise combining one or more agents to maintain healthy cognitive function, one or more ingredients to help maintain healthy memory performance, a compound to help maintain healthy brain function, one or more antioxidants, one or more adaptogens, an agent to help maintain healthy blood circulation, an agent to maintain healthy adsorption of nutrients, an amino acid or a salt thereof, and an agent to maintain healthy heart function. A method of making a supplement formulation in unit dose form can comprise combining one or more agents to maintain healthy cognitive function, one or more ingredients to help maintain healthy memory performance, a compound to help maintain healthy brain function, one or more antioxidants, one or more adaptogens, an agent to help maintain healthy blood circulation, an agent to maintain healthy adsorption of nutrients, an amino acid or a salt thereof, and an agent to maintain healthy heart function, wherein the compound to help maintain healthy brain function can be present in the formulation, individually, in each case, in an amount of from about 10 mg to about 160 mg.

A method of making a supplement formulation in unit dose form can comprise combining omega-3 DHA, omega-3 EPA, phosphatidylcholine or a salt thereof, myo-inositol, choline, optionally soy lecithin or a salt thereof, alpha-glycerophosphocholine or a salt thereof, phosphatidylserine or a salt thereof, optionally citicoline or a salt thereof, L-arginine or a salt thereof, L-citrulline or a salt thereof, taurine or a salt thereof, beet root extract, acetyl-L-carnitine or a salt thereof, alpha lipoic acid or a salt thereof, resveratrol or a salt thereof, quercetin or a salt thereof, astaxanthin or a salt thereof, chlorophyll or a salt thereof, menaquinone MK7 (K2) or a salt thereof, CoQ10, optionally soybean oil, optionally flax seed oil, turmeric root extract, boswellia extract, grape seed extract, rosemary leaf extract, cayenne pepper, ginkgo leaf extract, Korean *ginseng* root extract, and garlic bulb. A method of making a supplement formulation in unit dose form can comprise combining omega-3 DHA, omega-3 EPA, phosphatidylcholine or a salt thereof, myo-inositol, choline, optionally soy lecithin or a salt thereof, alpha-glycerophosphocholine or a salt thereof, phosphatidylserine or a salt thereof, optionally citicoline or a salt thereof, L-arginine or a salt thereof, L-citrulline or a salt thereof, taurine or a salt thereof, beet root extract, acetyl-L-carnitine or a salt thereof, alpha lipoic acid or a salt thereof, resveratrol or a salt thereof, quercetin or a salt thereof, astaxanthin or a salt thereof, chlorophyll or a salt thereof, menaquinone MK7 (K2) or a salt thereof, CoQ10, optionally soybean oil, optionally flax seed oil, turmeric root extract, boswellia extract, grape seed extract, rosemary leaf extract, cayenne pepper, ginkgo leaf extract, Korean *ginseng* root extract, and garlic bulb, wherein the myo-inositol can be present in the formulation, individually, in each case, in an amount of from about 10 mg to about 160 mg.

Provided are methods comprising administration of at least one formulation described herein, wherein at least one formulation can be administered orally, intravenously, intraperitoneal, subcutaneous, topically, or a combination thereof. Optionally, at least one formulation can be administered as a pill, or as two or more pills. The two or more pills can be administered simultaneously, sequentially, or intermittently. At least one formulation can be administered as a powder formulation. At least one formulation can be administered as a combination of one or more pills and a powder formulation. The combination can be administered simultaneously, sequentially, or intermittently.

Solid Dosage Forms for Oral Use

In some embodiments, formulations for oral use include tablets containing the active ingredient(s) in a mixture with non-toxic physiologically or pharmaceutically acceptable excipients.

These excipients may be, for example, inert diluents or fillers (e.g., sucrose, sorbitol, sugar, mannitol, microcrystalline cellulose, starches including potato starch, calcium carbonate, sodium chloride, lactose, calcium phosphate, calcium sulfate, or sodium phosphate); granulating and disintegrating agents (e.g., cellulose derivatives including microcrystalline cellulose, starches including potato starch, croscarmellose sodium, alginates, or alginic acid); binding agents (e.g., sucrose, glucose, sorbitol, acacia, alginic acid, sodium alginate, gelatin, starch, pregelatinized starch, microcrystalline cellulose, magnesium aluminum silicate, carboxymethylcellulose sodium, methylcellulose, hydroxypropyl methylcellulose, ethylcellulose, polyvinylpyrrolidone, or polyethylene glycol); and lubricating agents, glidants, and anti-adhesives (e.g., magnesium stearate, zinc stearate, stearic acid, silicas, hydrogenated vegetable oils, or talc). Other physiologically or pharmaceutically acceptable excipients can be colorants, flavoring agents, plasticizers, humectants, buffering agents, and the like.

The tablets may be uncoated, optionally to delay disintegration and absorption in the gastrointestinal tract and thereby providing a sustained action over a longer period. The coating may be adapted to release the protein in a predetermined pattern (e.g., in order to achieve a controlled release formulation) or it may be adapted not to release the agent(s) until after passage of the stomach (enteric coating). The coating may be a sugar coating, a film coating (e.g., based on hydroxypropyl methylcellulose, methylcellulose, methyl hydroxyethyl cellulose, hydroxypropylcellulose, carboxymethylcellulose, acrylate copolymers, polyethylene glycols and/or polyvinylpyrrolidone), or an enteric coating (e.g., based on methacrylic acid copolymer, cellulose acetate phthalate, hydroxypropyl methylcellulose phthalate, hydroxypropyl methylcellulose acetate succinate, polyvinyl acetate phthalate, shellac, and/or ethylcellulose). Furthermore, a time delay material such as, e.g., glyceryl monostearate or glyc-eryl distearate, may be employed.

The solid tablet compositions may include a coating adapted to protect the composition from unwanted chemical changes, (e.g., chemical degradation prior to the release of the active substances).

The compositions described herein may be mixed together in the tablet, or may be partitioned. In one example, a first agent is contained on the inside of the tablet, and a second agent is on the outside, such that a substantial portion of the second agent is released prior to the release of the first agent. Formulations for oral use may also be presented as chewable tablets, or as hard gelatin capsules wherein the active ingredient is mixed with an inert solid diluent (e.g., potato starch, lactose, microcrystalline cellulose, calcium carbonate, calcium phosphate, or kaolin), or as soft gelatin capsules wherein the active ingredient is mixed with water or an oil medium, for example, peanut oil, liquid paraffin, or olive oil. Powders and granulates may be prepared using the ingredients mentioned above under tablets and capsules in a conventional manner using, e.g., a mixer, a fluid bed apparatus, or spray drying equipment.

In solid dosage forms of the compositions described herein for oral administration (capsules, tablets, pills, dragees, powders, granules and the like), the active ingredients can be mixed with one or more physiologically or pharmaceutically acceptable carriers, such as sodium citrate or dicalcium phosphate, and/or any of the following: fillers or extenders, such as starches, lactose, sucrose, glucose, mannitol, and/or silicic acid; binders, such as, for example, carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and sodium carbonate; solution retarding agents, such as paraffin; absorption accelerators, such as quaternary ammonium compounds; wetting agents, such as, for example, cetyl alcohol and glycerol monostearate; absorbents, such as kaolin and bentonite clay; lubricants, such a talc, calcium stearate, magnesium stearate, solid polyethylene glycols, sodium lauryl sulfate, and mixtures thereof; and coloring agents. In the case of capsules, tablets and pills, the supplement formulations described herein may also comprise buffering agents. Solid compositions of a similar type may also be employed as fillers in soft and hard-filled gelatin capsules using such excipients as lactose or milk sugars, as well as high molecular weight polyethylene glycols and the like, as well as vegan potato protein.

Solid composition excipients like lactose and/or vegan potato protein stabilize the active ingredients that are present in an oil such that solid-form dosage formulations are possible to manufacture and administer.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the supplement formulations of the present compositions described herein, such as dragees, capsules, pills and granules, may optionally be scored or prepared with coatings and shells, such as enteric coatings and other coatings. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally be of a composition that releases the active ingredient(s) only, or preferentially, in a certain portion of the gastrointestinal tract, optionally, in a delayed manner.

Examples of embedding compositions which can be used include polymeric substances and waxes. The active ingredient can also be in micro-encapsulated form, if appropriate, with one or more of the above-described excipients. In one aspect, a solution of resolvin and/or protectin or precursor or analog thereof can be administered as eye drops for ocular neovascularization or ear drops to treat otitis.

The formulations can be administered as tablets once or twice a day. More than one tablet can be administered at the same time. The formulation can be administered as capsules once or twice a day. More than one capsule can be administered at the same time. The formulation can be administered as liquid doses once or twice a day. More than one liquid dose can be administered at the same time. The compositions can be administered by inhalation once or twice a day.

At least one formulation can be administered as a liquid formulation. The liquid formulation can be obtained by reconstituting a powder formulation in a liquid. At least one formulation can be administered as a combination of one or more pills and a liquid formulation. The combination can be administered simultaneously, sequentially, or intermittently. At least one formulation can be administered as an emulsion formulation. At least one formulation can be administered as a combination of one or more pills and an emulsion formulation. The combination can be administered simultaneously, sequentially, or intermittently. At least one formulation can be mixed in food. The food can be a beverage, a shake, or a snack. The beverage can be tea, coffee, or energy drink. The food can be consumed by the subject as part of a meal or diet plan.

In some embodiments, liquid dosage forms for oral administration of the compounds of the compositions described herein include pharmaceutically acceptable emulsions, microemulsions, solutions, suspensions, syrups and elixirs.

In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

EXAMPLES

Example 1. Analysis of the formulations by High Performance Liquid Chromatography Sample Preparation:

In Liquid Form:

30 ml of the sample solution is added to 25 ml methanol in a volumetric flask and is sonicated for 15 minutes. Afterwards, methanol is slowly added until the lowest part of the meniscus reaches the graduation mark of the flask and is then mixed thoroughly in the flask. Lastly, the solution is filtered with a 0.4 um filter.

In Solid Form:

More than 20 tablets or capsules are ground into a powder. A given mass of the powder (accurate to 0.001 g) is put into a 50 ml volumetric flask. Methanol is added to the powder and the mixture is sonicated for 15 minutes. Next, methanol is added to the solution until its lowest meniscus reaches the graduation mark of the flask. The solution is then centrifuged at 3000 rpm for 3 minutes. The supernatent is collected and filtered with a 0.4 um filter.

HPLC Analysis:

The HPLC analysis is performed at room temperature. The HPLC instrument comprises a reservoir, a high-pressure pump, an injector, a column, and a detector. The reservoir holds a mobile phase solvent. The high-pressure pump generates and meters a specified flow rate of the mobile phase solvent. The injector introduces the sample into the continuously flowing mobile phase stream that carries the sample into the HPLC column. The column contains the chromatographic packing material (e.g., stationary phase) needed to effect the separation. The detector identifies separated component bands as they elute from the HPLC column. Depending on the characteristics of components in the sample, several types of detectors can be used, for example, a UV-absorbance detector, a fluorescence detector, or an evaporative-light-scattering detector. The mobile phase exits the detector and is sent to waste.

A series of reference solutions are prepared and analyzed by the HPLC. Each of the reference solutions is a pure solution of each component that will be analyzed in the sample solution. Each of the reference solutions is used to obtain the reference retention time and the reference area under the peak of each component. The reference retention time is shown by the time interval between the injection and the maximum of a peak in the chromatogram. The reference area under the peak is proportional to the reference concentration of each component and can be calculated automatically by the computer linked to the HPLC. The reference concentration is obtained when the reference solution is prepared.

The sample solution is then analyzed by the HPLC. The sample solution is used to obtain the actual retention time and the actual area under the peak of each component in the sample. The actual retention time is shown by the time interval between the injection and the maximum of a peak in the chromatogram. The matching of a reference retention time and an actual retention time confirms the identity of a given component in the sample. The actual area under the peak is proportional to the actual concentration of each component in the sample and can be calculated automatically by the computer linked to the HPLC. The actual concentration of a given component is determined based on the reference area under the peak of the given component, the reference concentration of the given component, and the actual area under the peak of the given component.

Example 2. Manufacturing of the Formulations

The ingredient powders (prepared as described above) are first accurately weighed according to a master formula with an electronic balance. The identity and quantity of each item to be weighed is verified. The weighed ingredients and excipients are then loaded into a fluid bed dryer. Air flow is adjusted so that the powders are mixed sufficiently for 25-30 minutes. A moisturizing agent (65% ethanol) is then sprayed into the fluid bed dryer to allow the powder to granulate. During this process, the equipment inlet air temperature is maintained at 35-50° C. and the outlet air temperature is at 25-30° C. After forming 20 mesh size granules, the granules are dried at 55±2° C. The dried granules are then screened and sifted with an 18 mesh size stainless steel sieve by vibrating with screening machine. Magnesium stearate is used as a lubricant and is added at 0.2% of the total weight of the granules. The powder is then mixed in a 3D motion mixer for 20 minutes. After being mixed sufficiently, 20 grams of the resulting powder is sampled for QC using an in-process control test for moisture (e.g., less than 4%).

After passing the QC in-process control test, the granules are transferred to a rotary tableting machine for tableting. The pressure, rotating speed and the tablet weight are adjusted so that each tablet weight reaches 1.2 g. The tablet fill weight and the intermediate product weight variation control range can be 1.2 g±7%. During the tableting process, 10 tablets are sampled and weighed for the total and individual weights every 20 minutes to check for weight variation. After tableting, 50 tablets are sampled for weight variation. Twenty tablets are subjected to a disintegration test (e.g., disintegrate within 30 minutes).

Film-coating of the tablets is carried out using a film-coating machine. Film-coating solution is prepared by combining a pre-mixed film-coating agent and 50% ethanol. The ratio between the pre-mixed film-coating agent and 50% ethanol is 1:7. The amount of coating (by weight) does not exceed 3-6% of the uncoated tablet weight. A sample of coated tablets are subjected to a disintegration test (e.g., disintegrate within 60 minutes). A sample of tablets may also be tested for ash content, heavy metal (arsenic, lead, mercury), microbes (total aerobic, *E. coli*, yeast and mold, pathogens), and/or pesticides.

The tablets are counted, filled into bottles and fitted with proper closures. The pack size is 50 tablets per bottle. During the internal packaging process, 3 bottles will be sampled on 3 occasions to test for seal integrity, count size, and closure fitness.

Filled bottles are affixed with labels imprinted with batch number and expiration date. Labelled bottles are then sealed with transparent full body sleeve shrink wrap. 100 bottles are packed into 1 carton. 7 bottles are sampled on three occasions to test for batch number and expiration date, label position, shrink wrap position, fitness, smoothness, cleanliness and integrity. After passing the QC test, the product will be released as finished products and properly stored.

Example 3. Whether the Category 1 Formulations are Effective in Healthy Volunteers This study is designed to determine whether the category 1 formulations are effective in healthy volunteers. Specifically, this study is designed to determine whether the category 1 formulations can help individuals, among other things, enhance cognitive function and alertness, facilitate memory processing, support central nervous system performance and regulation, increase motivation and drive, improve focus, clarity, and concentration, increase speed of cognition and information processing, improve wakefulness and alertness, reduce anxiety and stress, increase energy levels, increase stamina or endurance, improve reaction times, enhance creativity, balance mood, enhance clarity, increase mental stamina, eliminate mental gridlock, boost speed of thought, regulate the synthesis of a number of neurotransmitters, improve brain cell function and production, increase antioxidant activity and brain blood flow, modulate pain receptors, and enhance neural growth and neuroplasticity. An exemplary category 1 formulation is provided in the table below.

TABLE 1

Exemplary Category 1 Formulation

| Ingredient | Amount (mg/serving; 2 tablets)* |
|---|---|
| Vitamin D3 (as cholecalciferol) | 0.02 |
| Niacin (as niacinamide) | 16 |
| Vitamin B12 | 0.060 |
| Magnesium (as magnesium oxide & magnesium aspartate) | 105 |
| Zinc (as zinc amino acid chelate) | 11 |
| NeuroSupport Herbal Blend | 400 |
| Green Tea Leaf Extract (standardized for epigallocatechin gallate (EGCG)) | 300 |
| Ginkgo Leaf Extract | 40 |
| Ginger Root Extract | 40 |
| Cayenne Pepper | 14 |
| Rhodiola Root Extract | 3 |
| Korean Ginseng Root | 3 |
| NeuroPerformance Nutrient Blend | 500 |
| Bacopa Leaf Extract (50% bacopasides) | 300 |
| L-Theanine | 180 |
| Resveratrol | 10 |
| 2-dimethylaminoethanol | 10 |
| pyrroloquinoline quinone disodium salt | 0.50 |
| Amino Acid Neuronutrient Complex | 300 |
| DL-Phenylalanine | 70 |
| L-Tyrosine HCl | 65 |
| L-Arginine HCl | 65 |
| Taurine | 60 |
| 5-hydroxytryptophan (from Griffonia simplicifolia seed extact) | 20 |
| Creatine Monohydrate | 20 |
| Excipients Cellulose, Stearic Acid, Bamboo Extract (Silicon Dioxide), Magnesium Stearate, Titanium Oxide, Natural Vanillin and Peppermint, Polyethylene Glycol, Riboflavin (color), and Carnauba Wax | |

* = approximate mass

Subjects and Estimation of Sample Size:

In order to minimize variations in demographic and baseline variables, the recruitment of subjects is limited to non-professional, college-level students who meet the following criteria: 1) age 18-22 years; 2) have moderate exercises in a regular manner, defined as doing exercises at least 3-4 hours per week; and 3) study in a regular manner, defined as studying at least 5-6 hours per day. Those who have unstable medical conditions, a history of alcohol or substance abuse within 1 year prior to the study, needle phobia, or are currently under other types of dietary supplements are excluded from this study. Thus, seventy college-level students (18-22 years old) are selected to take the category 1 formulations (2 tablets/day) for 7 weeks.

Study Design and Procedures:

Self-report surveys are conducted at baseline (pretreatment), week 4, and endpoint (after completion of the treatment). The self-report surveys are questionnaires consisting of a set of statements and/or questions. These statements and/or questions are designed to examine a large number of variables related to the effectiveness of the category 1 formulations. The statements and/or questions are designed as rating scale statements, requiring the subjects to decide how strongly they agree or disagree with the given statements. The response options are "strongly agree," "agree," "undecided," "disagree," and "strongly disagree." Examples of these statements include, but not limited to, "after taking the formulation, your cognitive function and alertness are enhanced," "after taking the formulation, your memory processing is enhanced," "after taking the formulation, your motivation and drive are increased," "after taking the formulation, your focus, clarity, and concentration are improved," "after taking the formulation, your speed of cognition and information processing is improved," "after taking the formulation, your wakefulness and alertness are improved," "after taking the formulation, your anxiety and stress are reduced," "after taking the formulation, your energy levels are increased," "after taking the formulation, your stamina and endurances are improved," "after taking the formulation, your creativity is enhanced," and "after taking the formulation, your mood is uplifted."

Example 4. Whether the Category 2 Formulations are Effective in Volunteers

This study is designed to determine whether the category 2 formulations are effective in selected volunteers. Specifically, this study is designed to determine whether the category 2 formulations can help individuals, among other things, induce and maintain sleep, calm down, stabilize their mod, regulate their clock, sleep-wake cycle, facilitate memory processing, support nervous system health, promote relaxation, reduce symptoms of stress and anxiety, improve cognition and memory, improve quality of sleep, reduce time required to fall asleep, achieve deep, restful sleep, uplift mood, offset caffeine in other dietary supplements, reduce brain cell activity, result in a relaxed state, wake up feeling refreshed and enable rejuvenated mornings, optimize memory consolidation, recovery, and neuroprotective processes, enhance cognition generally and the day after quality night of sleep, or feel more relaxed. An exemplary category 2 formulation is provided in the table below.

TABLE 2

Exemplary Category 2 Formulation

| Ingredient | Amount (mg/serving; 2 tablets)* |
|---|---|
| Vitamin D3 (as cholecalciferol) | 0.02 |
| Niacin (as niacinamide) | 16 |
| Vitamin B6 | 4.25 |
| Folate | 0.635 |
| Pantothenic Acid (dicalcium pantothenate) | 15 |

TABLE 2-continued

Exemplary Category 2 Formulation

| Ingredient | Amount (mg/serving; 2 tablets)* |
|---|---|
| Calcium (as calcium carbonate) | 130 |
| Magnesium (as magnesium oxide & magnesium bisglycinate) | 315 |
| Special AminoSerenity Complex | 550 |
| GABA (gama-aminobutyric acid) | 300 |
| L-Theanine | 140 |
| Taurine | 64 |
| L- Glutamine | 20 |
| Myo-Inositol | 16 |
| Melatonin | 8 |
| Phosphatidyl serine | 2 |
| Herbal Serenity Blend | 280 |
| Valerian Root Extract | 140 |
| 5-hydroxytryptophan | 34 |
| Ashwagandha Root Extract | 28 |
| Chamomile Flower Extract | 24 |
| Hops Flower Extract | 24 |
| Passion Flower Extract | 20 |
| Lemon Balm Leaf Extract | 10 |
| Excipients | |
| Cellulose, Stearic Acid, Bamboo Extract (Silicon Dioxide), and Peppermint, Polyethylene Glycol, Chlorophyll, and Carnauba Wax Magnesium Stearate, Titanium Oxide, Natural Vanillin | |

* = approximate mass

Subjects and Estimation of Sample Size:

In order to minimize variations in demographic and baseline variables, the recruitment of subjects is limited to non-professional, college-level students who meet the following criteria: 1) age 18-22 years; 2) have moderate exercises in a regular manner, defined as doing exercises at least 3-4 hours per week; 3) study in a regular manner, defined as studying at least 5-6 hours per day; and 4) have sleep problems (e.g., inability to fall asleep, taking longer time to fall asleep) within 3 months prior to the study. Those who have unstable medical conditions, a history of alcohol or substance abuse within 1 year prior to the study, needle phobia, or are currently under other types of dietary supplements are excluded from this study. Thus, seventy college-level students (18-22 years old) are selected to take the category 2 formulations (2 tablets/day) for 7 weeks.

Study Design and Procedures:

Self-report surveys are conducted at baseline (pretreatment), week 4, and endpoint (after completion of the treatment). The self-report surveys are questionnaires consisting of a set of statements and/or questions. These statements and/or questions are designed to examine a large number of variables related to the effectiveness of the category 2 formulations. The statements and/or questions are designed as rating scale statements, requiring the subjects to decide how strongly they agree or disagree with the given statements. The response options are "strongly agree," "agree," "undecided," "disagree," and "strongly disagree." Examples of these statements include, but not limited to, "after taking the formulation, your sleep quality is improved," "after taking the formulation, your memory processing is enhanced," "after taking the formulation, you feel more relaxed," "after taking the formulation, your anxiety and stress are reduced," "after taking the formulation, the time required for you to fall asleep is reduced," "after taking the formulation, your sleep is deeper and more restful," "after taking the formulation, your mood is uplifted," "after taking the formulation, you wake up feeling more refreshed and rejuvenated," and "after taking the formulation, your cognition during the day is enhanced because your sleep quality is improved."

Example 5. Whether the Category 3 Formulations are Effective in Healthy Volunteers Exemplary Category 3 Formulation

| Ingredient | Amount (mg/serving; 4 tablets)* |
|---|---|
| Vitamin A (as retinyl acetate and beta carotene) | 0.9 |
| Vitamin C (as ascorbic acid) | 0.225 |
| Vitamin D3 (as cholecalciferol) | 0.05 |
| Vitamin E (as d-alpha tocopheryl succinate) | 21 |
| Vitamin K (as phytonadione (K1)) | .180 |
| Thiamin (as thiamine HCl) | 6 |
| Riboflavin | 6.5 |
| Niacin (as niacinamide) | 16 |
| Vitamin B6 (as pyridoxyl 5 phosphate) | 8.5 |
| Folate (as L-5-Methyltetrahydrofolate) | 0.6 |
| Vitamin B12 (as methylcobalamin) | 0.024 |
| Biotin | 0.075 |
| Pantothenic Acid (as d-calcium pantothenate) | 10 |
| Choline (as choline bitartrate, phosphatidylcholine, citicoline & glycerophosphatocholine) | 55 |
| Calcium (as calcium carbonate & d-calcium pantothenate) | 10 |
| Iron (as carbonyl iron) | 9 |
| Iodine (as potassium iodide) | .150 |
| Magnesium (as magnesium oxide & magnesium glycinate) | 315 |
| Zinc (as zinc oxide) | 11 |
| Selenium (as 1-selenomethionine) | 0.055 |
| Copper (as copper gluconate) | 1.8 |
| Manganese (as manganese glycinate) | 2.3 |
| Chromium (as chromium picolinate) | 0.07 |
| Molybdenum (as sodium molybdate) | 0.045 |
| Omega-3 Fish Oil Conc. | 210 |
| Omega-3 DHA (docosahexaenoic acid) | 180 |
| Omega-3 EPA (eicosapentaenoic acid) | 30 |
| Restore Dayli Phospholipid Complex | 250 |
| Myo-Inositol | 15 |
| Choline (as choline bitartrate, citicoline, and/or phosphatidylcholine) | 220 |
| Alpha-GPC (glycerophosphatocholine) | 6 |
| Phosphatidylserine | 6 |
| Alpha-Linolenic Acid | 3 |
| Restore Dayli Support Complex | 250 |
| L-Arginine HCL | 55 |
| L-Citrulline | 40 |
| Taurine | 40 |
| Beet Root Extract | 40 |
| Acetyl-L-Carnitine | 25 |
| Resveratrol | 20 |
| Quercetin | 5 |
| Chlorophyll | 2 |
| Astaxanthin | 1 |
| Coenzyme Q10 | 0.25 |
| Menaquinone MK7 (K2) | 0.01 |
| Restore Dayli Support Complex | 325 |
| Tumeric Root Extract | 80 |
| Citrus Bioflavonoids Concentrate | 80 |
| Ginger Root Extract | 40 |
| Boswellia Extract | 26 |
| Red Grape Seed Extract | 25 |
| Rosemary Leaf Extract | 24 |
| Cayenne Pepper | 20 |
| Ginkgo Leaf Extract | 20 |
| Korean Ginseng Root Extract | 5 |
| Garlic Bulb | 5 |
| Excipients | |
| Cellulose, Stearic Acid, Bamboo Extract (Silicon Dioxide), Cellulose Gum, Magnesium Stearate, Titanium Oxide, Natural Vanillin and Peppermint, Polyethylene Glycol, Natural Caramel (color), and Carnauba Wax | |

* = approximate mass

This study is designed to determine whether the category 3 formulations are effective in healthy volunteers. Specifically, this study is designed to determine whether the category 3 formulations can help individuals, among other things, promote learning and memory, support cognitive function, restore and stabilize cells, facilitate energy production, improve mental and emotional health, stabilize metabolism rate and mood, facilitate chemical reactions critical to health, limit stress and anxiety, improve attention and focus, improve mental performance and ability to concentrate, improve overall well-being and better energy, or support long-term brain health.

Subjects and Estimation of Sample Size:

In order to minimize variations in demographic and baseline variables, the recruitment of subjects is limited to non-professional, college-level students who meet the following criteria: 1) age 18-22 years; 2) have moderate exercises in a regular manner, defined as doing exercises at least 3-4 hours per week; and 3) study in a regular manner, defined as studying at least 5-6 hours per day. Those who have unstable medical conditions, a history of alcohol or substance abuse within 1 year prior to the study, needle phobia, or are currently under other types of dietary supplements are excluded from this study. Thus, seventy college-level students (18-22 years old) are selected to take the category 3 formulations (2 tablets/day) for 7 weeks.

Study Design and Procedures:

Self-report surveys are conducted at baseline (pretreatment), week 4, and endpoint (after completion of the treatment). The self-report surveys are questionnaires consisting of a set of statements and/or questions. These statements and/or questions are designed to examine a large number of variables related to the effectiveness of category 3 formulations. The statements and/or questions are designed as rating scale statements, requiring the subjects to decide how strongly they agree or disagree with the given statements. The response options are "strongly agree," "agree," "undecided," "disagree," and "strongly disagree." Examples of these statements include, but not limited to, "after taking the formulation, your memory and learning are promoted," "after taking the formulation, your cognitive function is enhanced," "after taking the formulation, you feel more energetic," "after taking the formulation, your stress and anxiety are reduced," "after taking the formulation, your attention and focus are improved," "after taking the formulation, your mental performance is improved," "after taking the formulation, your ability to concentrate is improved," and "after taking the formulation, your overall well-being is improved."

Example 6. 16-Week Trial of Users Across Various Ages Taking Category 1 Formulations, Category 2 Formulations, and Category 3 Formulations This study was designed to determine whether category 1 formulations, category 2 formulations, and category 3 formulations are effective in healthy volunteers. Specifically, this study was designed to determine whether the formulations can help individuals, among other things, promote learning and memory, support cognitive function, restore and stabilize cells, facilitate energy production, improve mental and emotional health, stabilize metabolism rate and mood, facilitate chemical reactions critical to health, limit stress and anxiety, improve attention and focus, improve mental performance and ability to concentrate, improve overall well-being and better energy, support long-term brain health, improve quality of sleep, wake up feeling refreshed, and enable rejuvenated mornings.

Subjects and Estimation of Sample Size:

In order to minimize variations in demographic and baseline variables, participants from various age and gender groups were invited to partake in the study. People who had unstable medical conditions, a history of alcohol or substance abuse within 1 year prior to the study, needle phobia, or were, at the time of the study, under other types of dietary supplements were excluded from this study. Fifteen participants completed the entire study and reported their observations. Thirteen percent of the participants were between 25-30 years old. Seven percent of the participants were between 31-35 years old. Twenty percent of the participants were between 36-40 years old. Thirteen percent of the participants were between 41-45 years old. Twenty-seven percent of the participants were between 51-55 years old. Seven percent of the participants were between 56-60 years old. Thirteen percent of the participants were between 61-65 years old. Additionally, sixty-seven percent of the participants were female while the remaining thirty-three percent of the participants were male.

Study Design and Procedures

Participant progress was monitored bi-monthly and individuals used a self tracker weekly to measure their results. Additionally, an online survey was deployed at the end of the 4-week trial, at the 8-week mark, at 12 weeks and again at 16 weeks of use. The survey asked participants to broadly score the "total system" comprising category 1 formulations, category 2 formulations, and category 3 formulations on a 1-5 system, 5, designating the highest level of satisfaction. More specifically, the online surveys comprised questionnaires consisting of a set of statements and/or questions. These statements and/or questions were designed to examine a large number of variables related to the effectiveness of the category 1 formulations, category 2 formulations, and category 3 formulations. The statements and/or questions were designed as rating scale statements, requiring the subjects to decide how strongly they agreed or disagreed with the given statements. The response options were "strongly agree," "agree," "undecided," "disagree," and "strongly disagree." Examples of these statements included, but were not limited to, "after taking the formulation, your cognitive function and alertness are enhanced," "after taking the formulation, your memory processing is enhanced," "after taking the formulation, your motivation and drive are increased," "after taking the formulation, your focus, clarity, and concentration are improved," "after taking the formulation, your speed of cognition and information processing is improved," "after taking the formulation, your wakefulness and alertness are improved," "after taking the formulation, your anxiety and stress are reduced," "after taking the formulation, your energy levels are increased," "after taking the formulation, your stamina and endurances are improved," "after taking the formulation, your creativity is enhanced," and "after taking the formulation, your mood is uplifted," "after taking the formulation, your sleep quality is improved," "after taking the formulation, you feel more relaxed."

Results

Figure 2:
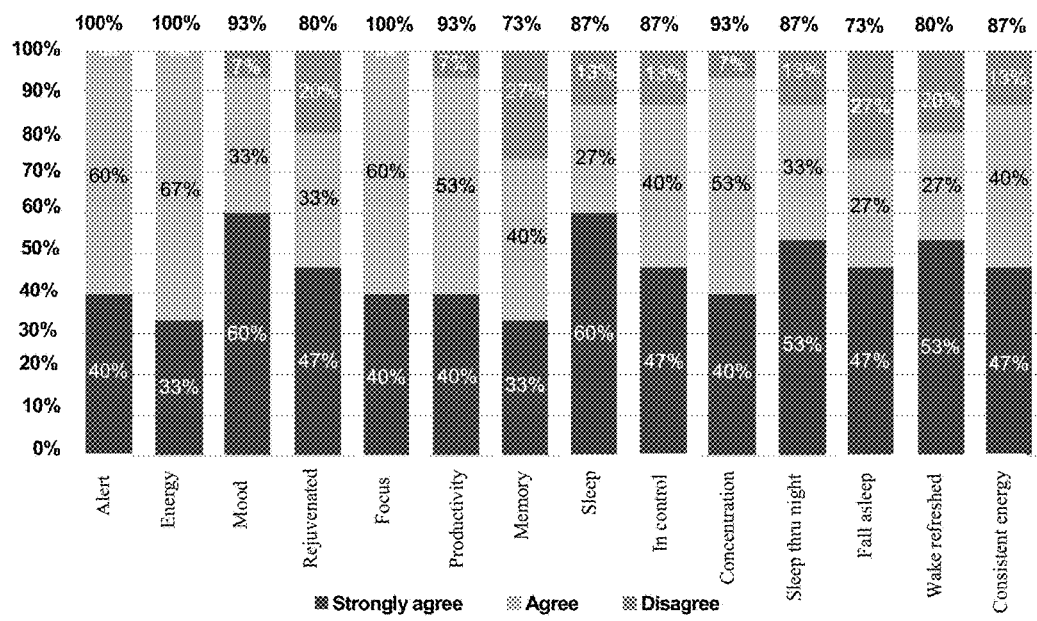
FIG. 2 shows the results of the 16-week study on the effects of category 1 formulations, category 2 formulations, and category 3 formulations on participants on specific qualities of life tested for in the study.

Overall, the total system rating increased among all participants. But participants aged 36 or older reported greater scores over the entire course of the study. Scores were recorded at the end of the 4-week trial, at the 8-week mark, at 12 weeks and again at 16 weeks of use. The results of the total system scoring are in FIG. 1. Generally, the majority of participants reported improvements in all of the specifically tested categories. Specifically, upon completion of the 16-week study, 100 percent of participants noted improvements in alertness, energy and focus. And 93 percent of participants noted improvements in mood, productivity, and concentration. The results for questions presented in the study are in FIG. 2.

Example 7. 4 and 5 Months ON Regimen of Category 1 Formulations, Category 2 Formulations, and Category 3 Formulations Vs 2 Weeks OFF all Formulations Presented Herein This study was designed to determine whether category 1 formulations, category 2 formulations, and category 3 formulations are effective in healthy volunteers. Specifically, this study was designed to determine whether users of the formulations noticed deficiencies in, among other things, learning and memory, cognitive function, cell stability, energy production, mental and emotional health, metabolism rate and mood, chemical reactions critical to health, stress and anxiety control, attention and focus, mental performance and ability to concentrate, overall well-being and energy, long-term brain health, quality of sleep, and waking up feeling refreshed and rejuvenated, when ceasing taking the formulations for a two week time period following either a four month or five month regime taking the formulations. For clarity, no significant differences were reported between participants in the four month and five month regimes, thus participants from these studies were referred to, collectively, as ON. The results from the participants during the two week period where no formulations were ingested were referred to as OFF.

Subjects and Estimation of Sample Size:

In order to minimize variations in demographic and baseline variables, participants from various age and gender groups were invited to partake in the study. People who had unstable medical conditions, a history of alcohol or substance abuse within 1 year prior to the study, needle phobia, or were, at the time of the study, under other types of dietary supplements were excluded from the study. Thirteen participants completed the entire study and reported their observations. Sixteen percent of the participants were between 25-30 years old. Twenty-three percent of the participants were between 36-40 years old. Eight percent of the participants were between 41-45 years old. Twenty-three percent of the participants were between 51-55 years old. Fifteen percent of the participants were between 56-60 years old. Fifteen percent of the participants were between 61-65 years old. Additionally, sixty-two percent of the participants were female while the remaining thirty-eight percent of the participants were male.

Study Design and Procedures

Participant progress was monitored bi-monthly and individuals used a self tracker weekly to measure their results. Twenty one participants started with a 5-day trial. The final report was narrowed down to the 13 participants who remained and submitted surveys for both 4 month and 5 month usage, plus surveys after 1 and 2 weeks off the regimen in between. The online surveys comprised questionnaires consisting of a set of statements and/or questions. These statements and/or questions were designed to examine a large number of variables related to the effectiveness of the category 1 formulations, category 2 formulations, and category 3 formulations. The statements and/or questions were designed as rating scale statements, requiring the subjects to decide how strongly they agreed or disagreed with the given statements. The response options were "strongly agree," "agree," "undecided," "disagree," and "strongly disagree." Examples of these statements included, but were not limited to, "after taking the formulation, your cognitive function and alertness are enhanced," "after taking the formulation, your memory processing is enhanced," "after taking the formulation, your motivation and drive are increased," "after taking the formulation, your focus, clarity, and concentration are improved," "after taking the formulation, your speed of cognition and information processing is improved," "after taking the formulation, your wakefulness and alertness are improved," "after taking the formulation, your anxiety and stress are reduced," "after taking the formulation, your energy levels are increased," "after taking the formulation, your stamina and endurances are improved," "after taking the formulation, your creativity is enhanced," and "after taking the formulation, your mood is uplifted," "after taking the formulation, your sleep quality is improved," "after taking the formulation, you feel more relaxed." Responses from the ON trials were pooled together and compared to the responses from the OFF trials.

Results

Figure 3:
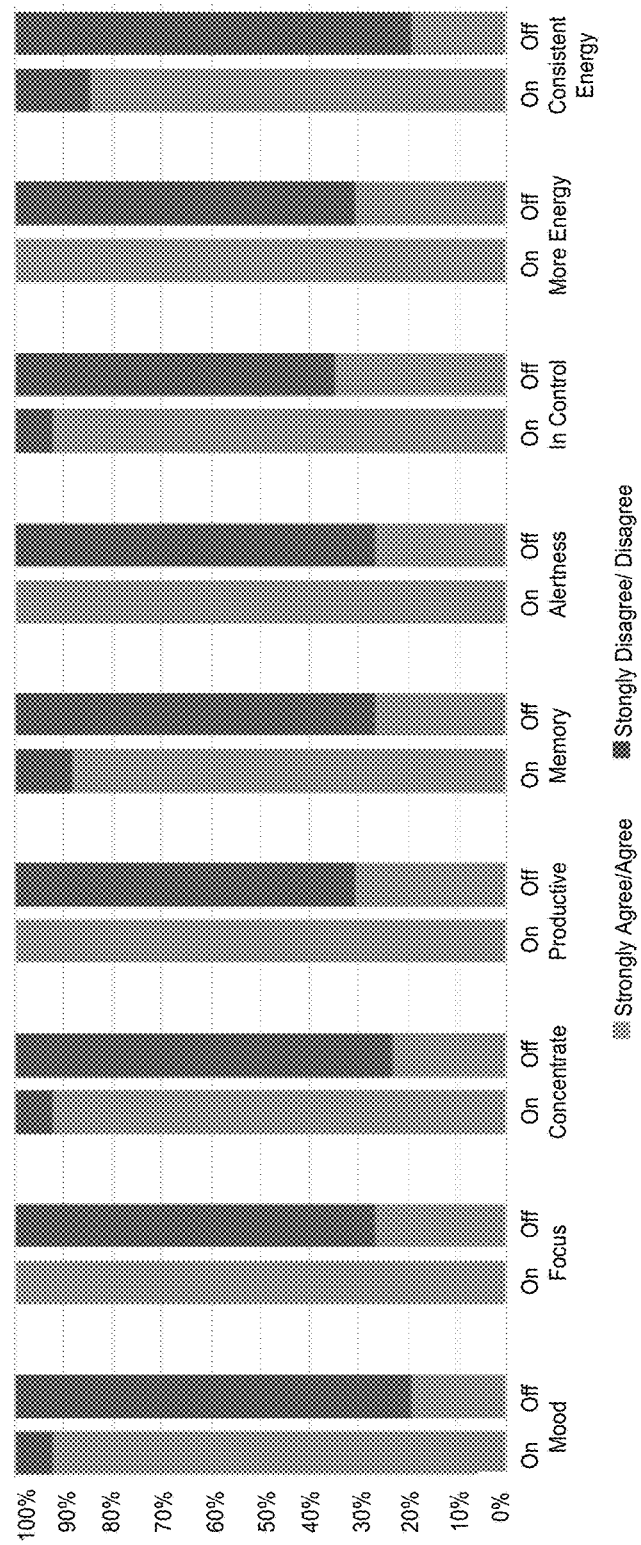
FIG. 3 shows the results of a study comparing user responses from participants of either a 4-month or 5-month regime of category 1 formulations, category 2 formulations, and category 3 formulations to user responses from the same participants when they were prohibited from ingesting any of the formulations described herein.

Overall, improvement ratings showed a significant change between averaged months 4/5 when respondents were "ON" the regimen vs the 2 weeks "OFF" the regimen. The results are depicted in FIG. 3. 50-70 percent of participants reported noticing deficiencies in the tested categories when OFF the regimen.

What is claimed is:
1. A sleep supplement formulation comprising:
    a. L-glutamine or a salt thereof, wherein the L-glutamine is present in an amount from about 1 mg to about 50 mg,
    b. L-theanine or a salt thereof, wherein the L-theanine is present in an amount from about 10 mg to about 300 mg,
    c. taurine or a salt thereof, wherein the taurine is present in an amount from about 10 mg to about 120 mg,
    d. GABA, wherein the GABA is present in an amount from about 10 mg to about 600 mg,
    e. melatonin, wherein the melatonin is present in an amount from about 1 mg to about 20 mg,
    f. phosphatidylserine, wherein the phosphatidylserine is present in an amount from about 0.1 mg to about 4 mg,
    g. myo-inositol, wherein said myo-inositol is present in said formulation in an amount of from about 8 mg to about 40 mg; and
    h. one or more physiologically or pharmaceutically acceptable carrier, wherein components (a)-(g) are formulated with the carrier in the form of a solid dosage for promoting sleep.
2. The sleep supplement formulation of claim 1, wherein said myo-inositol is present in said formulation in an amount of about 16 mg.
3. The sleep supplement formulation of claim 1, wherein said L-glutamine or a salt thereof is present in said formulation in an amount of from about 8 mg to about 50 mg.
4. The sleep supplement formulation of claim 1, wherein said L-theanine is present in said formulation in an amount of about 140 mg.
5. The sleep supplement formulation of claim 1, wherein said taurine or a salt thereof is present in said formulation in an amount of about 64 mg.
6. The sleep supplement formulation of claim 1, wherein said GABA is present in said formulation in an amount of about 300 mg.
7. The sleep supplement formulation of claim 1, wherein said melatonin or a salt thereof is present in said formulation in an amount of from about 7 mg to about 20 mg.
8. The sleep supplement formulation of claim 1, wherein said phosphatidylserine or a salt thereof is present in said formulation in an amount of from about 0.5 mg to about 4 mg.
9. The sleep supplement formulation of claim 1, further comprising:
    a. valerian root extract, wherein the valerian root extract is present in an amount from about 50 mg to about 300 mg;
    b. chamomile flower extract, wherein the chamomile flower extract is present in an amount from about 10 mg to about 50 mg;
    c. hops flower extract, wherein the hops flower extract is present in an amount from about 10 mg to about 50 mg;
    d. passion flower extract, wherein the passion flower extract is present in an amount from about 8 mg to about 60 mg;
    e. lemon balm leaf extract, wherein the lemon balm leaf extract is present in an amount from 1 mg to about 60 mg;
    f. 5 hydroxytryptophan or a salt thereof, wherein the 5-hydroxytryptophan is present in an amount from about 8 mg to about 60 mg; and
    g. ashwagandha root extract, wherein the ashwagandha root extract is present in said formulation in an amount of from about 8 mg to about 60 mg.
10. The sleep supplement formulation of claim 9, wherein said ashwagandha root extract is present in said formulation in an amount of about 28 mg.
11. The sleep supplement formulation of claim 9, wherein said valerian root extract is present in said formulation in an amount of about 140 mg.
12. The sleep supplement formulation of claim 9, wherein said chamomile flower extract is present in said formulation in an amount of about 24 mg.
13. The sleep supplement formulation of claim 9, wherein said hops flower extract is present in said formulation in an amount of about 24 mg.
14. The sleep supplement formulation of claim 9, wherein said 5-hydroxytryptophan or a salt thereof is present in said formulation in an amount of about 34 mg.
15. The sleep supplement formulation of claim 9, wherein said passion flower extract is present in said formulation in an amount of about 20 mg.
16. The sleep supplement formulation of claim 9, wherein said lemon balm leaf extract is present in said formulation in an amount of from about 8 mg to about 60 mg.
17. A method of promoting sleep in an individual in need thereof, by orally administering to the individual a supplement formulation comprising:
    a. L-glutamine or a salt thereof, wherein the L-glutamine is present in an amount from about 8 mg to about 50 mg,
    b. L-theanine or a salt thereof, wherein the L-theanine is present in an amount from about 10 mg to about 300 mg,
    c. taurine or a salt thereof, wherein the taurine is present in an amount from about 10 mg to about 120 mg,
    d. GABA wherein the GABA is present in an amount from about 10 mg to about 600 mg,
    e. melatonin, wherein the melatonin is present in an amount from about 1 mg to about 20 mg,
    f. phosphatidylserine, wherein the phosphatidylserine is present in an amount from about 0.1 mg to about 4 mg,
    g. myo-inositol, wherein said myo-inositol is present in said formulation in an amount of from about 8 mg to about 40 mg; and one or more physiologically or pharmaceutically acceptable carrier, wherein components (a)-(g) are formulated with the carrier in the form of a solid dosage for promoting sleep.

* * * * *